US009895454B2

(12) United States Patent
Sergeev et al.

(10) Patent No.: US 9,895,454 B2
(45) Date of Patent: Feb. 20, 2018

(54) METAL OXIDE CATALYZED RADIOFLUORINATION

(71) Applicant: The Regents of the University of California, Oakland, CA (US)

(72) Inventors: Maxim Sergeev, Los Angeles, CA (US); Federica Morgia, Los Angeles, CA (US); Robert Michael Van Dam, Los Angeles, CA (US); Mark Lazari, North Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/323,046

(22) PCT Filed: Jul. 2, 2015

(86) PCT No.: PCT/US2015/039095
§ 371 (c)(1),
(2) Date: Dec. 29, 2016

(87) PCT Pub. No.: WO2016/004377
PCT Pub. Date: Jan. 7, 2016

(65) Prior Publication Data
US 2017/0224851 A1    Aug. 10, 2017

Related U.S. Application Data

(60) Provisional application No. 62/020,840, filed on Jul. 3, 2014.

(51) Int. Cl.
| | | |
|---|---|---|
| *A61K 51/04* | (2006.01) |
| *C07B 59/00* | (2006.01) |
| *C07D 207/09* | (2006.01) |
| *C07C 17/361* | (2006.01) |
| *C07H 19/052* | (2006.01) |
| *C07D 207/16* | (2006.01) |
| *C07D 405/06* | (2006.01) |
| *C07C 67/333* | (2006.01) |
| *C07C 201/12* | (2006.01) |
| *C07C 253/30* | (2006.01) |
| *C07D 217/22* | (2006.01) |
| *C07D 241/16* | (2006.01) |
| *C07D 213/61* | (2006.01) |
| *B01J 21/06* | (2006.01) |

(52) U.S. Cl.
CPC .......... *A61K 51/04* (2013.01); *A61K 51/0446* (2013.01); *A61K 51/0453* (2013.01); *A61K 51/0455* (2013.01); *A61K 51/0459* (2013.01); *A61K 51/0491* (2013.01); *B01J 21/063* (2013.01); *C07B 59/001* (2013.01); *C07B 59/002* (2013.01); *C07B 59/005* (2013.01); *C07C 17/361* (2013.01); *C07C 67/333* (2013.01); *C07C 201/12* (2013.01); *C07C 253/30* (2013.01); *C07D 207/09* (2013.01); *C07D 207/16* (2013.01); *C07D 213/61* (2013.01); *C07D 217/22* (2013.01); *C07D 241/16* (2013.01); *C07D 405/06* (2013.01); *C07H 19/052* (2013.01); *C07B 2200/05* (2013.01); *C07C 2101/14* (2013.01)

(58) Field of Classification Search
None
See application file for complete search history.

(56) References Cited

U.S. PATENT DOCUMENTS

2013/0190529 A1    7/2013 Gouveneur et al.

OTHER PUBLICATIONS

Beaulieu, F. et al. (Nov. 5, 2009). "Aminodifluorosulfinium tetrafluoroborate salts as stable and crystalline deoxofluorinating reagents," *Org Lett* 11(21):5050-5053.
Bejot, R. et al. (2009). "Fluorous synthesis of 18F radiotracers with the [18F] fluoride ion: nucleophilic fluorination as the detagging process," *Angew Chem Int Ed engl* 48(3):586-589.
Cassidei, L. et al. (1985). "Experimental and theoretical NMR study of $^1$H-$^{19}$F inter-ring coupling constants in 2-fluoronaphthalene," *Spectrochimica Acta* 41A(12):1459-1462.
Chambers, R.D. et al. (1999). "Elemental fluorine. Part 10. Selective fluorination of pyridine, quinolone and quinoxaline derivatives with fluorine-iodine mixtures," *J Chem Soc Perkin Trans* 1:803-810.
Chun, J.H. et al. (Jun. 4, 2013, e-published Jun. 26, 2013). "Radiofluorination of diaryliodonium tosylates under aqueous-organic and cryptand-free conditions," *Org Biomol Chem* 11(31):5094-5099.
Enthaler, S. (Aug. 16, 2011, e-published Jul. 4, 2011). "Straightforward uranium-catalyzed dehydration of primary amides to nitriles," *Chemistry* 17(34):9316-9319.
Forlani, L. et al. (1995). "Interactions between amines and aromatic fluro derivatives. $^{19}$F NMR investigation in [$^2$H$_8$] toluene," *J Chem Soc Perkin Trans* 2(11):2019-2021.
Gieshoff, T.N. et al. (2015). "Iron-catalyzed Olefin Hydrogenation at 1 bar H2 with a FeCl3-LiAlH4 catalyst," *Green Chem* 17:1408.

(Continued)

Primary Examiner — Michael G Hartley
Assistant Examiner — Sun Y Kim
(74) Attorney, Agent, or Firm — Mintz Levin Cohn Ferris Glovsky and Popeo, P.C.

(57) ABSTRACT

Inter alia, the first titania-catalyzed [$^{18}$F]-radiofluorination in highly aqueous medium is provided. In embodiments, the method utilizes titanium dioxide, 1:1 acetonitrile-thexyl alcohol solvent mixture and tetrabutylammonium bicarbonate as a base. Radiolabeling may be directly performed with aqueous [$^{18}$F]fluoride without the need for drying/azeotroping step, which reduces radiosynthesis time while keeping high fluoride conversion. The general applicability of the synthetic strategy to the synthesis of the wide range of PET probes from tosylated precursors is demonstrated.

16 Claims, 16 Drawing Sheets

(56) References Cited

OTHER PUBLICATIONS

Graham, T.J. et al. (Apr. 9, 2014, e-published Mar. 31, 2014). "Enantioselective radiosynthesis of positron emission tomography (PET) tracers containing [$^{18}$F]fluorohydrins," *J Am Chem Soc* 136(14):5291-5294.
Habuda-Stanic, M. et al. (Sep. 5, 2014). "A Review on Adsorption of Fluoride from Aqueous Solution," *Materials* 7(9):6317-6366.
International Search Report dated Sep. 30, 2015, for PCT Application No. PCT/US2015/039095, filed on Jul. 2, 2015, 3 pages.
Javed, M.R. et al. (Feb. 2014, e-published Dec. 23, 2013). "Efficient radiosynthesis of 3'-deoxy-3'-18F-fluorothymidine using electrowetting-on-dielectric digital microfluidic chip," *J nucl Med* 55(2):321-328.
Javed, M.R. et al. (Feb. 7, 2014). "High yield and high specific activity synthesis of [18F]fallypride in a batch microfluidic reactor for micro-PET imaging," *Chem Commun* 50(10):1192-1194.
Jindrich, J. et al. (1992). "Synthesis of Isomeric N-(3-Fluoro-2-Hydroxypropyl) and N-(2-Fluoro-3-Hydroxypropyl) Derivatives of Purine and Pyrimidine Bases," *Collect Czech Chem Commun* 57:1466-1482.
Keng, P.Y. et al. (Jan. 17, 2012, e-published Dec. 30, 2011). "Micro-chemical synthesis of molecular probes on an electronic microfluidic device," *PNAS USA* 109(3):690-695.
Kim, K. et al. (Aug. 15, 2008, e-published Jul. 20, 2008). "A new multi-gram synthetic route to labeling precursors for the D(2/3) PET agent 18F-fallypride," *Bioorg Med Chem Lett* 18(16):4467-4469, supplementary information 6 pages.
Kim, D.Y. et al. (Mar. 21, 2012, e-published Feb. 9, 2012). "Synthesis of [18F]-labeled (6-fluorohexyl)triphenylphosphonium cation as a potential agent for myocardial imaging using positron emission tomography," *Bioconjug Chem* 23(3):431-437.
Koroniak, H. et al. (2006). "1,1,3,3,3-Pentafluoropropene secondary amine adducts new selective fluorinating agents," *Journal of Fluorine Chemistry* 127:1245-1251.
Kruger, T. et al. (Sep. 24, 2009). "Regioselective Arene Functionalization: Simple Substitution of Carboxylate by Alkyl Groups," *Chemistry a European Journal* 15:12082-12091.
Kumar, P. et al. (Nov. 2002). "Microwave-assisted (radio)halogenation of nitroimidazole-based hypoxia markers," *Appl Radiat Isot* 57(5):697-703.
Lu, S. et al. (2009). "Synthesis of [$^{18}$F] fallypride in a micro-reactor: rapid optimization and multiple-production in small doses for micro-PET studies," *Curr Radiopharm* 2(1):49-55.
Minella, M. et al. (Feb. 16, 2010). "Effect of fluorination on the surface properties of titania P25 powder: an FTIR study," *Langmuir* 26(4):2521-2527.
Minero, C. et al. (2000). "Photocatalytic Transformation of Organic Compunds in the Presence of Inorganic Anions. 1. Hydroxyl-Mediated and Direct Electron-Transfer Reactions of Phenol on a Titanium Dioxide-Fluoride System," *Langmuir* 16:2632-2641.
Minero, C. et al. (2000). "Photocatalytic Transformation of Organic Compounds in the Presence of Inorganic Ions. 2. Competitive Reactions of Phenol and Alcohols on a Titanium Dioxide-Fluoride System," *Langmuir* 16:8964-8972.
Ochiai, M. et al. (Oct. 21, 2011, e-published Sep. 15, 2011). "Oxidation of primary aliphatic and aromatic aldehydes with difluoro(aryl)-λ3-bromane," *Org Lett* 13(20):5568-5571.
Patton, M.S. et al. (Dec. 2008). "Levels of systemic metal ions in patients with intramedullary nails," *Acta Orthop* 79(6):820-825.
Ple, N. et al. (1998). "Functionalization by Metallation of Fluoropyrazine. Diazines XXI," *Tetrahedron* 54:4899-4912.
Prakash, G.K. et al. (Mar. 5, 2009). "Efficient nucleophilic fluoromethylation and subsequent transformation of alkyl and benzyl halides using fluorobis(phenylsulfonyl)methane," *Org Lett* 11(5):1127-1130.
Rodushkin, I. et al. (1999). "Multielement analysis of whole blood by high resolution inductively coupled plasman mass spectrometry," *Fresenius J Anal Chem* 364:338-346.
Sergeev, M.E. et al. (May 6, 2015, e-published Apr. 22, 2015). "Titania-catalyzed radiofluorination of tosylated precursors in highly aqueous medium," *J Am Chem Soc* 137(17):5686-5694.
Tang, P. et al. (Jun. 17, 2011). "Silver-mediated fluorination of aryl silanes," *Tetrahedron* 67(24):4449-4454.
Tang, P. et al. (Aug. 3, 2011, e-published Jul. 12, 2011). "Deoxyfluorination of phenols," *J Am Chem Soc* 133(30):11482-11484.
Written Opinion dated Sep. 30, 2015, for PCT Application No. PCT/US2015/039095, filed on Jul. 2, 2015, 4 pages.

METAL OXIDE CATALYZED RADIOFLUORINATION

STATEMENT AS TO RIGHTS TO INVENTIONS MADE UNDER FEDERALLY SPONSORED RESEARCH AND DEVELOPMENT

This invention was made with Government support under Grant Number EB015540, awarded by the National Institutes of Health. The Government has certain rights in the invention.

BACKGROUND OF THE INVENTION

Positron emission tomography (PET) is an extremely effective imaging tool in preclinical and clinical cancer research to visualize physiological state or changes in the living body, to investigate the mechanism of disease, and to quantify biological processes such as receptor occupancy, cell proliferation, metabolic activity, apoptosis, and gene expression. Since PET allows measurement of phenotypic changes associated with a malignant condition with high sensitivity, the onset of a particular disease such as cancer can be detected, diagnosed, and treated at an early stage prior to the development of metastasis. Typically, $^{18}$F-labeled PET tracers are synthesized using nucleophilic fluorination of activated precursors with $[^{18}O]H_2O/[^{18}F]$fluoride obtained from cyclotron. Due to high F-ion solvation energy, aqueous fluoride is inactive unless it is released from its aqueous surrounding. This is usually achieved by mixing aqueous fluoride with base ($KHCO_3$, $K_2CO_3$ etc.) and phase transfer agent (e.g., Kryptofix-222) and azeotropic drying of the resulting solution with acetonitrile. The dried active complex (e.g., $[^{18}F]KF/K_{222}$) is further used for radiolabelling. Depending on technical method of fluoride activation (i.e. microchip or macro-reactor evaporation, cartridge solvent exchange), this procedure takes 20-30 minutes and some loss of initial radioactivity is observed.[4,5]

To reduce the need for a lengthy drying process, there has been interest during the last years in the development of radiofluorination methods that allow to use aqueous $[^{18}F]$ fluoride directly without the traditional drying/azeotroping step. Several novel approaches were suggested, such as enzymatic and transition-metal catalysis, development of specific substrates and fluorinating reagents. The majority of methods which are directly using the cyclotron-delivered $[^{18}O]H_2O/[^{18}F]$fluoride leads to low-to-moderate fluoride conversion and yields of fluorinated product, while reactions are conducted in aqueous-organic medium with water content up to 20% and mostly these methods deal with aromatic nucleophilic fluorination. Titania is widely used in a variety of chemical processes, including electro- and photochemistry. Along with broad catalytic activity it possesses strong ability to adsorb water from the surrounding medium.

Provided herein, inter alia, is a conceptually new method based on titania as a catalyst. Embodiments include highly efficient and fast route for radiofluorination is suitable for aromatic, aliphatic and cycloaliphatic precursors in organic-aqueous medium with maximum tolerated water content up to 25%.

BRIEF SUMMARY OF THE INVENTION

Provided herein, inter alia, is a catalytic approach to carry out the synthesis in reaction medium with much higher water content (up to 25% water in the reaction mixture) than is normally possible with these precursors.

Typically, the source of fluorine-18 is a cyclotron (yielding [F-18]fluoride in [O-18]water). Therefore, the ability to perform reactions with high water content eliminates the need for the time-consuming preliminary steps of evaporative drying and azeotropic distillation (with MeCN) that is typically needed to remove water prior to the radiolabeling reaction.

Provided herein, inter alia, are basic, transition and rare-earth metal oxides as a catalyst for nucleophilic SN2-type radiofluorination reaction of organic substrates containing an active leaving group. Examples of leaving groups are benzenesulfonyl, 4-methylbenzenesulfonyl (tosylate), 4-nitrobenzenesulfonyl (nosylate), methanesulfonyl (mesylate), ethanesulfonyl, trifluoromethylsulfonyl (triflate), or 1,1,2,2,2-pentafluoroethane-1-sulfonyl.

The resulting radiolabeled molecules are useful, for example, as tracers for positron emission tomography (PET) in either research or clinical studies. The approach may also be useful in the field of fluorine chemistry to facilitate the production of fluorine-containing molecules such as pharmaceuticals.

Materials used include commercially available metal oxide catalysts (Sigma-Aldrich), $^{18}$F-fluoride (produced in UCLA Biomedical cyclotron), a few standard PET tracer precursors (ABX GmbH), commercially available solvents and reagents (Sigma-Aldrich).

Solutions containing a metal oxide catalyst and a precursor may be pre-incubated. Aqueous [F-18]fluoride containing a phase transfer agent may then be added. Finally, the mixture may be heated thereby performing the reaction.

Exemplary procedure (titanium dioxide catalyzed synthesis of $[^{18}F]$fallypride): Prior to use titanium dioxide was calcined at 550° C. during 12 h. A screw-cap scintillation vial was filled with $TiO_2$ (11.5 mg, 0.14 mmol) and tosyl-fallypride (2.3 µmol) solution in 1:1 mixture of acetonitrile and thexyl alcohol (30 µL). Vial was capped and incubated at room temperature for 1 hour. The aqueous solution of $[^{18}F]F^-/TBAHCO_3$ (1.5-3 mCi, 10 µl) was then added into pre-incubated vial, resulting into 25% water content in reaction mixture. The vial was capped and transferred to a Peltier heater. Reaction was performed at 130° C. for 5 minutes. The product was then extracted with methanol (2×200 µl). Combined extracts were thoroughly filtered through a Whatman 'Anotop 10 Plus' filter (0.02 µm) and the radiolabeled product content was analyzed by radio-TLC and HPLC.

For $TiO_2$ catalyst and the fallypride precursor, the reaction conditions may be 130° C. and 5 min reaction time with 25% water content, but the reaction can also be performed at temperature range of about 90° C. to about 140° C., time range of about 3 to about 10 minutes, water content range of about 5 to about 25%. Ranges might be extended with additional optimization, or with other precursors or other metal oxide catalysts.

BRIEF DESCRIPTION OF THE DRAWINGS

FIG. 3 is a series of graphs showing (left) radioactivity extraction and trapping at different catalyst loading amount. Triangles for radioactivity counted in organic extract, squares for radioactivity trapped in catalytic layer; (right) radiochemical purity of 2a.

DETAILED DESCRIPTION OF THE INVENTION

Figure 1:
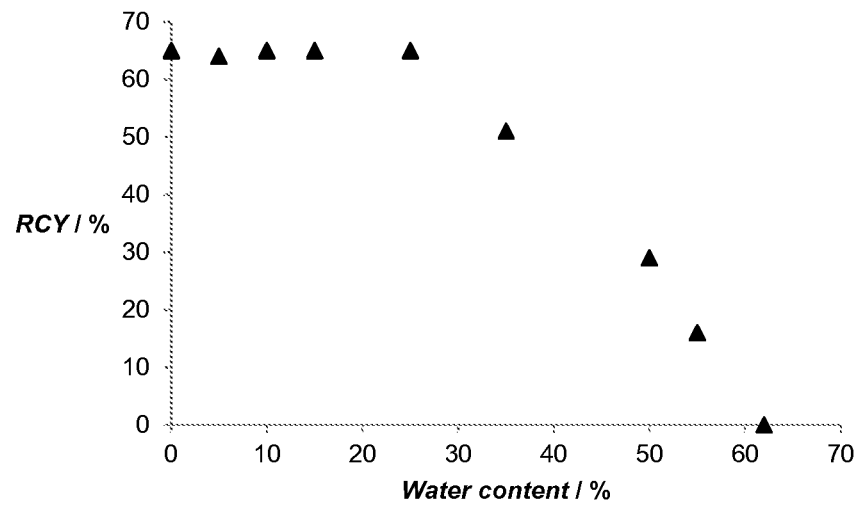
FIG. 1 is a graph showing the evaluation of water content in $TiO_2$-catalyzed radiofluorination of tosyl-fallypride.
Figure 2:
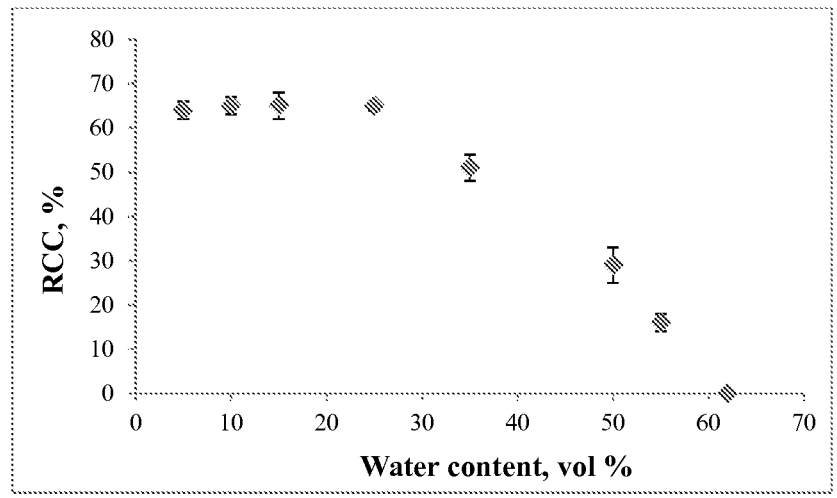
FIG. 2 is a graph showing the effect of water content on RCC in $TiO_2$-catalyzed radiofluorination of tosyl-fallypride.
Figure 3:
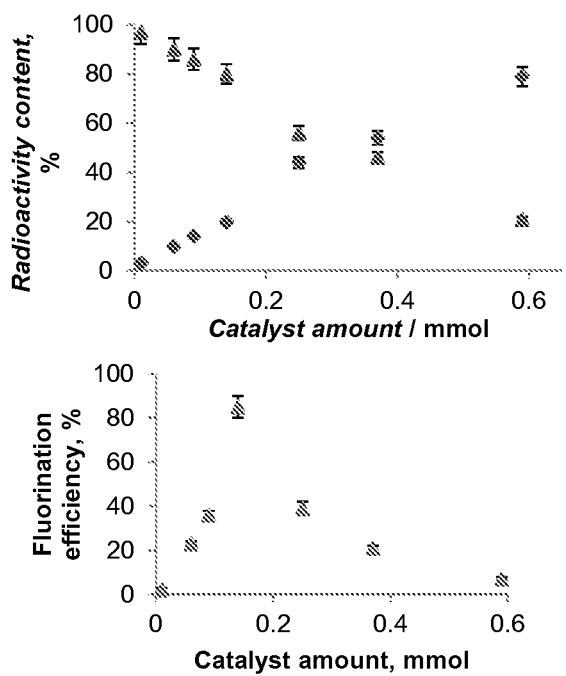
Figure 4:
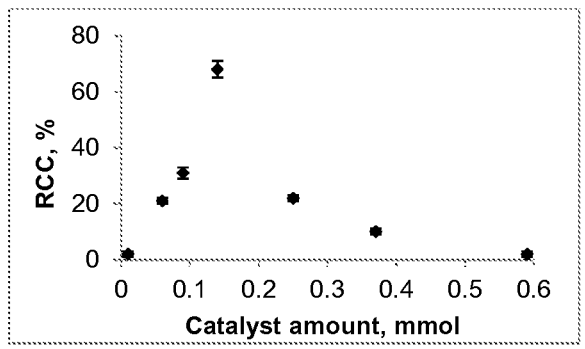
FIG. 4 is a graph showing the effects of catalyst loading amount on RCC.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH2O— is equivalent to —OCH2-.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R'', —OR', —SW, and/or —SO$_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, 0, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single bonded to carbon or to another sulfur.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SW, -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR—, —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A "reactive carbon," as used herein means, a carbon that is reactive with fluoride in the presence of the transition metal oxide.

In one aspect, a method is provided for forming an [$^{18}F$]-labeled organic compound in an aqueous medium. The method includes combining within an aqueous medium an aqueous [$^{18}F$] fluoride, a transition metal oxide and an organic compound precursor comprising a reactive carbon. An organic compound is a carbon containing compound (e.g. containing a substituted or unsubstituted alkyl, substituted or unsubstituted heteroalkyl, substituted or unsubstituted aryl, substituted or unsubstituted heteroaryl, substituted or unsubstituted cycloalkyl or substituted or unsubstituted heterocycloalkyl). An organic compound precursor is an organic compound that is utilized as a reactant in the methods provided herein to produce an [$^{18}F$]-labeled organic compound. In embodiments, the organic compound is less than about 1000 daltons. In embodiments, the organic compound is less than about 900 daltons. In embodiments, the organic compound is less than about 800 daltons. In embodiments, the organic compound is less than about 700 daltons. In embodiments, the organic compound is less than about 600 daltons. In embodiments, the organic compound is less than about 500 daltons. In embodiments, the organic compound is less than about 400 daltons. In embodiments, the organic molecule is a drug and/or modulator of a cellular process, such as a protein modulator (e.g. kinase inhibitor). The aqueous [$^{18}F$] fluoride source is allowed to react with the reactive carbon thereby forming said [$^{18}F$]-labeled organic compound. In embodiments, the organic compound precursor is an aryl organic compound precursor (i.e. an organic compound comprising a substituted or unsubstituted aryl moiety) and said [$^{18}F$]-labeled organic compound is an [$^{18}F$]-labeled aryl organic compound (i.e. an [$^{18}F$]-labeled organic compound comprising an substituted or unsubstituted aryl moiety).

The aqueous medium may be less than about 5%, 10%, 15%, 20%, 25%, 30%, 35%, 40%, 45%, 50%, 55%, 60%, 65%, 70%, 75%, 80%, 85%, 90%, or 95% water. In embodiments, the aqueous medium may be less than about 5%, 10%, 15%, 20%, 25%, 30%, 35%, 40%, 45%, 50%, 55%, 60%, 65%, 70%, 75% water. In embodiments, the aqueous medium may be less than about 5%, 10%, 15%, 20%, 25%, 30%, 35%, 40%, 45%, 50% water. In embodiments, the aqueous medium may be less than about 5%, 10%, 15%, 20% or 25% water. The [$^{18}F$]-labeled organic compound may be a positron emission tomography probe.

In embodiments, the reacting is SN2 nucleophilic substitution reaction The reactive carbon may form part of a substituted or unsubstituted aryl, substituted or unsubstituted heteroaryl, substituted or unsubstituted alkyl, substituted or unsubstituted heteroalkyl, substituted or unsubstituted cycloalkyl or substituted or unsubstituted heterocycloalkyl. In embodiments, the reactive carbon forms part of a substituted or unsubstituted alkyl, substituted or unsubstituted heteroalkyl, substituted or unsubstituted cycloalkyl or substituted or unsubstituted heterocycloalkyl.

The transition metal oxide may be chromium(VI) oxide, molybdenum(VI) oxide, platinum(IV) oxide, rhenium(VI) oxide, rhenium(VII) oxide, ruthenium(IV) oxide, tantalum (V) oxide, tin(IV) oxide, vanadium(IV) oxide, vanadium(V) oxide, yttrium(III) oxide, zirconium(IV) oxide, chromium (III) oxide, bismuth(III) oxide, manganese(IV) oxide, tungsten(IV) oxide, molybdenum(IV) oxide, tungsten(VI) oxide, palladium(II) oxide, iron(II) oxide, zinc(II) oxide, indium (III) oxide, copper(II) oxide, niobium(IV) oxide, niobium (V) oxide, or titanium(IV) oxide.

In embodiments, the transition metal oxide is palladium (II) oxide, iron(II) oxide, zinc(II) oxide, indium(III) oxide, copper(II) oxide, niobium(IV) oxide, niobium(V) oxide, or titanium(IV) oxide. The transition metal oxide may be $TiO_2$, $NbO_2$, $Nb_2O_5$, $In_2O_3$, or $CuO$.

The aqueous medium may further include a base. The aqueous medium may further include an ammonium base. In embodiments, the aqueous medium further comprises an ammonium bicarbonate base.

The aqueous medium further comprises an alcohol co-solvent, such as MeOH, EtOH, n-PrOH, i-PrOH, t-BuOH, tHexOH, n-octanol or cyclohexanol. The alcohol co-solvent may be t-BuOH, tHexOH, n-octanol or cyclohexanol.

The reactive compound or the organic compound precursor may be attached to a tosylate moiety. In embodiments, the reactive compound or the organic compound precursor is attached to a tosylate moiety. In embodiments, the compound or the organic compound precursor is attached to a benzenesulfonyl, 4-nitrobenzenesulfonyl (nosylate), methanesulfonyl (mesylate), ethanesulfonyl, trifluoromethylsulfonyl (triflate), or 1,1,2,2,2-pentafluoroethane-1-sulfonyl moiety.

In embodiments the method is based on titania (titanium dioxide, $TiO_2$) nanoparticles (crystalline composition: 45% rutile, 55% anatase; <200 nm size) as a catalyst. A nanoparticle is particle having a longest dimension less than about 1 μm (e.g. less than about 200, 300, 400, 500, 600, 700, 800 or 900 nm). The precursor solution is first incubated with the particles, and then a mixture of phase-transfer agent and $[^{18}F]$fluoride/$[^{18}O]H_2O$ (taken directly from cyclotron-delivered vial or trapped and eluted from QMA-cartridge) is added and reacted, followed by removal of the catalyst particles by filtration and then purification and reformulation steps. The use of $TiO_2$ obviates the laborious synthesis and purification of a metal-precursor complex prior to radiolabeling, and the method is compatible with many commercially-available or easily-synthesized precursors. We have demonstrated that this route for radiofluorination is suitable for aromatic, aliphatic, and cycloaliphatic precursors in organic-aqueous media with a tolerated water content up to 25 vol %.

Titania is widely used in a variety of chemical processes, including electro- and photochemistry. Along with broad catalytic activity, it possesses a strong ability to adsorb water from surrounding media. Numerous reports have demonstrated the mechanism of water dissociation at titania surface, and we hypothesize that this feature of $TiO_2$ might be used for in situ desolvation of $[^{18}F]$fluoride from water to catalyze nucleophilic radiofluorination reactions in organic-aqueous solutions without preliminary drying of the $[^{18}F]$ fluoride. We present an investigation of the influence of various reaction parameters on the radiofluorination of a model PET probe precursor and also discuss studies performed to further elucidate the mechanism of $TiO_2$-catalyzed radiofluorination.

EXAMPLES

General Information.

All the solvents and reagents were purchased from Sigma-Aldrich Chemical Co. (St. Louis, Mo.), except for Tetrabutylammonium bicarbonate (TBAB), 2,3-dimethoxy-5-[3-[[(4-methylphenyl)sulfonyl]oxy]propyl]-N-[[1-(2-propenyl-2-pyrrolidinyl)methyl] (tosyl-fallypride precursor), 1-(2,3-diacetyl-5-tosyl-(α-D-arabinofuranosyl)-2-nitroimidazole (FAZA precursor), N-Boc-trans-4-tosyloxy-L-proline methyl ester (trans-BTPME, cis-4-fluoroproline precursor) and the fallypride standard compound were purchased from ABX Advanced Biochemical Compounds (Radeberg, Germany).

No-carrier-added $[^{18}F]$fluoride ion was obtained from the UCLA Crump Institute for Molecular Imaging Cyclotron Facility by irradiation of 85% $^{18}O$-enriched water with an 11 MeV proton beam using an RDS-112 cyclotron (Siemens Medical Solution, Knoxville, Tenn.). Radioactivity was determined using a calibrated ion chamber (Capintec CRC-15R). A radioactive thin layer chromatography scanner (MiniGITA star) (Raytest USA, Inc, Wilmington, N.C.) and an analytical-scale high performance liquid chromatography (HPLC) system (Knauer, Germany) were used to analyze radiofluorination efficiency. The analytical-scale HPLC used for purification was equipped with a SecurityGuard C18 column (Phenomenex, Torrance, Calif.), a Phenomenex Luna reversed-phase C-18 column (250×4.6 mm), a variable wavelength UV detector and a radiometric detector (Eckert&Ziegler, Washington D.C., USA). TLC mobile phase: acetonitrile-water 50:50. HPLC mobile phase: acetonitrile-water 55:45.

Abbreviations

GCMS, gas-chromatography mass spectrometry; HPLC, high-performance liquid chromatography; ICP-MS, inductively-coupled plasma mass spectrometry; PET, positron-emission tomography; QC, quality control; REE: radioactivity extraction efficiency; RCC, radiochemical conversion; RCY, radiochemical yield; SA, specific activity; TBAB, tetra-n-butylammonium bicarbonate; TBAF, tetra-n-butylammonium fluoride; TLC, thin layer chromatography.

Example 1

As a model system for initial studies radiofluorination of tosyl-fallypride 1 to $[^{18}F]$fallypride 2, a highly specific radioligand for positron-emission tomography of $D_2/D_3$ brain striatum receptors used in animal PET imaging to study the brain conditions and functional malignancies was selected (M. R. Javed, S. Chen, J. Lei, J. Collins, M. Sergeev, H.-K. Kim, C.-J. Kim, R. M. van Dam, P. Y. Keng, *Chem. Comm.* 2014, 50, 1192-1194). The synthetic procedure includes tetrabutylammonium bicarbonate (TBAB), titania and 1:1 acetonitrile-thexyl alcohol solvent mixture (Scheme 1). Ammonium bicarbonate base was used instead of inorganic base/Cryptand due to its lower toxicity. According to Javed et al., (M. R. Javed, S. Chen, H.-K. Kim, L. Wei, J. Czernin, C.-J. Kim, R. M. van Dam, P. Y. Keng, *J. Nuc. Med.* 2013, 55, 1-8.) addition of thexyl alcohol is vital in fallypride radiosynthesis and improves fluorination efficiency two-fold, thus the same two-component organic medium was used. Experiments were performed at elevated temperature using a computer-controlled Peltier heating system. Fluorination efficiency was determined by radio-TLC and radio-HPLC. Identity of radiofluorinated product was confirmed by co-injection with [$^{19}$F]fallypride (ABX GmbH, Germany). Radiochemical conversions (RCCs) are presented as the mean of three runs.

Scheme 1. The catalytic radiofluorination of tosyl-fallypride.

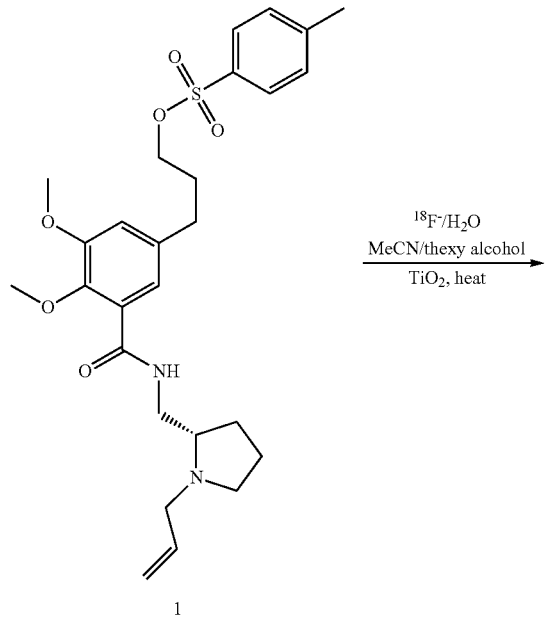

Scheme 1. The Catalytic Radiofluorination of Tosyl-Fallypride.

Example 2

Initial studies were performed to determine the necessity of base for TiO$_2$-catalyzed radiofluorination. Reactions were performed in acetonitrile-thexyl alcohol (MeCN-tHexOH) medium with or without base addition at 110° C. for 7 min, the typical conditions used in [$^{18}$F]fallypride syntheses (M. R. Javed, S. Chen, H.-K. Kim, L. Wei, J. Czernin, C.-J. Kim, R. M. van Dam, P. Y. Keng, *J. Nuc. Med.* 2013, 55, 1-8.). Radioactivity was introduced as 10 µl of [$^{18}$O]H$_2$O/[$^{18}$F] fluoride (typically 1.5-3 mCi). The amount of substrate 1 added was 2.3 µmol, and the total reaction volume was adjusted to 40 µl. Without base addition, the RCC was only 18%, but increased to 36% when TBAB was used. Base-fluoride coupling may still be needed, possibly due to better solubilization of in situ generated [$^{18}$F]TBAF than [$^{18}$F] fluoride in organic-aqueous medium. Also it was revealed that decay-corrected radioactivity recovery from the reaction vessel, which includes unreacted fluoride and fluorinated product, was less than 100%. After the reaction is done, the content of reaction vial is extracted with methanol (2*200 µl), and combined extracts contained only ~0.80% of initial radioactivity. Further efforts to make extraction more effective were not successful; thus we assumed some trapping of fluoride into the solid-phase. During further experiments the percentage of trapped fluoride remained remarkably constant at the level of ~20%. This loss is reflected in our reported RCCs, which we calculate as: RCC=[radioactivity recovery in organic extract]*[fluorinated product purity in organic extract]. Comparative experiments with dry [$^{18}$F]TBAF without titania at non-aqueous conditions led to 65% RCC; the 'dry' reaction with titania did not lead to fluoride conversion, organic extract contained neither fluorinated product nor parent [$^{18}$F]fluoride, and all the radioactivity was counted in the catalyst. This means that in non-aqueous medium TiO$_2$ addition results into total fluoride trapping, perhaps in the same manner as was previously reported for SiO$_2$ and Al$_2$O$_3$ (S. S. Tripathy, J.-L. Bersillon, K. Gopal, *Sep. Purif. Technol.* 2006, 50, 310-317). Efforts to label the precursor in organic-aqueous conditions without addition of titania failed, only unreacted fluoride was detected.

Example 3

In the next set of studies, optimization of reaction conditions was performed to determine tolerated water content (Table 1) and optimal catalyst-precursor ratio (Table 3). The water amount that leads to maximum [$^{18}$F]fallypride RCC was found to be <=25%, after which point a strong decrease in fluorination was observed. It was revealed that catalyst-precursor ratio plays important role not only in fluorination efficiency, but also affects the radioactivity extraction. The optimal ratio of TiO$_2$ to precursor is 61:1 for the catalyst particle size used.

Example 3.1: Evaluation of Water Content in Reaction Medium

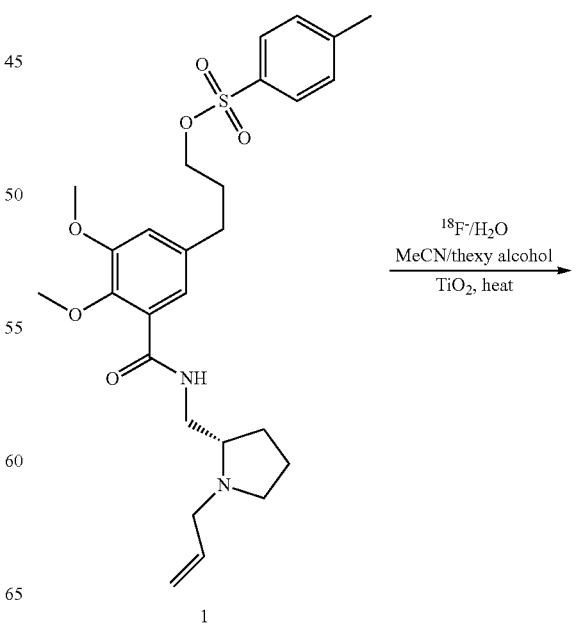

Example 3.1: Evaluation of Catalyst Loading

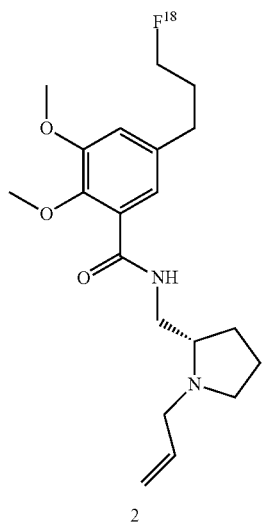

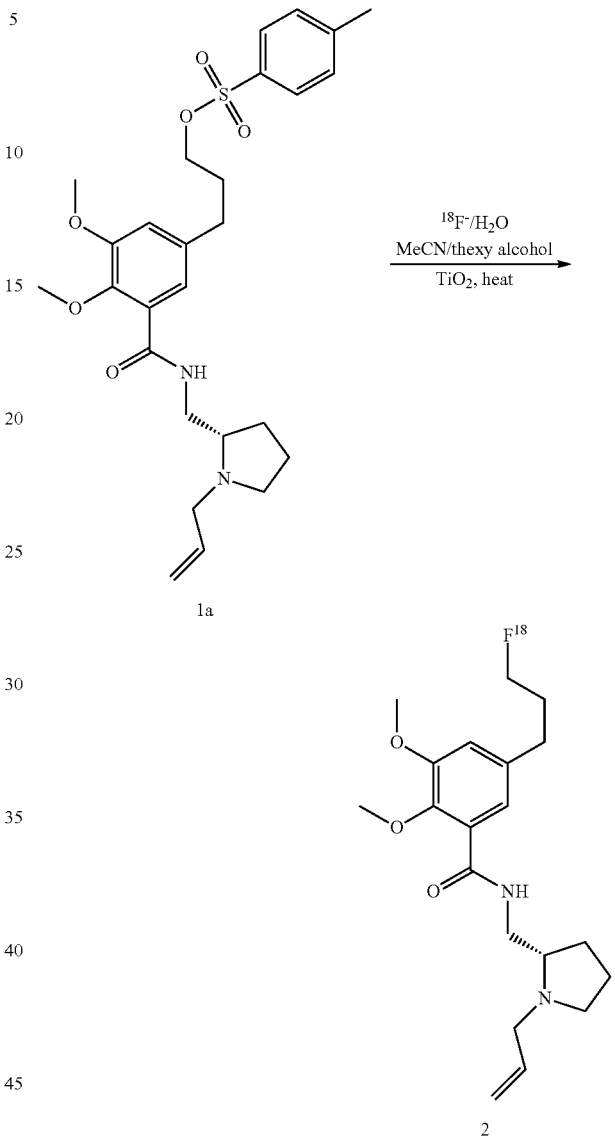

Procedure: A screw-cap scintillation vial (Fisherbrand #03-339-22A) was loaded with $TiO_2$ (0.14 mmol; crystalline composition: 45% rutile, 55% anatase; <200 nm size) and tosylated precursor 1a (2.3 µmol) solution in pre-determined amount (see Table 1) of 1:1 (v/v) mixture of acetonitrile (MeCN) and thexyl alcohol (tHexOH). The aqueous solution of [$^{18}$F]F$^-$/TBAB was prepared by mixing equal volumes of [$^{18}$O]H$_2$O/[$^{18}$F] and 75 mM aqueous solution of TBAB. A pre-determined volume (see Table 1) of this solution (containing 1.5-5 mCi radioactivity) was then added into reaction vial, resulting into 0-62% water content in reaction mixture. The vial was capped and transferred to computer-controlled Peltier heater. Reaction was performed at 110° C. for 7 minutes. The reaction mixture was mixed by refluxing solvent; no active magnetic stirring was used. After the reaction, the product was extracted with methanol (2×200 µL). Combined extracts were filtered through Whatman 'Anotop 10 Plus' filter (0.02 µm) and radiolabeled product content was analyzed by radio-TLC and HPLC.

TABLE 1

Effect of water content on RCC.

| Entry | ACN-tHexOH volume, [µL] | [$^{18}$F]/TBAB aq. volume, [µL] | Water content, [vol %] | Compound 2a purity in extract, [%] | RCC, [%] |
|---|---|---|---|---|---|
| 1[a] | 40 | 0 | 0 | 0 | 0 |
| 2 | 38 | 2 | 5 | 80 ± 2 | 64 ± 2 |
| 3 | 36 | 4 | 10 | 81 ± 2 | 65 ± 2 |
| 4 | 34 | 6 | 15 | 81 ± 2 | 65 ± 3 |
| 5 | 30 | 10 | 25 | 81 ± 3 | 65 ± 1 |
| 6 | 26 | 14 | 35 | 64 ± 4 | 51 ± 3 |
| 7 | 20 | 20 | 50 | 36 ± 5 | 29 ± 4 |
| 8 | 18 | 22 | 55 | 20 ± 4 | 16 ± 2 |
| 9 | 15.2 | 24.8 | 62 | 0 | 0 |

[a] [$^{18}$F]fluoride/TBAB complex was dried and reconstituted in anhydrous acetonitrile before addition.

It was found that the amount of catalyst added had a substantial effect on RCC. Studies with different catalyst amounts revealed that the optimal loading of $TiO_2$ is 140 µmol for 40 µl reaction volume with 25 vol % water content for the catalyst particle size used (<200 nm). This translates to ~60:1 ratio of catalyst to precursor 1 and enables production of target compound 2 with the highest RCC (78%). The RCC drops for both increasing and decreasing amounts of catalyst.

Procedure: A screw-cap scintillation vial was charged with $TiO_2$ (0.01-0.59 mmol) and tosylated precursor 1a (2.3 µmol) solution in 30 µl of 1:1 mixture of acetonitrile and thexyl alcohol. The aqueous solution of [$^{18}$F]F$^-$/TBAB was prepared by mixing equal volumes of [$^{18}$O]H$_2$O/[$^{18}$F] and 75 mM aqueous solution of TBAB. Aliquote of this solution (10 µl, containing 1.5-5 mCi radioactivity) was then added into reaction vial, resulting into 25% water content in reaction mixture. The vial was capped and transferred to computer-controlled Peltier heater. Reaction was performed at 110° C. for 7 minutes. After the reaction is done, the product was extracted with methanol (2×200 µl). Combined extracts were filtered through Whatman 'Anotop 10 Plus' filter (0.02 µm) and radiolabeled product content was analyzed by radio-TLC and HPLC.

Looking at fluorination efficiency, we observed catalyst amounts lower than the optimum to result in decreasing fluorination efficiency, perhaps due to reduced desolvation of fluoride. Surprisingly, increasing the amount of catalyst also decreased the fluorination efficiency. Perhaps as the catalyst amount is increased, one of the reaction components becomes depleted, reducing the interactions necessary for fluorination.

On the other hand, looking at extraction efficiency, we observed that REE decreases (i.e., trapping increases) with increasing amount of catalyst. Due to this linear relation, we suspect there are specific trapping sites for fluoride on the $TiO_2$, the number of which depends on the amount of catalyst present. Perhaps trapping occurs via exchange of fluoride with terminal hydroxyl groups (Minella, M.; Faga, M. G.; Maurino, V.; Minero, C.; Pelizzetti, E.; Coluccia, S.; Martra, G. *Langmuir* 2010, 26, 2521; Minero, C.; Mariella, G.; Maurino, V.; Pelizzetti, E. *Langmuir* 2000, 16, 2632; Minero, C.; Mariella, G.; Maurino, V.; Vione, D.; Pelizzetti, E. *Langmuir* 2000, 16, 8964). The consistent ~20% trapping for a fixed amount of catalyst may represent the equilibrium exchange between the surface and the reaction solution containing both fluoride and hydroxide ions. The case of 100% trapping under dry conditions (Table 3, entry 6), where the fluoride concentration dominates could represent a shift in this equilibrium (Habuda-Stanić, M.; Ravančić, M.; Flanagan, A. *Materials* 2014, 7, 6317).

Figure 19:
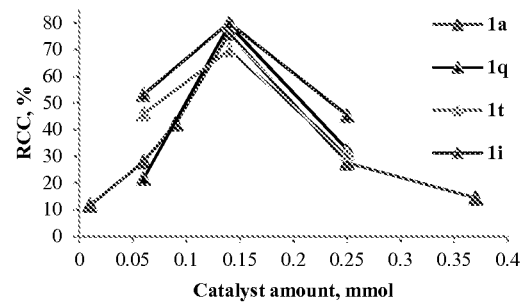
FIG. 19 is a series of graphs showing Determination of optimal catalyst amount for radiolabeling of 1a, 1i, 1q and 1t.
Figure 19:
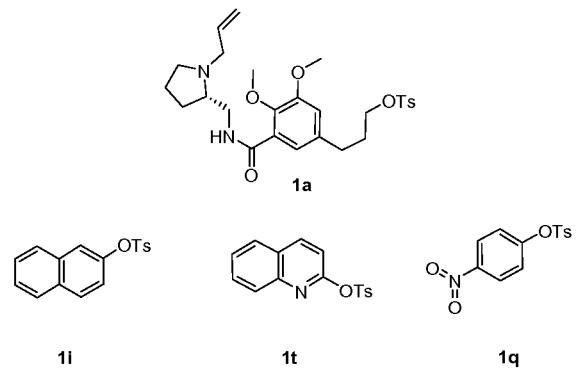
Figure 20:
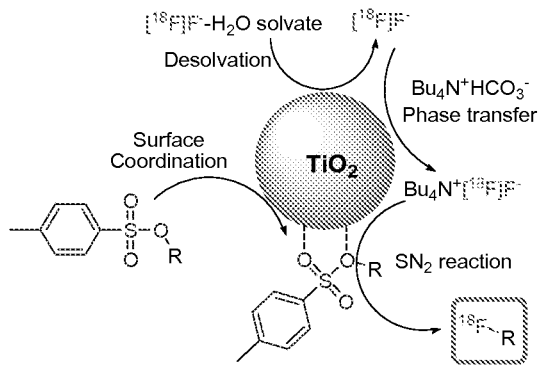
FIG. 20 is a picture showing a proposed mechanism for $TiO_2$-catalyzed radiofluorination. $SN_2$ substitution is improved with alcohol as a co-solvent, perhaps by inclusion in intermediate complex formation as determined by Oh et al.

To determine if the optimal amount of catalyst is universal or should be adjusted for every precursor, similar experiments were performed with substrates 1i, 1q and 1t. The loading of 140 µmol of $TiO_2$ remained optimal for these substrates as well (FIG. 19).

TABLE 3

Effect of catalyst loading on trapping and RCC.

| Entry | Catalyst, [mmol] | Compound 2 purity in extract, [%] | Extraction efficiency, [%] | [18F]-trapping, [%] | RCC, [%] |
|---|---|---|---|---|---|
| 1 | 0.01 | 2 ± 1 | 97 ± 2 | 3 ± 1 | 2 ± 1 |
| 2 | 0.06 | 23 ± 1 | 90 ± 2 | 10 ± 1 | 21 ± 1 |
| 3 | 0.09 | 36 ± 2 | 86 ± 2 | 14 ± 2 | 31 ± 2 |
| 4 | 0.14 | 85 ± 5 | 80 ± 2 | 20 ± 2 | 68 ± 3 |
| 5 | 0.25 | 39 ± 3 | 56 ± 2 | 44 ± 2 | 22 ± 1 |
| 6 | 0.37 | 21 ± 1 | 46 ± 2 | 54 ± 3 | 10 ± 1 |
| 7 | 0.59 | 7 ± 1 | 21 ± 2 | 79 ± 3 | 2 ± 1 |

Example 4

Optimal reaction time and temperature were determined as well. Maximum RCC of 78% was achieved at 130° C. with 10 min reaction time.

Example 4.1: Evaluation of Temperature Profile

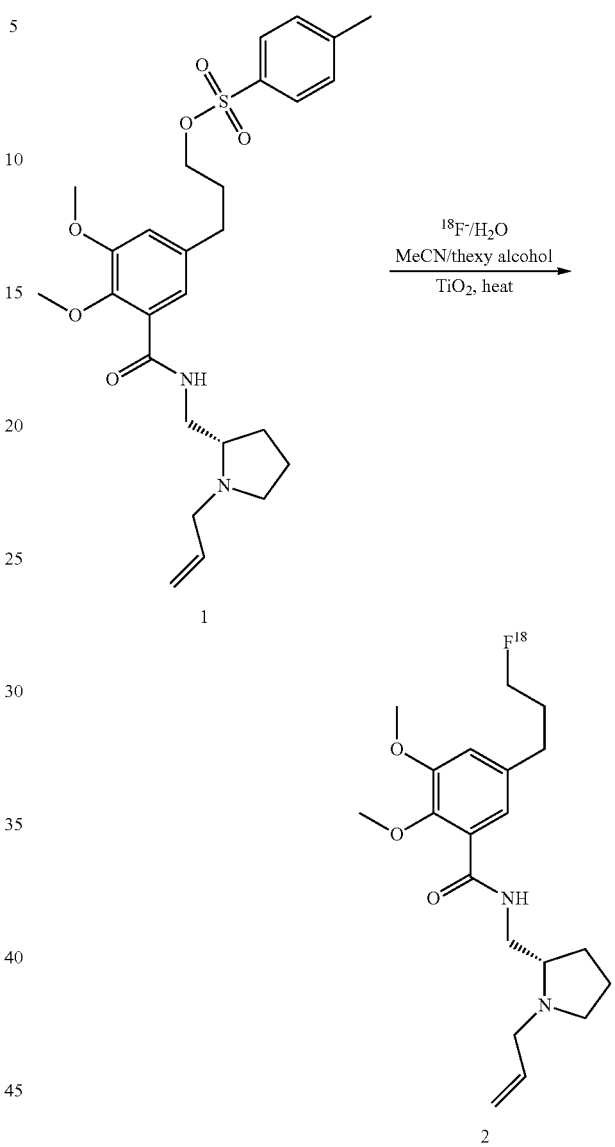

Procedure: A screw-cap scintillation vial was charged with $TiO_2$ (0.01-0.59 mmol) and tosylated precursor 1 (2.3 µmol) solution in 30 µl of 1:1 mixture of acetonitrile and thexyl alcohol. The aqueous solution of [$^{18}$F]F$^-$/TBAB was prepared by mixing equal volumes of [$^{18}$O]H$_2$O/[$^{18}$F] and 75 mM aqueous solution of TBAB. An aliquot of this solution (10 µl, containing 1.5-5 mCi radioactivity) was then added into reaction vial, resulting into 25% water content in reaction mixture. The vial was capped and transferred to computer-controlled Peltier heater. Reaction was performed at pre-determined temperature for 7 minutes. After the reaction is done, the product was extracted with methanol (2×200 µl). Combined extracts were filtered through Whatman 'Anotop 10 Plus' filter (0.02 µm) and radiolabeled product content was analyzed by radio-TLC and HPLC.

TABLE 4

Evaluation of temperature profile at 7 min reaction time.

| Entry | Temperature, [° C.] | Compound 2 purity in extract, [%] | RCC, [%] |
|---|---|---|---|
| 1 | 50 | 0 | 0 |
| 2 | 80 | 18 ± 3 | 24 ± 1 |
| 3 | 110 | 60 ± 2 | 65 ± 2 |
| 4 | 130 | 85 ± 1 | 68 ± 4 |
| 5 | 140 | 86 ± 1 | 69 ± 3 |
| 7 | 145 | 86 ± 2 | 68 ± 2 |

Example 4.1: Evaluation of Time Profile at 130° C.

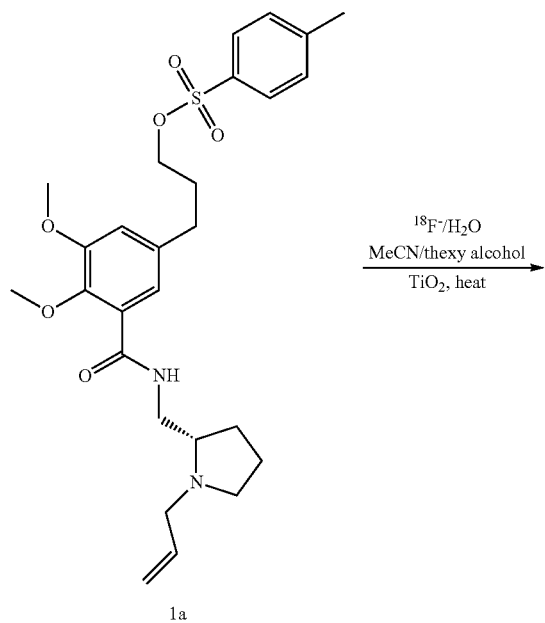

solution of [$^{18}$F]F$^-$/TBAB was prepared by mixing equal volumes of [$^{18}$O]H$_2$O/[$^{18}$F] and 75 mM aqueous solution of TBAB. An aliquot of this solution (10 μL, containing 1.5-5 mCi radioactivity) was then added into reaction vial, resulting into 25 vol % water content in reaction mixture. The vial was capped and transferred to computer-controlled Peltier heater. The reaction mixture was mixed by refluxing solvent; no active magnetic stirring was used. Reaction was performed at 130° C. for pre-determined time period. After the reaction, the product was extracted with methanol (2×200 μL). Combined extracts were filtered through Whatman 'Anotop 10 Plus' filter (0.02 μm) and radiolabeled product content was analyzed by radio-TLC and HPLC.

TABLE 5

Effect of reaction time on RCC. Reaction was performed at 130° C.

| Entry | Time, [min] | Compound 2 purity in extract, [%] | RCC, [%] |
|---|---|---|---|
| 1 | 2 | 70 ± 3 | 56 ± 2 |
| 2 | 4 | 76 ± 1 | 61 ± 1 |
| 3 | 6 | 84 ± 2 | 67 ± 2 |
| 4 | 7 | 85 ± 1 | 68 ± 1 |
| 5 | 8 | 86 ± 1 | 69 ± 3 |
| 6 | 10 | 97 ± 3 | 78 ± 3 |
| 7 | 12 | 96 ± 1 | 77 ± 2 |

Example 4.2: Evaluation of Substrate-Catalyst Incubation Time

Procedure: A screw-cap scintillation vial (Fisherbrand #03-339-22A) was loaded with TiO$_2$ (0.01-0.59 mmol) and tosylated precursor 1a (2.3 μmol) solution in 30 μL of 1:1 (v/v) mixture of acetonitrile and thexyl alcohol. The aqueous

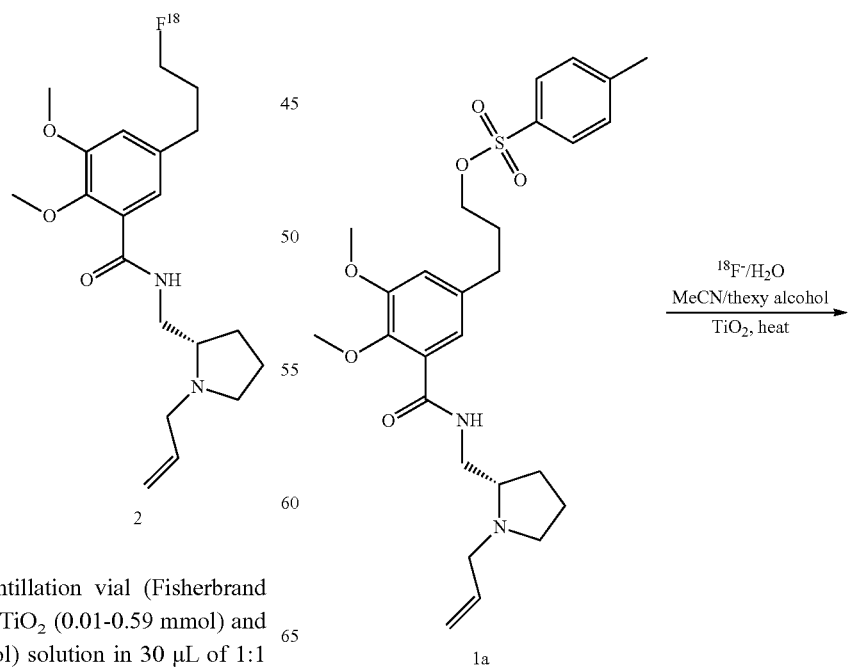

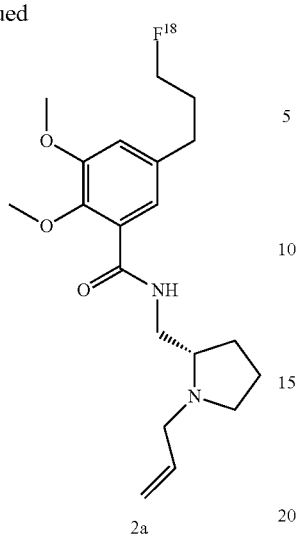

2a

Procedure: A screw-cap scintillation vial (Fisherbrand #03-339-22A) was loaded with $TiO_2$ (0.14 mmol) and tosylated precursor 1a (2.3 μmol) solution in 1:1 (v/v) mixture of acetonitrile and thexyl alcohol (30 μL). Vial was capped and incubated at room temperature for a pre-determined time period. The aqueous solution of $[^{18}F]F^-/TBAB$ was prepared by mixing equal volumes of $[^{18}O]H_2O/[^{18}F]$ and 75 mM aqueous solution of TBAB. An aliquot of this solution (10 μL, containing 1.5-5 mCi radioactivity) was then added into pre-incubated reaction vial, resulting into 25 vol % water content in reaction mixture. The vial was capped and transferred to computer-controlled Peltier heater. The reaction mixture was mixed by refluxing solvent; no active magnetic stirring was used. Reaction was performed at 130° C. for 10 minutes. After the reaction, the product was extracted with methanol (2×200 μL). Combined extracts were filtered through Whatman 'Anotop 10 Plus' filter (0.02 μm) and radiolabeled product content was analyzed by radio-TLC and HPLC.

TABLE 6

Evaluation of radiofluorination time profile after substrate-catalyst incubation.

| Entry | Time, [min] | Compound 2 purity in extract, [%] | RCC, [%] |
|---|---|---|---|
| 1 | 1 | 42 ± 3 | 34 ± 2 |
| 2 | 2 | 61 ± 1 | 49 ± 1 |
| 3 | 3 | 87 ± 2 | 70 ± 2 |
| 4 | 4 | 91 ± 1 | 73 ± 1 |
| 5 | 5 | 96 ± 1 | 78 ± 3 |
| 6 | 6 | 97 ± 2 | 78 ± 3 |
| 7 | 7 | 96 ± 2 | 78 ± 3 |
| 8 | 8 | 97 ± 2 | 78 ± 3 |
| 9 | 10 | 96 ± 2 | 78 ± 3 |
| 10 | 12 | 96 ± 2 | 78 ± 3 |

TABLE 7

Effect of substrate-catalyst incubation time on RCC.

| Entry | Time, [min] | Compound 2a purity in extract, [%] | RCC, [%] |
|---|---|---|---|
| 1 | 0 | 85 ± 3 | 68 ± 2 |
| 2 | 5 | 85 ± 1 | 68 ± 1 |
| 3 | 10 | 85 ± 1 | 68 ± 1 |
| 4 | 15 | 85 ± 2 | 68 ± 2 |
| 5 | 30 | 89 ± 1 | 71 ± 1 |
| 6 | 45 | 92 ± 1 | 74 ± 3 |
| 7 | 60 | 98 ± 3 | 78 ± 3 |
| 8 | 75 | 98 ± 3 | 78 ± 3 |
| 9 | 90 | 98 ± 1 | 78 ± 2 |

Example 4.3: Studies of Solvent Effects

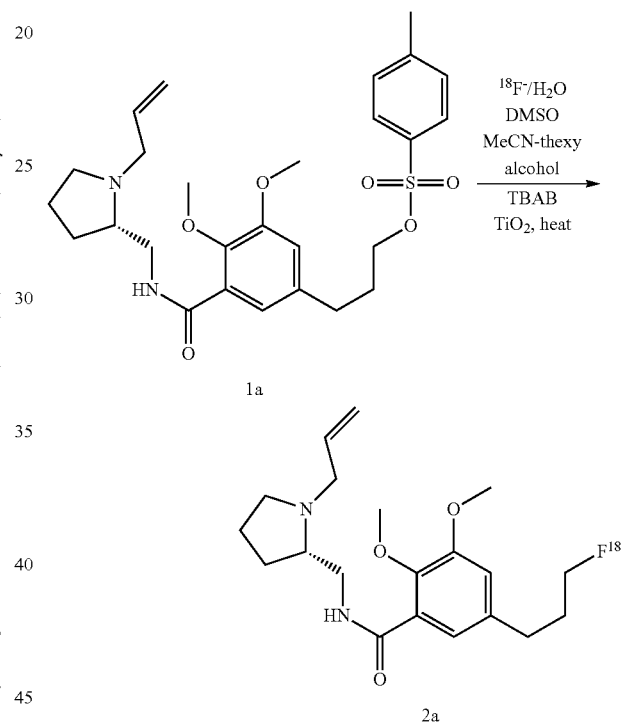

Procedure: A screw-cap scintillation vial (Fisherbrand #03-339-22A) was loaded with $TiO_2$ (0.14 mmol) and tosylated precursor 1a (2.3 μmol) solution in a mixture of acetonitrile and thexyl alcohol (30 μL), including varying amounts of DMSO (Table 8). Vial was capped and incubated at room temperature for 1 hour. The aqueous solution of $[^{18}F]F^-/TBAB$ was prepared by mixing equal volumes of $[^{18}O]H_2O/[^{18}F]$ and 75 mM aqueous solution of TBAB. An aliquot of this solution (10 μL, containing 1.5-5 mCi radioactivity) was then added into pre-incubated reaction vial, resulting into 25 vol % water content in reaction mixture. The vial was capped and transferred to pre-heated oil-bath. The reaction mixture was mixed by refluxing solvent; no active magnetic stirring was used. Reaction was performed at 130° C. for 5 min. After the reaction is done, the product was extracted with methanol (2×200 μL). Combined extracts were filtered through Whatman 'Anotop 10 Plus' filter (0.02 μm) and radiolabeled product content was analyzed by radio-TLC and HPLC.

TABLE 8

Effect of DMSO on extraction and RCC

| # | Precursor in ACN/tHexOH, uL | ACN/tHexOH, uL | DMSO, uL | DMSO, vol % | Compound 2a purity in extract, [%] | Extraction efficiency, % | RCC, % |
|---|---|---|---|---|---|---|---|
| 1[a] | 15 | 15 | 0 | 0 | 98 ± 1 | 79 ± 1 | 77 ± 2 |
| 2 | 15 | 13 | 2 | 5 | 87 ± 3 | 59 ± 3 | 30 ± 3 |
| 3 | 15 | 10 | 5 | 12.5 | 77 ± 2 | 34 ± 2 | 18 ± 3 |
| 4 | 15 | 5 | 10 | 25 | 66 ± 1 | 23 ± 4 | 9 ± 1 |
| 5 | 15 | 0 | 15 | 37.5 | 41 ± 4 | 13 ± 1 | 1.2 ± 1 |
| 6[b] | 0 | | 30 | 75 | 0 | 3 ± 2 | 0 |

[a]Standard experiment, reference point;
[b]precursor 1a was initially dissolved in DMSO.

Example 4.4: Evaluation of Time Profile for Radiofluorination with Pre-Incubation

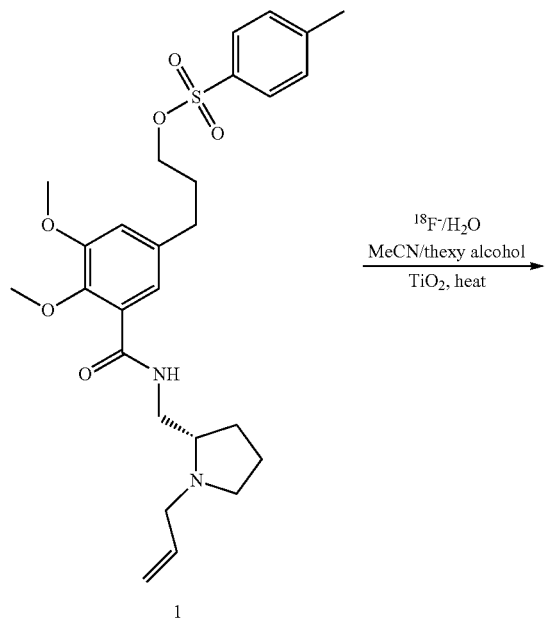

Procedure: A screw-cap scintillation vial was charged with $TiO_2$ (0.14 mmol) and tosylated precursor 1 (2.3 μmol) solution in 1:1 mixture of acetonitrile and alcohol (30 μL). Vial was capped and incubated at room temperature for 1 hour. The aqueous solution of [$^{18}$F]F$^-$/TBAB was prepared by mixing equal volumes of [$^{18}$O]H$_2$O/[$^{18}$F] and 75 mM aqueous solution of TBAB. Aliquot of this solution (10 μl, containing 1.5-5 mCi radioactivity) was then added into pre-incubated reaction vial, resulting into 25% water content in reaction mixture. The vial was capped and transferred to computer-controlled Peltier heater. Reaction was performed at 130° C. for pre-determine time-period. After the reaction is done, the product was extracted with methanol (2×200 μl). Combined extracts were filtered through Whatman 'Anotop 10 Plus' filter (0.02 μm) and radiolabeled product content was analyzed by radio-TLC and HPLC.

TABLE 9

Evaluation of radiofluorination time profile after substrate-catalyst incubation.

| Entry | Time, [min] | Compound 2 purity in extract, [%] | RCC, [%] |
|---|---|---|---|
| 1 | 1 | 42 ± 3 | 34 ± 2 |
| 2 | 2 | 61 ± 1 | 49 ± 1 |
| 3 | 3 | 87 ± 2 | 70 ± 2 |
| 4 | 4 | 91 ± 1 | 73 ± 1 |
| 5 | 5 | 96 ± 1 | 78 ± 3 |
| 6 | 6 | 97 ± 2 | 78 ± 3 |
| 7 | 7 | 96 ± 2 | 78 ± 3 |
| 8 | 8 | 97 ± 2 | 78 ± 3 |
| 9 | 10 | 96 ± 2 | 78 ± 3 |
| 10 | 12 | 96 ± 2 | 78 ± 3 |

Example 4.5: Evaluation of Optimal Reaction Conditions

To maximize fluorination efficiency of the precursor 1a, further evaluation of reaction conditions has been performed to determine optimal reaction parameters.

The range of water content that provided maximum RCC was found to be up to 25 vol %. In this aqueous range, the RCC and fluoride trapping remained remarkably constant. With higher water content, the trapping remained constant, but a strong decrease in [$^{18}$F]fluorination was observed. We hypothesize that higher water content exceeds the capacity of the catalyst to adsorb and split water, and thus the [$^{18}$F]fluoride is not as effectively desolvated, reducing the fluorination efficiency. If true, this suggests that increased catalyst amount may enable improved water tolerance if desired, but in light of results in the previous section, it would also be necessary to increase the precursor amount in the same proportion as the catalyst.

We also studied RCC as a function of reaction time and temperature, to determine the optimal reaction time (5 min) and temperature (130° C.). The influence of the specific type of alcohol co-solvent was evaluated as well. Several alcohols were tested in place of thexyl alcohol, but relatively little difference in RCC was observed. Thexyl alcohol showed the highest RCC of alcohols tested.

Example 5

Comparative runs with other common drying agents, $MgSO_4$ and $CaCl_2$, were also performed, but no fluoride conversion occurred (i.e. unreacted [$^{18}$F]fluoride was detected as the only radioactive component of reaction mixture), suggesting that the role of $TiO_2$ may not be merely water adsorption. Previous reports show that oxo-containing species readily coordinate on a $TiO_2$ surface through hydrogen bonding.[19,20] To explore the role of coordination in enhancing the reaction, the radiolabeling reaction was performed after incubation of tosylated substrate with catalyst. When preliminary incubation of precursor with titania was performed, significant decrease in reaction time was observed. RCC of ~70% was achieved in only 3 minutes and maximum radiolabeling efficiency was reached in 5 minutes (~77% RCC). Additional experiments on incubation time were also performed. It was revealed that enhancement in reaction time takes place only after at least 30 minutes of incubation and reaches maximum at 60 minutes. No further improvement in fluoride conversion was found after this point. These results suggest the following mechanism of catalyzed fluorination: the tosylated precursor binds to the catalyst through oxo-groups of sulfonyl moiety during incubation step; when aqueous [$^{18}$F]F$^-$/TBAB solution is added, aqueous solvate is adsorbed at active sites of titania in water-dissociative mode with [$^{18}$F]F$^-$ release; ammonium base serves as fluoride-trapping agent and subsequently conducts the phase-transfer of [$^{18}$F]F-ion to surface-coordinated precursor, where nucleophilic $SN_2$-type reaction occurs.

Example 6

The influence of different alcohols as co-solvents was also evaluated (Table 3). No significant difference either in radiolabeled product formation or in radioactivity extraction efficiency was found for different alcohols as co-solvents, but during the extraction step less swelling of oxide layer was observed for higher boiling and more dense alcohols (thexyl alcohol, cyclohexanol, n-octanol). In the case of smaller alcohols (methanol, ethanol), titania sticking to glass was the most extensive and the extraction process took longer time to achieve maximum radioactivity extraction. Also it was observed that alcohol structure does not influence the radioactivity extraction efficiency, which was found to be ~80% in all cases.

Example 6.1: Evaluation of Alcohol Co-Solvent Addition

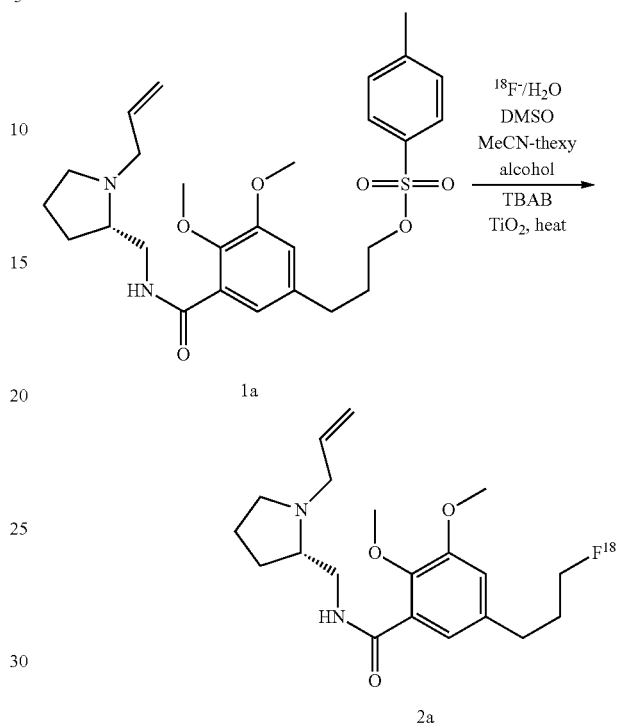

Procedure: A screw-cap scintillation vial (Fisherbrand #03-339-22A) was loaded with $TiO_2$ (0.14 mmol) and tosylated precursor 1a (2.3 µmol) solution in 1:1 (v/v) mixture of acetonitrile and alcohol (30 µL). Vial was capped and incubated at room temperature for 1 hour. The aqueous solution of [$^{18}$F]F$^-$/TBAB was prepared by mixing equal volumes of [$^{18}$O]H$_2$O/[$^{18}$F] and 75 mM aqueous solution of TBAB. An aliquot of this solution (10 µL, containing 1.5-5 mCi radioactivity) was then added into pre-incubated reaction vial, resulting into 25 vol % water content in reaction mixture. The vial was capped and transferred to computer-controlled Peltier heater. The reaction mixture was mixed by refluxing solvent; no active magnetic stirring was used. Reaction was performed at 130° C. for pre-determine time-period. After the reaction, the product was extracted with methanol (2×200 µL). Combined extracts were filtered through Whatman 'Anotop 10 Plus' filter (0.02 µm) and radiolabeled product content was analyzed by radio-TLC and HPLC.

TABLE 10

Evaluation of alcohol co-solvent.[a]

| Entry | Alcohol | Compound 2 purity in extract, [%] | RCC, [%] |
|---|---|---|---|
| 1 | — | 0 | 0 |
| 2 | MeOH | 76 ± 3 | 61 ± 3 |
| 3 | EtOH | 85 ± 4 | 68 ± 3 |
| 4 | n-PrOH | 92 ± 5 | 74 ± 4 |
| 5 | i-PrOH | 83 ± 3 | 66 ± 3 |
| 6 | t-BuOH | 80 ± 4 | 64 ± 3 |
| 7 | tHexOH | 97 ± 2 | 78 ± 2 |

TABLE 10-continued

Evaluation of alcohol co-solvent.[a]

| Entry | Alcohol | Compound 2 purity in extract, [%] | RCC, [%] |
|---|---|---|---|
| 8 | n-octanol | 82 ± 4 | 66 ± 3 |
| 9 | cyclohexanol | 95 ± 1 | 76 ± 1 |

[a]Reaction conditions: precursor 1 (2.3 µmol) in acetonitrile-alcohol (1:1 mixture, 30 µl), TiO$_2$ (0.14 mmol); [$^{18}$F]/TBAB aq. (10 µl), 130° C., 10 min.

Example 7

After establishing optimized reaction conditions, we next investigated the generality of catalytic radiofluorination of tosylated precursors. We synthesized a library of aromatic, aliphatic and cycloaliphatic tosylates and tested them in titania-catalyzed radiolabeling reactions along with commercially available tosylated precursors of PET probes. The reaction turned out to be highly efficient for low-molecular-weight precursors 3a-k (RCC ~80%), but resulted in low to moderate yields when bulky and sterically hindered compounds 3l-n with additional oxo-moieties were used. Perhaps lower yields in latter cases are due to precursor coordination at the catalyst surface through other oxo-groups instead of O=S=O moiety of tosyl, which results in increased distance between [$^{18}$F]F$^-$-ion at titania surface and the tosylate reactive center.

Example 7.1: General Procedure for the Synthesis of Tosylated Precursors 1B-u and 3a-k

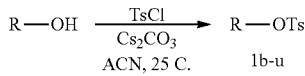

Tosylated precursors 1b-u were synthesized by general procedure of Pasha et al. (Reddy, M. B. M.; Pasha, M. A. *Phosphorus, Sulfur, Silicon Relat. Elem.* 2011, 186, 1867-1875; Kim, D.-Y.; Kim, H.-J.; Yu, K.-H.; Min, J.-J. *Bioconjugate Chem.* 2012, 23, 431-437).

To a solution of corresponding starting alcohol (1.9 mmol) in MeCN (10 mL) p-toluenesulfonyl chloride (2.2 mmol), and Cs$_2$CO$_3$ (1 mol %), were added. The reaction mixture was stirred rapidly at 25° C. for 10 h. The progress of the reaction was monitored by thin-layer chromatography (TLC). After completion of the reaction, the mixture was diluted with water (20 mL) and product was extracted with diethyl ether (20 mL). The organic extract was then washed with saturated solution of NaHCO$_3$ (2×10 mL), saline (2×10 mL) and water (10 mL). After drying over anhydrous Na$_2$SO$_4$, volatiles were evaporated under reduced pressure, residue was dissolved in a mixture of ethyl acetate:hexane 1:5 and purified via flash chromatography over silica gel. Structure identity was confirmed by $^1$H and $^{13}$C NMR spectroscopy, spectra were consistent with literature data. Purity was established by RP-HPLC with C18-column and a mixture of acetonitrile and water 55:45.

Precursors 1a, 1v, 1w and 1x were purchased from Advanced Biochemical Compounds (ABX GMBH, Radeberg, Germany). Tosylates 3a-k were prepared in an analogous fashion.

Example 7.2

General procedure for the synthesis of $^{19}$F-fluorinated standard compounds 4a-n-nonradioactive.

$^{19}$F-fluorinated standards for compounds 4a-n were synthesized by general procedure of Kim et al.

To a solution of corresponding starting tosylated 3a-n (1 mmol) in MeCN (5 mL) 1M TBAF solution in THF (2 mmol) was added. The reaction mixture was then heated at 85° C. for 4 h. Distilled water (10 ml) was added and the fluorinated product was extracted with diethyl ether (2*10 ml). Organic extract was washed with saturated solution of NaHCO$_3$ (2*5 ml), saline (2*5 ml) and water (5 ml). After dried over anhydrous Na$_2$SO$_4$ volatiles were evaporated under reduced pressure, residue was dissolved in a mixture of ethyl acetate:hexane 1:5 and purified via flash chromatography over silica gel. Structure identity was confirmed by $^1$H, $^{13}$C, and $^{19}$F NMR spectroscopy. Purity was established by RP-HPLC with C18-column and a mixture of acetonitrile and water 55:45.

TABLE 11

Substrate scope.[a]

| Entry | Substrate 3[b] | Product 4[c] | RCC [%] |
|---|---|---|---|
| a | phenyl-O-Ts | phenyl-$^{18}$F | 78 ± 3 |

TABLE 11-continued

Substrate scope.[a]

R—O—S(=O)(=O)—C6H4—CH3  →[18F/H2O, MeCN/thexyl alcohol, TBAHCO3 aq., TiO2, heat]  R—18F 3a-n → 4a-n

| Entry | Substrate 3[b] | Product 4[c] | RCC [%] |
|---|---|---|---|
| b | BnO-Ts | Bn-18F | 80 ± 3 |
| c | PhCH2CH2-O-Ts | PhCH2CH2-18F | 80 ± 2 |
| d | Ph(CH2)3-O-Ts | Ph(CH2)3-18F | 80 ± 2 |
| e | Ph(CH2)4-O-Ts | Ph(CH2)4-18F | 77 ± 4 |
| f | Ph(CH2)6-O-Ts | Ph(CH2)6-18F | 80 ± 1 |
| g | 1-naphthyl-O-Ts | 1-naphthyl-18F | 79 ± 2 |
| h | 2-naphthyl-O-Ts | 2-naphthyl-18F | 80 ± 1 |
| i | PhCH(CH3)-O-Ts | PhCH(CH3)-18F | 80 ± 2 |
| j | n-octyl-O-Ts | n-octyl-18F | 80 ± 1 |
| k | cyclohexyl-O-Ts | cyclohexyl-18F | 79 ± 1 |

TABLE 11-continued

Substrate scope.[a]

| Entry | Substrate 3[b] | Product 4[c] | RCC [%] |
|---|---|---|---|
| l | | | 70 ± 2 |
| m | | | 50 ± 4 |
| n | | | 26 ± 4 |

[a] Reaction conditions: precursor 3 (2.3 μmol) in acetonitrile-thexyl alcohol (1:1 mixture, 30 μl) pre-incubated with TiO$_2$ (0.14 mmol) for 1 h; [$^{18}$F]/TBAB aq. (10 μl), 130° C., 5 min. [b] Compounds 3a-k were synthesized according to Reddy et al. (Reddy, M. B. M.; Pasha, M. A. *Phosphorus, Sulfur, Silicon Relat. Elem.* 2011, 186, 1867-1875.), PET precursors 3l-m were purchased from ABX GmbH, Germany. [c] $^{19}$F-fluorinated cold standards 4a-n were synthesized by method of Kim et al. (Kim, D.-Y.; Kim, H.-J.; Yu, K.-H.; Min, J.-J. *Bioconjugate Chem.* 2012, 23, 431-437).

Example 7.3: General Procedure for Titania-Promoted $^{18}$F-Radiosynthesis of Compounds 4a-n

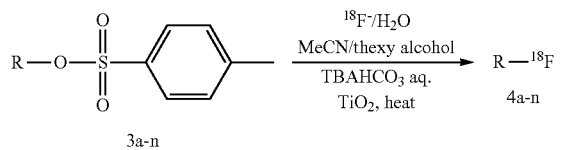

Prior to use titanium dioxide was calcined at 550° C. during 12 h.

A screw-cap scintillation vial was charged with TiO$_2$ (11.5 mg, 0.14 mmol) and tosylated precursor 3a-n (2.3 μmol) solution in 1:1 mixture of acetonitrile and thexyl alcohol (30 μL). Vial was capped and incubated at room temperature for 1 hour. The aqueous solution of [$^{18}$F]F$^-$/TBAHCO$_3$ (1.5-3 mCi, 10 μl) was then added into pre-incubated vial, resulting into 25% water content in reaction mixture. The vial was capped and transferred to Peltier heater. Reaction was performed at 130° C. for 5 minutes. After the reaction is done, the product was extracted with methanol (2×200 μl). Combined extracts were thoroughly filtered through Whatman 'Anotop 10 Plus' filter (0.02 μm) and radiolabeled product content was analyzed by radio-TLC and HPLC.

Example 7.4: Optimized General Procedure for Titania-Catalyzed $^{18}$F-Radiosynthesis of Compounds 2a-x

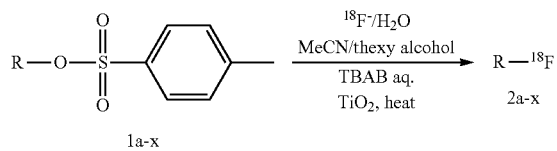

Prior to use titanium dioxide was calcined at 550° C. during 12 h.

A screw-cap scintillation vial (Fisherbrand #03-339-22A) was loaded with TiO$_2$ (11.5 mg, 0.14 mmol) and tosylated precursor 1a-x (2.3 µmol) solution in 1:1 v/v mixture of acetonitrile and thexyl alcohol (30 µL). Vial was capped and incubated at room temperature for 1 hour. The aqueous solution of [$^{18}$F]F$^-$/TBAB was prepared by mixing equal volumes of [$^{18}$O]H$_2$O/[$^{18}$F] and 75 mM aqueous solution of TBAB. The aqueous solution of [$^{18}$F]F$^-$/TBAHCO$_3$ (1.5-3 mCi, 10 µL) was then added into pre-incubated vial, resulting into 25 vol % water content in reaction mixture. The vial was capped and transferred to pre-heated oil bath. The reaction mixture was mixed by refluxing solvent; no active magnetic stirring was used. Reaction was performed at 130° C. for 5 minutes. After the reaction, the product was extracted with methanol (2×200 µL). Combined extracts were thoroughly filtered through Whatman 'Anotop 10 Plus' filter (0.02 µm) and radiolabeled product content was analyzed by radio-TLC and HPLC. Radiolabeled compound identity was established by co-injection with standard $^{19}$F-fluorinated compounds.

In conclusion, a method of TiO$_2$ catalyzed radiofluorination of tosylated precursors for preparation of [$^{18}$F]fluorine-labeled PET tracers was described. The suggested method features a simple protocol utilizing wet [$^{18}$F]fluoride in a mixture with ammonium base without preliminary drying-azeotroping step and in short reaction time. Nucleophilic [$^{18}$F]F-fluorination was shown to proceed in aqueous medium with up to 25% water content with excellent radiolabeling efficiency. The applicability of the reported protocol to a range of tosylated substrates was also demonstrated for organic molecules containing aromatic, aliphatic and cycloaliphatic moieties, and a plausible mechanism of action is also suggested. Although additional investigations are required to expand the scope and further understand the mechanism and improve performance, high radiofluorinating efficiency of this method may provide a versatile tool for practitioners in the field of PET radiochemistry.

Example 8

To demonstrate the overall radiochemical yield of isolated [$^{18}$F]Fallypride 2a, we performed full production runs (radiofluorination, HPLC purification, and formulation). The final formulated product was obtained as a sterile, injectable solution. During production, radioactivity measurements were recorded at key steps to assess efficiency of each process and identify potential areas for optimization (Table 12). The biggest loss is during extraction from the catalyst (20% trapped) and an additional ~10% is lost during our purification and formulation processes. Total production times, isolated yields and specific activities are compared to those previously reported in literature (Table 13). Generally, the isolated yield of titania-catalyzed reaction tends to be higher than reported for macroscale automated production, while it is comparable to microfluidic procedures, such as syntheses on a digital microfluidic chip (Javed, M. R.; Chen, S.; Lei, J.; Collins, J.; Sergeev, M.; Kim, H.-K.; Kim, C.-J.; Dam, R. M. van; Keng, P. Y. *Chem. Commun.* 2014, 50, 1192). or using the Advion Nanotek capillary reactor (Lu, S.; Giamis, A. M.; Pike, V. W. *Curr. Radiopharm.* 2009, 2, 1). By avoiding the need for fluoride drying/azeotroping, the synthesis process is simplified.

It is noteworthy to mention the high radiochemical purity of target compound 2a that formed during reaction. Only two radioactive peaks were detected by analytical HPLC, which consisted of unreacted [$^{18}$F]fluoride and the desired [$^{18}$F]Fallypride. Regarding HPLC analysis of the non-radioactive side products, the hydroxylated compound, resulting from hydrolysis, is clearly observed while no byproduct from β-elimination is apparent. With HPLC purification, the [$^{18}$F]fluoride and non-radioactive side products were effectively removed, and the reformulated solution was then examined by standard quality control (QC) tests (Keng, P. Y.; Chen, S.; Ding, H.; Sadeghi, S.; Shah, G. J.; Dooraghi, A.; Phelps, M. E.; Satyamurthy, N.; Chatziioannou, A. F.; Kim, C.-J.; van Dam, R. M. *Proc. Natl. Acad. Sci.* 2012, 109, 690). to evaluation its compliance with United States Food and Drug Administration requirements for injectable PET tracers (Table 14).

TABLE 12

Titania-catalyzed production of [$^{18}$F]Fallypride.[a]

| Parameter | Run 1 | Run 2 | Run 3 | Average |
|---|---|---|---|---|
| Initial activity, mCi | 5.20 | 5.19 | 5.23 | 5.20 ± 0.02 |
| REE, % | 79.1 | 81.2 | 81.9 | 80.7 ± 1.5 |
| RCC, % (non-isolated) | 79.1 | 81.2 | 81.5 | 80.6 ± 1.3 |
| Activity remaining after synthesis and extraction, %[b] | 79.1 | 81.2 | 81.9 | 80.7 ± 1.5 |
| Activity remaining after HPLC purification, %[b] | 75.7 | 76.5 | 77.6 | 76.6 ± 1.0 |
| Activity remaining after reformulation, %[b] | 71.2 | 68.6 | 73.2 | 71.0 ± 2.3 |
| Total loss, % | 28.8 | 31.4 | 26.8 | 28.9 ± 2.3 |
| Isolated RCY, % | 71.2 | 68.6 | 73.2 | 71.0 ± 2.3 |

[a]Optimized reaction conditions: 1 h pre-incubation time; 2.3 µmol of precursor; 140 µmol of TiO$_2$; 40 µl total reaction volume; no magnetic stirring; radioactivity introduced as 10 µl solution of aqueous [$^{18}$F]fluoride (~2.6 mCi) containing 0.36 µmol of TBAB; heated to 130° for 5 min using an oil bath. For each run, 2 vials are pooled after extraction to improve accuracy of measurements.
[b]Fractions of remaining radioactivity determined by measuring the radioactivity after the relevant step, correcting for decay, and dividing by the initial radioactivity.

TABLE 13

Comparison of catalytic production of 2a to known procedures.

| Entry | Reactor type | Radiolabeling conditions | Mean RCY, % | Total time, min |
|---|---|---|---|---|
| Moon et al., 2010[48] | Macroscale, automated. TracerLab FX | 100° C., 30 min | 68 | 74 |
| Pike et al.[46] | Microscale, automated. Nanotek Advion. | 150-190° C., 4-23 min | 16-88 | 50-218 |
| Javed et al.[7] | Microscale, automated. EWOD chip | 105° C., 7 min | 83 | 70 |
| Lazari et al.[49] | Macroscale automated. Elixys™ | 105° C., 7 min | 66 | 56[a] |
| Current report | Small-volume vial, manual | 130° C., 5 min | 71 | 50 |

[a] Total time reported without reformulation step

TABLE 14

Quality control tests of injectable [18F]Fallypride solution.

| Clinical QC test | Clinical acceptance criteria | Results of this study |
|---|---|---|
| Optical clarity | Clear and particle free | Clear and particle free |
| pH | 5.5-8.0 | 6.5 |
| Radiochemical purity | >95% | >99% |
| Radiochemical identity | Matches retention time of the standard | Matches retention time of the standard |
| $^{18}$F-radionuclide identity | Half-life 105-115 min | Half-life 111 min |
| Endotoxin level | <5 EU/mL | <1 EU/mL |
| Filter integrity | >50 psig | >100 psig |
| MeCN content | <410 ppm | <2 ppm |
| Thexyl alcohol content | <5000 ppm | <1 ppm |
| Sterility | No growth in 14 days | No growth in 14 days |
| Titanium content | None specified | 36 ± 4 ng |

With the introduction of the TiO$_2$ catalyst into the production procedure, an additional QC test to assess the titanium content in the reformulated solution may be needed. While the 20 nm filtration process and subsequent HPLC purification are expected to eliminate all particles, there is still the possibility of titanium ions in the final formulated solution. Using inductively-coupled plasma mass spectrometry (ICP-MS), the titanium content in representative samples was found to be 36±4 ng (n=9) of titanium per batch. Titanium is considered very inert and there do not appear to be established limits for titanium in injectable solutions. According to medicinal reports (Ipach, I.; Schäfer, R.; Mittag, F.; Leichtle, C.; Wolf, P.; Kluba, T. BMC Musculoskelet. Disord. 2012, 13, 159; Patton, M. S.; Lyon, T. D. B.; Ashcroft, G. P. Acta Orthop. 2008, 79, 820; Rodushkin, I.; Ödman, F.; Branth, S. Fresenius J. Anal. Chem. 1999, 364, 338), however, normal levels of titanium in human body range from 0 to ~20 µg/L blood (~0-100 µg per whole body of an adult) in patients without titanium implants, while reaching 100-150 ug/L blood (500-750 µg per whole body) in patients with artificial titanium joints. Thus, an injection of formulated [$^{18}$F]Fallypride produced by our method would have a very miniscule impact because it contains orders of magnitude less titanium than normally present in the blood. This could suggest that routine titanium testing may not be needed for every batch of injectable PET probe (Shao, X.; Schnau, P. L.; Fawaz, M. V.; Scott, P. J. H. Nucl. Med. Biol. 2013, 40, 109; Radiopharmaceuticals for Position Emission Tomography—Compounding. U.S. Pharmacopeial Convention, Chapter 823, USP 35-NF 50. 2012; pp 398-406).

We have, therefore, demonstrated the practical feasibility of the newly developed synthetic approach to the synthesis of a clinically-relevant PET probe, including compliance with FDA requirements for injectable solutions in clinical applications. By varying the precursor, other [$^{18}$F]fluorine-labeled PET probes could be produced by this procedure and similar QC results would be expected.

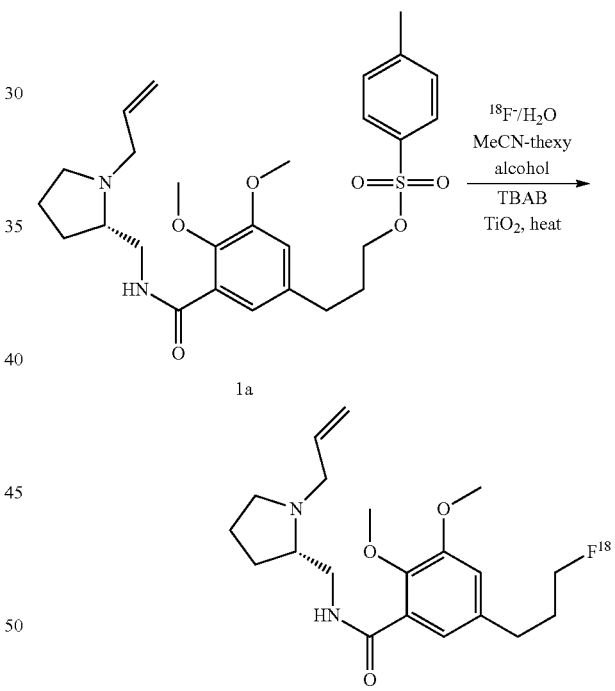

Procedure: Six screw-cap scintillation vials (Fisherbrand #03-339-22A) were loaded with TiO$_2$ (0.14 mmol) and tosylated precursor 1a (2.3 µmol) solution in 30 µl of 1:1 (v/v) mixture of acetonitrile and thexyl alcohol. The aqueous solution of [$^{18}$F]F$^-$/TBAB was prepared by mixing equal volumes of [$^{18}$O]H$_2$O/[$^{18}$F] and 75 mM aqueous solution of TBAB. 10 µl of this solution (containing 2.6 mCi radioactivity) was then added into each reaction vial, resulting into 25 vol % water content in reaction mixture. The vials were capped and transferred to pre-heated oil bath. The reaction mixture was mixed by refluxing solvent; no active magnetic stirring was used. Reaction was performed at 130° C. for 5 minutes. After the reaction is done, the product from each vial was extracted with methanol (2×200 μL). For statistical purposes, pairs of organic extracts were combined, giving 3 portions, each containing 800 μL of organic extract.

Purification/reformulation process: Each combined organic extract (800 μL) was evaporated under stream of nitrogen in plastic Eppendorf® tube using oil bath. Residue was reconstituted in 90 μL of HPLC buffer (55:45 v/v MeCN/aq. ammonium formate+1% triethylamine) and purified via HPLC (Phenomenex Luna reversed-phase C-18 column (250×4.6 mm)), collecting peak at 12 min. Collected fraction (~2 ml) was evaporated under stream of nitrogen in plastic Eppendorf® tube using oil bath. Residue was reconstituted in DPBS buffer and sterile filtered into sterile vial using Whatman Anotop 10 Plus sterile filter (0.2 μm). Resulting injectable solution underwent usual set of QC tests, including determination of endotoxin level, sterility, GCMS determination of residual solvents and ICP-MS determination of titanium content. HPLC chromatogram of final injectable solution and results of QC tests are shown below.

TABLE 15

Quality control tests of injectable [$^{18}$F]Fallypride solution.

| Clinical QC test | Clinical acceptance criteria | Results of this study |
| --- | --- | --- |
| Optical clarity | Clear and particle free | Clear and particle free |
| pH | 5.5-8.0 | 6.5 |
| Radiochemical purity | >95% | >99% |
| Radiochemical identity | Matches retention time of the standard | Matches retention time of the standard |
| $^{18}$F-radionuclide identity | Half-life 105-115 min | Half-life 111 min |
| Endotoxin level | <5 EU/mL | <1 EU/mL |
| Filter integrity | >50 psig | >100 psig |
| MeCN content | <410 ppm | <2 ppm |
| Thexyl alcohol content | <5000 ppm | <1 ppm |
| Sterility | No growth in 14 days | No growth in 14 days |
| Titanium content | None specified | 36 ± 4 ng |

Javed, M. R.; Chen, S.; Lei, J.; Collins, J.; Sergeev, M.; Kim, H.-K.; Kim, C.-J.; Dam, R. M. van; Keng, P. Y. *Chem. Commun.* 2014, 50, 1192.

Example 8.1: Characterization of Tosylate Precursors

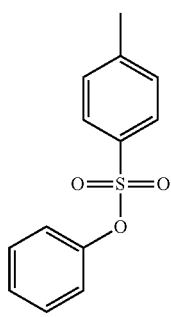 [SMILES: Cc1ccc(S(=O)(=O)Oc2ccccc2)cc1]

Phenyl p-toluenesulfonate (1b)

$^{1}$H NMR (400 MHz, CDCl$_3$, ppm) δ 7.9-8.0 (d, 2H), 7.4 (d, J=8.1 Hz, 2H), 7.2-7.3 (m, 2H), 6.9-7.0 (m, 1H), 6.8-6.9 (m, 2H), 2.5 (s, 3H); $^{13}$C NMR (100 MHz, CDCl$_3$, ppm) δ 155.4, 146.8, 141.6, 130.2, 129.6, 127.0, 120.8, 115.3, 21.8.

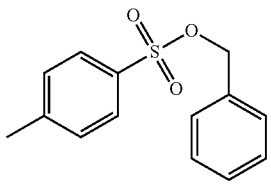 [SMILES: Cc1ccc(S(=O)(=O)OCc2ccccc2)cc1]

Benzyl p-Toluenesulfonate (1c)

$^{1}$H NMR (400 MHz, CDCl$_3$, ppm) δ 7.91-7.96 (d, 2H), 7.39-7.44 (d, 2H), 7.38 (d, J=4.65 Hz, 4H), 7.28-7.34 (m, 1H), 4.70 (s, 2H), 2.50 (s, 3H); $^{13}$C NMR (100 MHz, CDCl$_3$, ppm) δ 146.8, 141.7, 140.8, 130.2, 128.5, 127.6, 127.0, 126.9, 65.3, 21.8

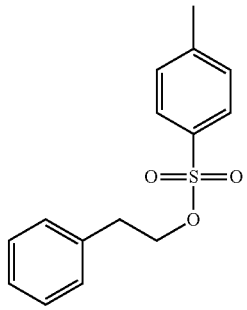 [SMILES: Cc1ccc(S(=O)(=O)OCCc2ccccc2)cc1]

2-Phenylethyl p-toluenesulfonate (1d)

$^{1}$H NMR (400 MHz, CDCl$_3$, ppm) δ 7.91-7.97 (d, 2H), 7.39-7.45 (d, 2H), 7.30-7.36 (m, 2H), 7.21-7.28 (m, 3H), 3.87 (t, J=6.60 Hz, 2H), 2.88 (t, J=6.60 Hz, 2H), 2.50 (s, 3H; $^{13}$C NMR (100 MH, CDCl$_3$, ppm) δ 146.8, 141.7, 138.4, 130.2, 129.0, 128.5, 127.0, 126.4, 63.6, 39.2, 21.8.

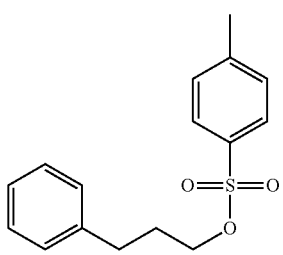 [SMILES: Cc1ccc(S(=O)(=O)OCCCc2ccccc2)cc1]

3-Phenylpropyl p-toluenesulfonate (1e)

$^{1}$H NMR (400 MHz, CDCl$_3$, ppm) δ 7.91-7.97 (d, 2H), 7.39-7.44 (d, 2H), 7.27-7.33 (m, 2H), 7.17-7.24 (m, 3H), 3.69 (t, J=6.36 Hz, 2H), 2.69-2.76 (m, 2H), 2.50 (s, 3H), 1.86-1.96 (m, 2H; $^{13}$C NMR (100 MHz, CDCl$_3$, ppm) δ 146.8, 141.8, 130.2, 128.4, 128.3, 127.0, 125.8, 62.2, 34.2, 32.0, 21.8.

2H), 7.35 (ddd, J=1.22, 6.91, 8.25 Hz, 1H), 7.09-7.18 (m, 2H), 2.49 (s, 3H); $^{13}$C NMR (100 MHz, CDCl$_3$, ppm) δ 153.3, 146.8, 141.6, 134.6, 130.2, 129.8, 128.9, 127.7, 127.0, 126.5, 126.3, 123.6, 117.7, 109.5, 21.8.

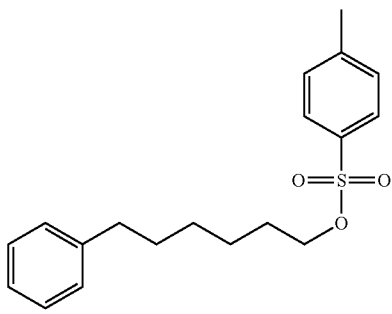 [SMILES: Cc1ccc(S(=O)(=O)OCCCCCCc2ccccc2)cc1]

6-Phenylhexyl p-toluenesulfonate (1g)

$^1$H NMR (400 MHz, CDCl$_3$, ppm) δ 7.90-7.97 (d, 2H), 7.39-7.45 (d, 2H), 7.25-7.32 (m, 2H), 7.15-7.22 (m, 3H), 3.64 (t, J=6.60 Hz, 2H), 2.58-2.67 (m, 2H), 2.50 (s, 3H), 1.53-1.73 (m, 4H), 1.30-1.45 (m, 4H); $^{13}$C NMR (100 MHz, CDCl$_3$, ppm) δ 146.8, 142.7, 141.7, 130.2, 128.3, 128.2, 127.0, 125.6, 62.9, 35.8, 32.6, 31.4, 29.0, 25.6, 21.8.

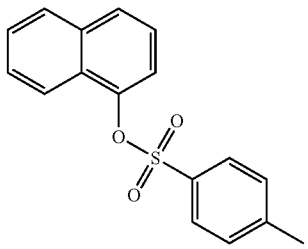 [SMILES: Cc1ccc(S(=O)(=O)Oc2cccc3ccccc23)cc1]

Naphth-1-yl p-toluenesulfonate (1h)

$^1$H NMR (400 MHz, CDCl$_3$, ppm) δ 8.18-8.24 (m, 1H), 7.91-7.97 (d, 2H), 7.80-7.87 (m, 1H), 7.49-7.54 (m, 2H), 7.46 (d, J=8.31 Hz, 1H), 7.38-7.43 (d, 2H), 7.33 (dd, J=7.46, 8.19 Hz, 1H), 6.84 (dd, J=0.98, 7.58 Hz, 1H), 2.49 (s, 3H); $^{13}$C NMR (100 MHz, CDCl$_3$, ppm) δ 151.3, 146.8, 141.6, 134.7, 130.2, 127.6, 127.0, 126.4, 125.8, 125.2, 124.3, 121.5, 120.6, 108.6, 21.8, 15.

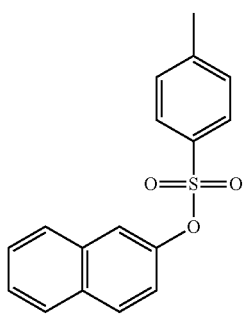 [SMILES: Cc1ccc(S(=O)(=O)Oc2ccc3ccccc3c2)cc1]

Naphth-2-yl p-toluenesulfonate (1i)

$^1$H NMR (400 MHz, CDCl$_3$, ppm) δ 7.91-7.97 (d, 2H), 7.74-7.81 (m, 2H), 7.69 (dd, J=0.61, 8.19 Hz, 1H), 7.45 (ddd, J=1.22, 6.91, 8.25 Hz, 1H), 7.41 (d, J=0.61, 8.68 Hz,

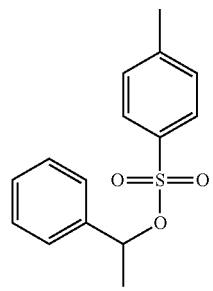 [SMILES: Cc1ccc(S(=O)(=O)OC(C)c2ccccc2)cc1]

1-Phenylethyl p-toluenesulfonate (1j)

$^1$H NMR (400 MHz, CDCl$_3$, ppm) δ 7.90-7.95 (d, 2H), 7.39-7.44 (d, 2H), 7.33-7.39 (m, 4H), 7.24-7.31 (m, 1H), 4.90 (q, J=6.36 Hz, 1H), 2.50 (s, 3H), 1.50 (d, J=6.60 Hz, 3H); $^{13}$C NMR (100 MHz, CDCl$_3$, ppm) δ

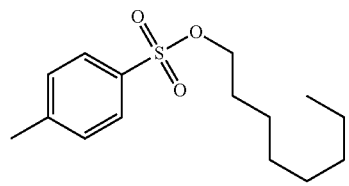 [SMILES: CCCCCCCCOS(=O)(=O)c1ccc(C)cc1]

Octyl p-toluenesulfonate (1k)

$^1$H NMR (400 MHz, CDCl$_3$, ppm) δ 7.90-7.95 (d, 2H), 7.38-7.44 (d, 2H), 3.64 (t, J=6.60 Hz, 2H), 2.50 (s, 3H), 1.52-1.62 (m, 2H), 1.21-1.40 (m, 10H), 0.85-0.92 (m, 3H); $^{13}$C NMR (100 MHz, CDCl$_3$, ppm) δ 146.8, 141.7, 130.2, 127.0, 63.0, 32.8, 31.8, 29.4, 29.2, 25.7, 22.6, 21.8, 14.1.

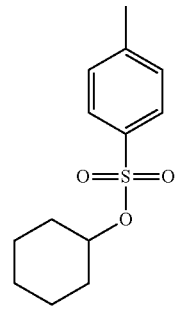

Cyclohexyl p-toluenesulfonate (1l)

$^1$H NMR (400 MHz, CDCl$_3$, ppm) δ 7.87-7.97 (d, 2H), 7.41 (d, J=8.07 Hz, 2H), 3.60 (td, J=4.68, 8.99 Hz, 1H), 2.49 (s, 3H), 1.46-1.98 (m, 5H), 1.06-1.36 (m, 5H); $^{13}$C NMR (100 MHz, CDCl$_3$, ppm) δ 146.8, 141.7, 130.2, 127.0, 114.9, 70.3, 35.5, 25.4, 24.1, 21.

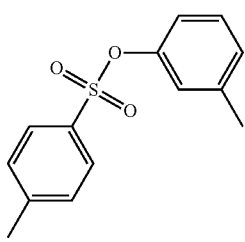 [SMILES: Cc1ccc(S(=O)(=O)Oc2cccc(C)c2)cc1]

m-cresyl p-toluenesulfonate (1n)

¹H NMR (400 MHz, CDCl₃, ppm) δ 7.67-7.77 (m, 2H), 7.32 (d, J=8.07 Hz, 2H), 7.10-7.18 (m, 1H), 7.05 (d, J=7.58 Hz, 1H), 6.87 (s, 1H), 6.66-6.76 (m, 1H), 2.46 (s, 3H), 2.30 (s, 3H); ¹³C NMR (100 MHz, CDCl₃, ppm) δ 149.9, 145.5, 140.3, 132.9, 130.0, 129.5, 128.8, 128.1, 123.3, 119.4, 77.6, 77.3, 22.0, 21.5.

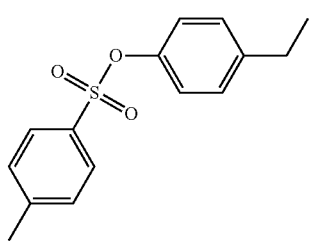 [SMILES: CCc1ccc(OS(=O)(=O)c2ccc(C)cc2)cc1]

p-ethylphenyl p-toluenesulfonate (1o)

¹H NMR (400 MHz, CDCl₃, ppm) δ 7.64-7.77 (m, 2H), 7.25-7.36 (m, 2H), 7.02-7.14 (m, 2H), 6.82-6.94 (m, 2H), 2.61 (q, J=7.58 Hz, 2H), 2.45 (s, 3H), 1.21 (t, J=7.58 Hz, 3H); ¹³C NMR (100 MHz, CDCl₃, ppm) δ 147.6, 145.2, 143.1, 132.6, 129.7, 128.8, 128.5, 122.1, 77.3, 76.7, 28.2, 21.7, 15.3.

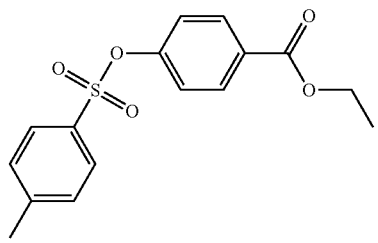 [SMILES: CCOC(=O)c1ccc(OS(=O)(=O)c2ccc(C)cc2)cc1]

p-ethoxycarbonylphenyl p-toluenesulfonate (1p)

¹H NMR (400 MHz, CDCl₃, ppm) δ 7.91-8.06 (m, 2H), 7.63-7.76 (m, 2H), 7.32 (dd, J=0.49, 8.56 Hz, 2H), 7.01-7.12 (m, 2H), 4.36 (q, J=7.09 Hz, 2H), 2.45 (s, 3H), 1.38 (t, J=7.21 Hz, 3H); ¹³C NMR (100 MHz, CDCl₃, ppm) δ 165.5, 152.9, 145.7, 132.1, 131.3, 129.9, 129.3, 128.5, 122.3, 115.0, 77.4, 77.0, 76.7, 61.3, 21.8, 14.3.

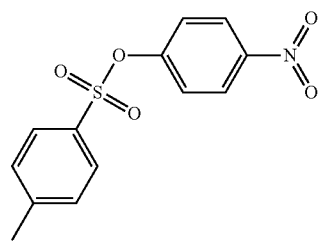 [SMILES: Cc1ccc(S(=O)(=O)Oc2ccc([N+](=O)[O-])cc2)cc1]

p-nitrophenyl p-toluenesulfonate (1q)

¹H NMR (400 MHz, CDCl₃, ppm) δ 8.10-8.25 (m, 2H), 7.65-7.79 (m, 2H), 7.36 (d, J=8.07 Hz, 2H), 7.13-7.23 (m, 2H), 2.48 (s, 3H); ¹³C NMR (100 MHz, CDCl₃, ppm) δ 153.6, 145.9, 131.4, 129.8, 128.2, 125.1, 122.9, 76.7, 76.4, 21.4.

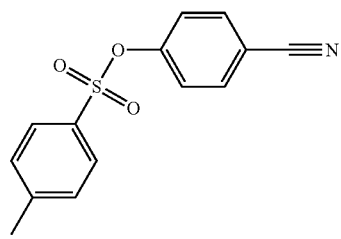 [SMILES: Cc1ccc(S(=O)(=O)Oc2ccc(C#N)cc2)cc1]

p-cyanophenyl p-toluenesulfonate (1r)

¹H NMR (400 MHz, CDCl₃, ppm) δ 7.68-7.78 (m, 2H), 7.57-7.66 (m, 2H), 7.35 (d, J=8.07 Hz, 2H), 7.08-7.20 (m, 2H), 2.47 (s, 3H); ¹³C NMR (100 MHz, CDCl₃, ppm) δ 152.6, 146.1, 133.9, 131.9, 130.1, 128.5, 123.5, 117.7, 115.0, 111.2, 77.4, 77.0, 76.7, 21.8.

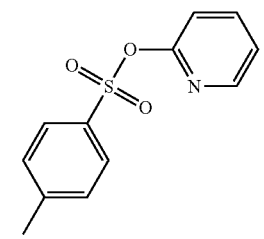 [SMILES: Cc1ccc(S(=O)(=O)Oc2ccccn2)cc1]

pyridin-2-yl p-toluenesulfonate (1s)

¹HNMR (400 MHz, CDCl₃, ppm) δ 8.43-8.53 (m, 1H), 8.15 (d, J=1.71 Hz, 1H), 7.63-7.76 (m, 2H), 7.42-7.52 (m, 1H), 7.33 (d, J=8.07 Hz, 2H), 7.25-7.31 (m, 1H), 2.45 (s, 3H); ¹³C NMR (100 MHz, CDCl₃, ppm) δ 148.5, 146.8, 146.3, 144.3, 132.0, 130.5, 130.3, 128.8, 124.5, 77.6, 77.3, 22.0.

References to NMR spectra of ¹⁹F-labeled compounds.
2a: Kim, K.; Miller, N. R.; Sulikowski, G. A.; Lindsley, C. W. *Bioorg. Med. Chem. Lett.* 2008, 18(16), 4467.
2b, 2q, 2s: Forlani, L.; Mezzina, E. *Bioorg. J. Chem. Soc. Perkin Trans.* 2 1995, 11, 2019. 2c: Ochiai, M.; Yoshimura, A.; Hoque, Md. M.; Okubo, T.; Saito, M.; Miyamoto, K. *Org. Lett.*, 2011, 13 (20), 5568.

2d, 2k, 2l: Koroniak, H.; Walkowiak, J.; Grys, K.; Rajchel, A.; Alty, A.; Du Boisson, R. *J. Fluorine Chem.* 2006, 127(9), 1245.

2e: Beaulieu, F.; Beauregard, L.-P.; Courchesne, G.; Couturier, M.; LaFlamme, F.; L'Heureux, A. *Org. Lett.* 2009, 11 (21), 5050.

2f, 2g: Prakash, G. K. S.; Chacko, S.; Vaghoo, H.; Shao, N.; Gurung, L.; Mathew, T.; Olah, G. A. *Org. Lett.* 2009, 11 (5), 1127.

2h, 2p: Tang, P.; Ritter, T. *Tetrahedron* 2011, 67(24), 4449.

2i: Cassidei, L.; Sciacovelli, O. *Spectrochim. Acta A-M.* 1985, 41(12), 1459.

2j: Jindrich, J.; Dvorakova, H.; Holy, A. *Collect. Czech. Chem. Commun.* 1992, 57, 1466.

2m: Tang, P.; Wang, W.; Ritter, T. *J. Am. Chem. Soc.,* 2011, 133 (30), 11482.

2n: Kruger, T.; Vorndran, K.; Linker, T. *Chem. Eur. J.* 2009, 15, 12082.

2o: Gieshoff, T. N.; Villa, M.; Welther, A.; Plois, M.; Chakraborty, U.; Wolf, R.; von Wangelin, A. *J. Green Chem.* 2015, 17, 1408.

2r: Enthaler, S. *Chem. Eur. J.* 2011, 17, 9316

2t: Chambers, R. D.; Parsons, M.; Sandford, G.; Skinner, C. J.; Atherton, M. J.; Moilliet, J. S. *J. Chem. Soc. Perkin Trans.* 1 1999, 7, 803.

2u: Ple, N.; Turck, A.; Heynderickx, A.; Queguiner, G. *Tetrahedron* 1998, 54(19), 4899.

2v: Bejot, R.; Fowler, T.; Carroll, L.; Boldon, S.; Moore, J. E.; Declerck, J.; Gouverneur, V. *Angew. Chem. Int. Ed.* 2008, 48, 586.

2w: Kumar. P.; Wiebe, L. I.; Asikoglu, M.; Tandon, M.; McEwan, A. J. B. *Appl. Radiat. Isotopes* 2002, 57(5), 697.

2x: Graham, T. J. A.; Lambert, R. F.; Ploessl, K.; Kung, H. F.; Doyle, A. G. *J. Am. Chem. Soc.* 2014, 136(14), 5291.

Example 8

General procedure for titania-catalyzed [$^{18}$F]-radiofluorination: A screw-cap scintillation vial was charged with $TiO_2$ (0.14 mmol) and tosylated precursor (2.3 µmol) solution in 1:1 mixture of acetonitrile and thexyl alcohol (30 µL). Vial was capped and incubated at room temperature for 1 hour. The aqueous solution of [$^{18}$F]F$^-$/TBAB was prepared by mixing equal volumes of [$^{18}$O]H$_2$O/[$^{18}$F] and 75 mM aqueous solution of TBAB. An aliquot of this solution (10 µl, containing 1.5-3 mCi radioactivity) was then added into pre-incubated reaction vial, resulting in 25% overall water content in reaction mixture. The vial was capped and transferred to computer-controlled Peltier heater. The reaction was performed at 130° C. for 5 minutes. After the reaction, the product was extracted with methanol (2×200 µl). Combined extracts were filtered through Whatman 'Anotop 10 Plus' filter (0.02 µm) and radiolabeled product content was analyzed by radio-TLC and HPLC.

Example 8.2 Determination of Specific Activity

High specific activity (SA) of PET tracers is essential to minimize the injected quantity of the non-radioactive form of the tracer, which can saturate rare biological targets, such as neurological receptors, and subsequently lower the image quality and possibly cause pharmacologic effects.[55] It has been confirmed that SA plays an important role in PET image quality,[29,56,57] especially in small animals.[58,59] Using standard methods[7], the SA for TiO2 catalyzed synthesis of [$^{18}$F]Fallypride 2a was found to be 5±2 Ci/µmol (n=5). This is higher than typically obtained from macroscale synthesis (0.4-3 Ci/µmol).[49,60] This evidence suggests $TiO_2$ catalysis could be successfully used for routine production of PET imaging probes that require high SA.

Example 8.3: Scale-Up Synthesis

Previous experiments utilized operating volumes of 40 µl, 10 µL of which was [$^{18}$F]fluoride solution. While we have been able to demonstrate the production of several millicuries of the isolated product starting from ~5 mCi of [$^{18}$F] fluoride, it may be desirable in some cases to produce larger amounts of product (e.g., for clinical production), which requires a larger volume of the initial [$^{18}$F]fluoride solution.

Figure 5:
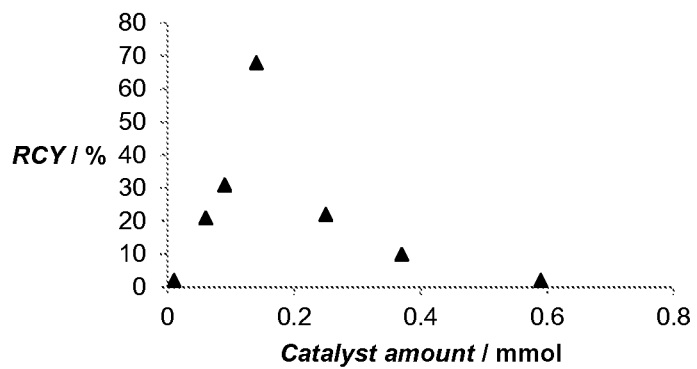
FIG. 5 is a graph showing the evaluation of catalyst loading amount.
Figure 6:
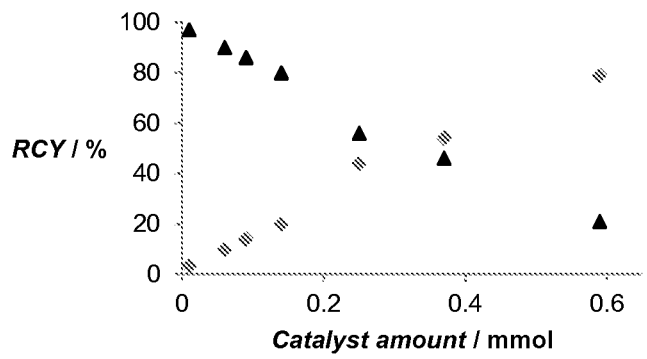
FIG. 6 is a graph showing the radioactivity extraction curves at different catalyst loading amount. Black triangles for organic extract, gray rhombi for trapping in catalytic layer.
Figure 7:
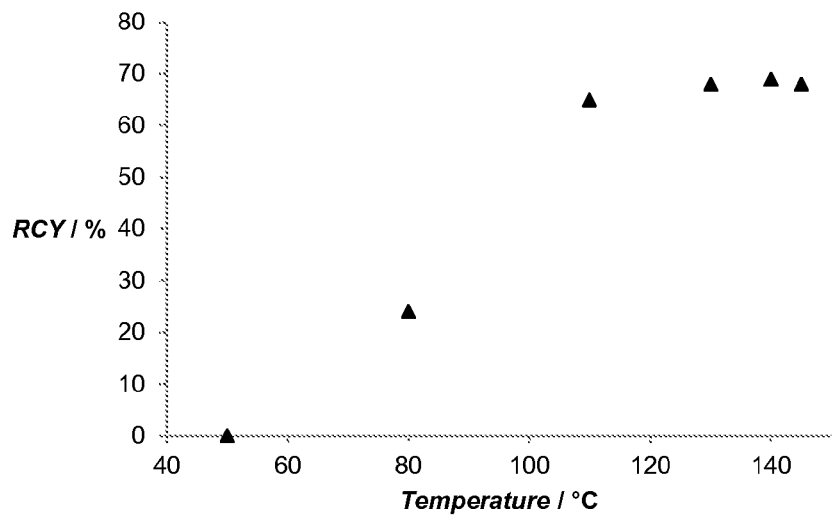
FIG. 7 is a graph showing the evaluation of temperature profile in $TiO_2$-catalyzed radiofluorination of tosyl-fallypride.
Figure 8:
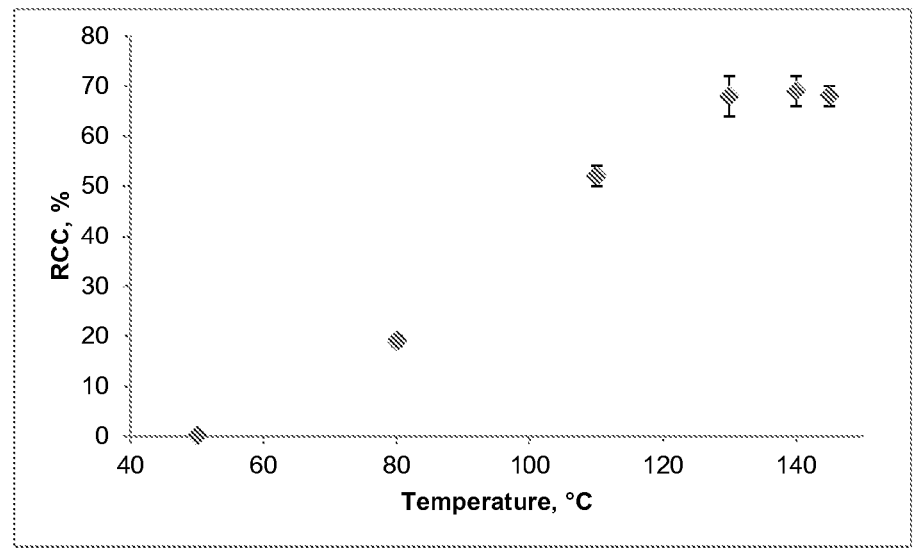
FIG. 8 is a graph showing the effect of temperature on RCC in $TiO_2$-catalyzed radiofluorination of tosyl-fallypride.
Figure 9:
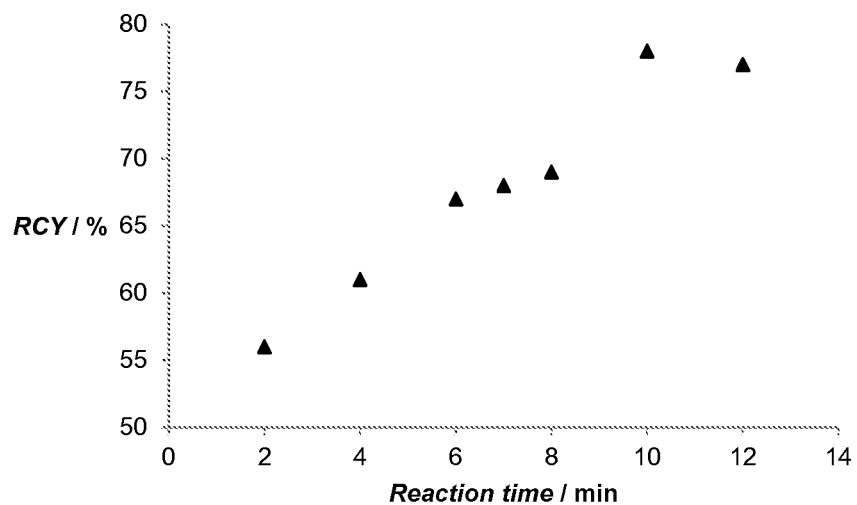
FIG. 9 is a graph showing the evaluation of time profile in $TiO_2$-catalyzed radiofluorination of tosyl-fallypride at 130° C.
Figure 10:
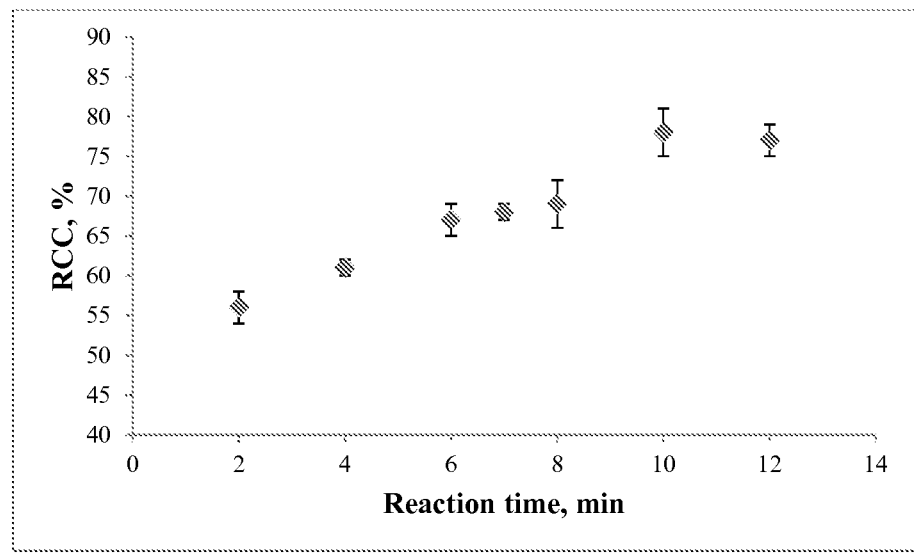
FIG. 10 is a graph showing the effect of reaction time on RCC of $TiO_2$-catalyzed radiofluorination of tosyl-fallypride 1a. Reaction was performed at 130° C.
Figure 11:
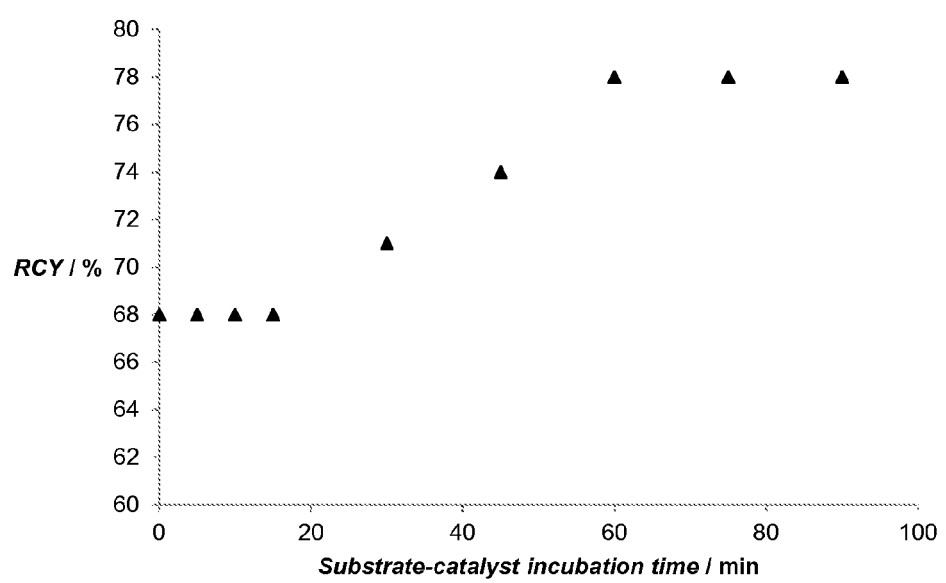
FIG. 11 is a graph showing the evaluation of substrate-catalyst incubation time.
Figure 12:
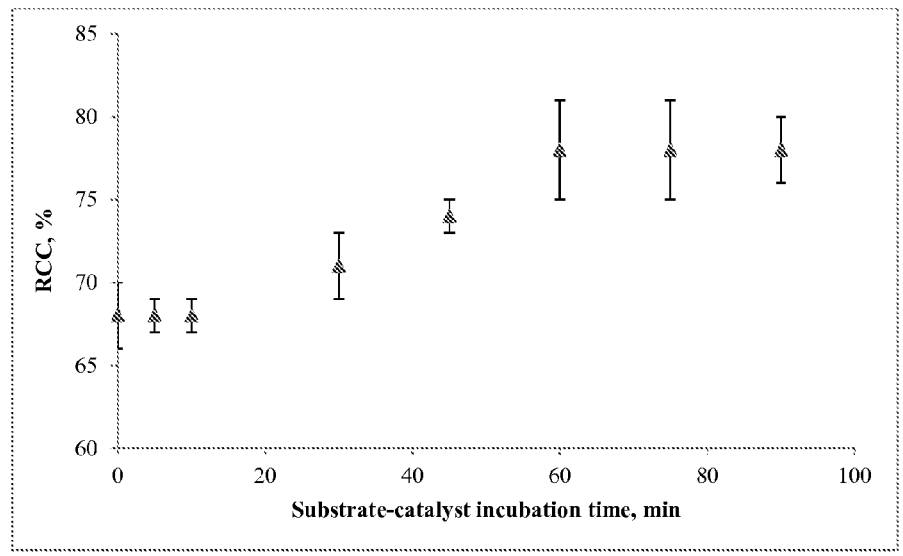
FIG. 12 is a graph showing the effect of substrate-catalyst incubation time on RCC.
Figure 13:
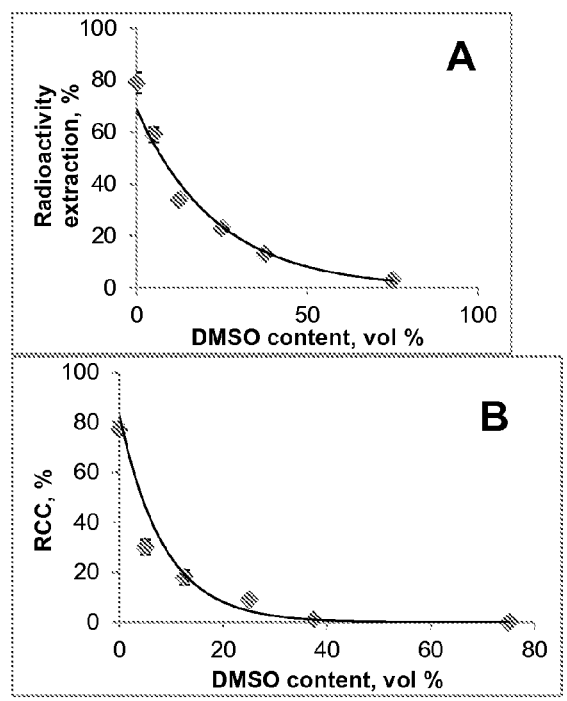
FIG. 13 is a graph showing the effect of DMSO addition on radiofluorination of 1a. A) Radioactivity extraction efficiency; B) Radiochemical conversion.
Figure 14:
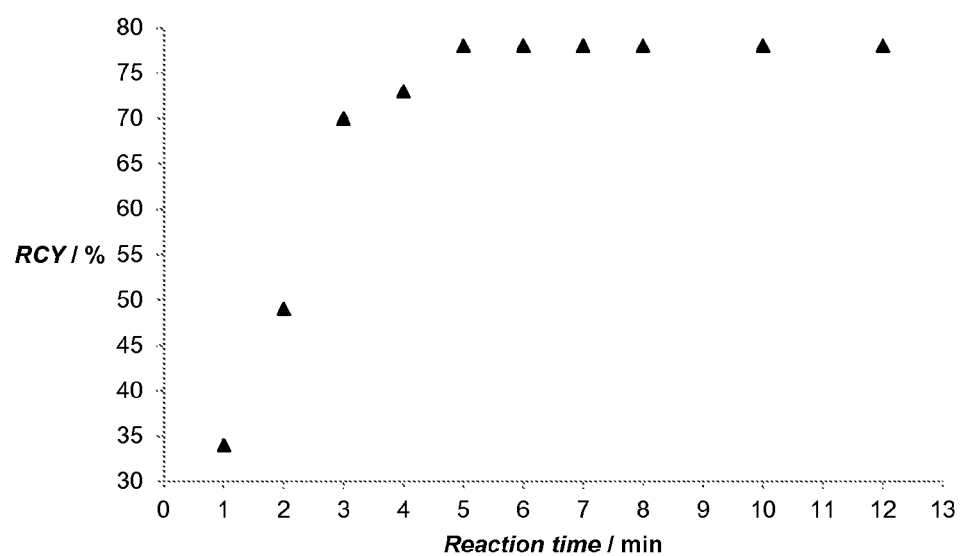
FIG. 14 is a graph showing the evaluation of radiofluorination time profile after substrate-catalyst incubation.
Figure 15:
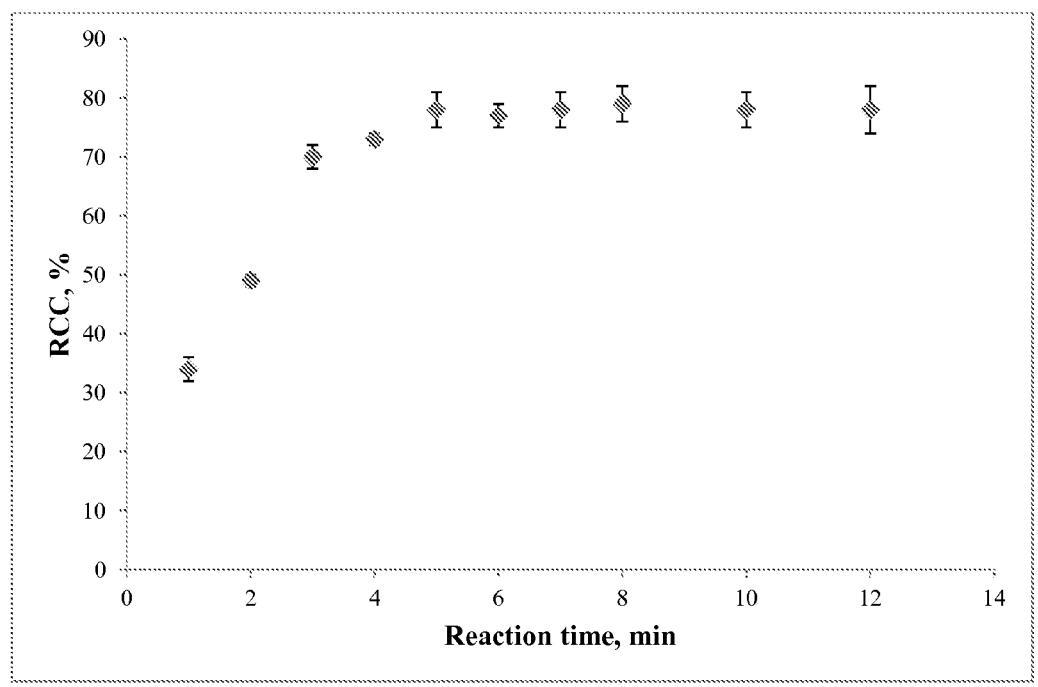
FIG. 15 is a graph showing the evaluation of radiofluorination time profile after 1 hr substrate-catalyst incubation.
Figure 16:
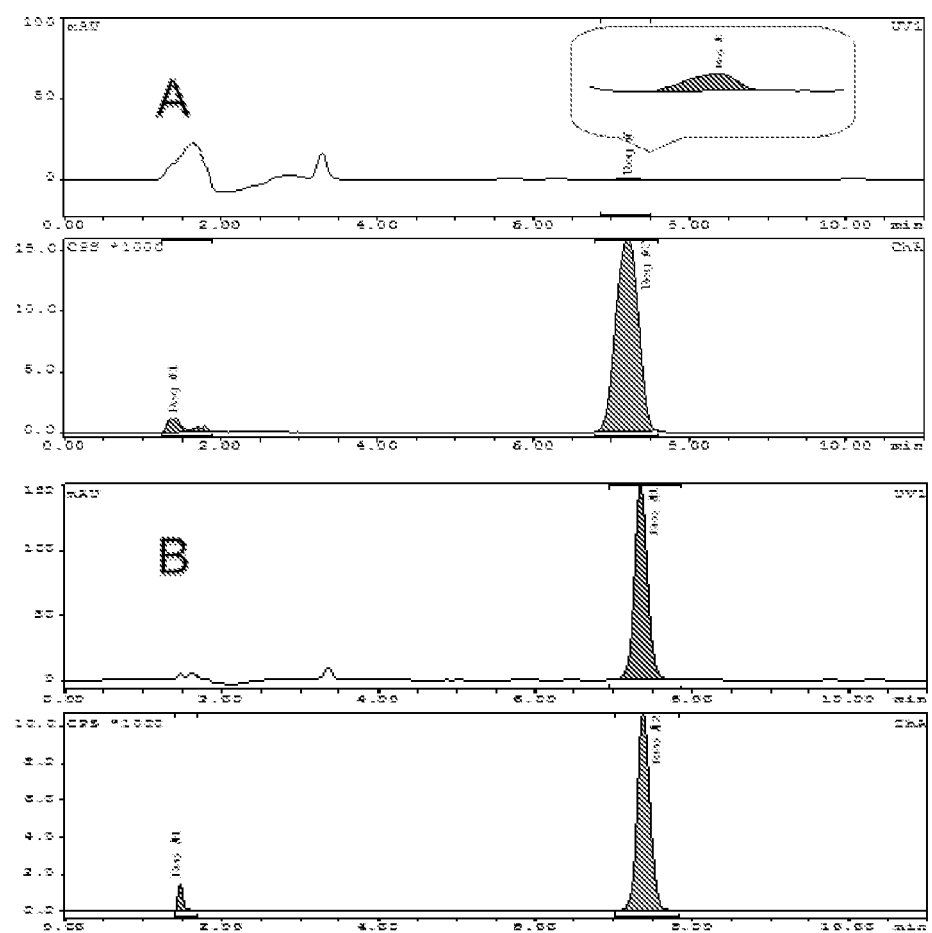
FIG. 16 is a series of graphs showing a) Exemplary HPLC-chromatogram of microchip [$^{18}$F]Fallypride preparation (crude product, prior to final purification).[1] Inset shows enlarged UV-area of target compound 2a. Top is UV absorbance signal, bottom is gamma signal. b) Co-injection with cold standard, [$^{19}$F]Fallypride.
Figure 17:
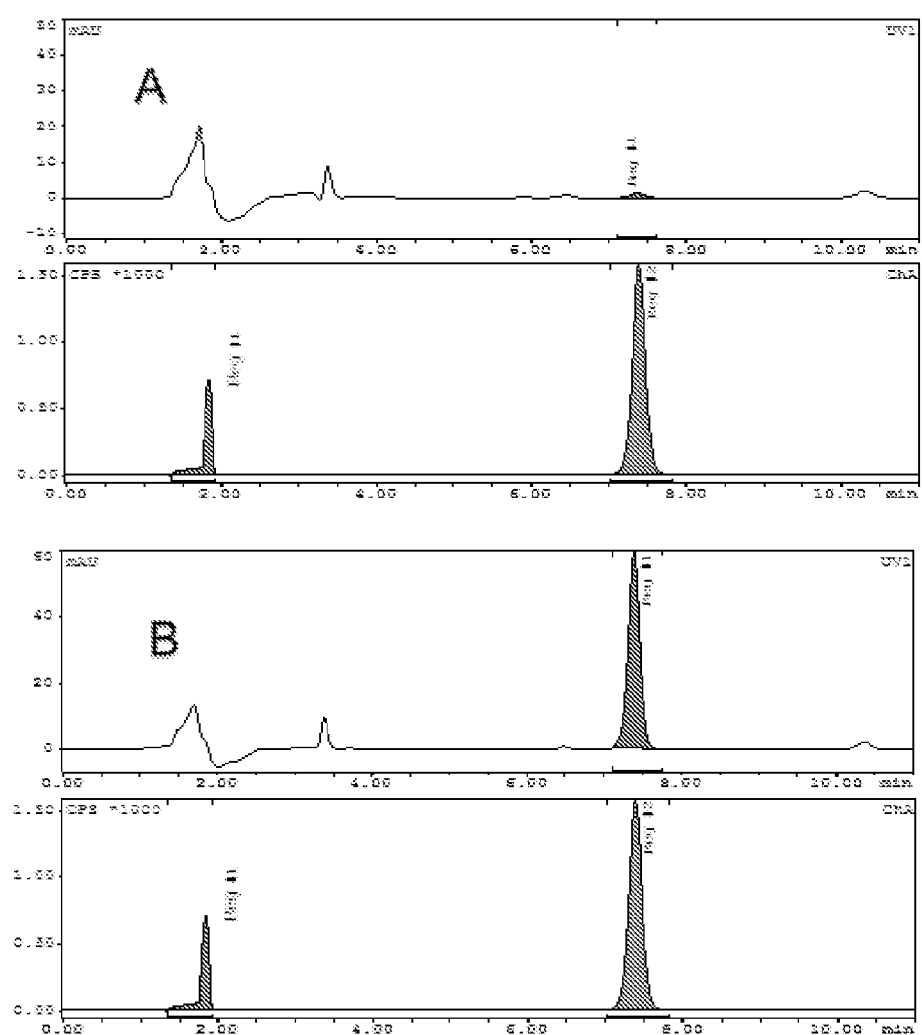
FIG. 17 is a series of graphs showing a) Exemplary HPLC-chromatogram of non-optimized $TiO_2$-catalyzed [$^{18}$F]Fallypride preparation (crude product, after extraction and before final purification). Top is UV absorbance signal; bottom is gamma signal. b) Co-injection with cold standard, [$^{19}$F]Fallypride.
Figure 18:
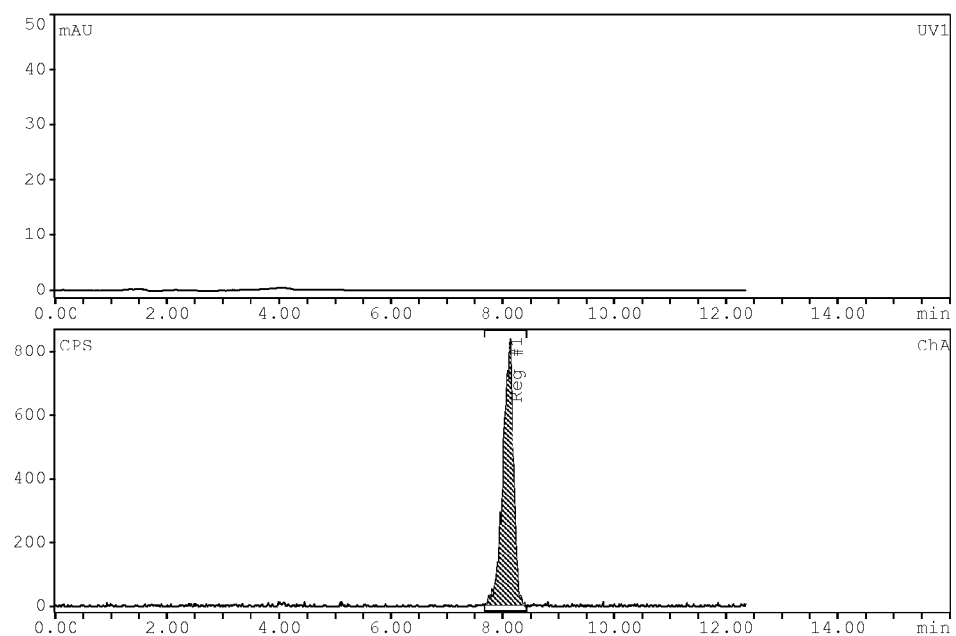
FIG. 18 is a series of graphs showing HPLC-chromatogram of injectable [$^{18}$F]Fallypride formulation.
Figure 21:
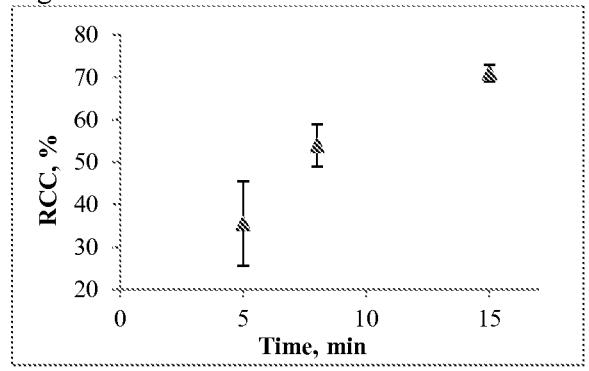
FIG. 21 is a graph showing the correlation between reaction time and fluorination efficiency in scaled-up catalytic radiolabeling of 1a. Values are averaged from n=9 experiments for 5 min runs, and n=6 for each of 8 and 15 min experiments.

One simple way to scale up the quantity of tracer produced is to run several reactions in parallel and pool the results; however, this would require multiple reaction vessels and may not be convenient to handle or automate. Another approach is to scale up the reaction volume, enabling a larger volume of [$^{18}$F]fluoride to be used while still keeping water content within the 25 vol % range, and thus enabling larger amount of starting radioactivity. To test this possibility, we explored proportionally increasing the amounts of all of the reaction components (i.e., precursor, $TiO_2$, solvent, and aqueous [$^{18}$F]fluoride/TBAB solution). As an example, the catalytic fluorination of 1a was scaled up to a factor of 3, such that the final volume of the reaction mixture comprised 120 µl. During these experiments, we found that 5 min reaction time was insufficient to efficiently fluorinate the precursor (fluorination efficiency=50%). With increased heating time, it was possible to increase fluorination efficiency to the values seen prior to scaling (FIG. 5). We suspect that longer time is needed for sufficient diffusive mixing in the larger volume. We also encountered some initial difficulties during the filtration step to remove the nanoparticles after the reaction was done. We observed clogging of the 20 nm filter due to the increased amount of $TiO_2$. This issue was resolved by incorporating an initial pre-filtration step with a 0.22 µm filter prior to 20 nm fine filtering. Unfortunately, this had the effect of slightly reducing the extraction efficiency, from 80±2% to 71±13% (FIG. 21).

The tested scale-up factor of 3 is sufficient for production of a human-dose of [$^{18}$F]Fallypride, and further increases in scale are presumably possible, if desired; with higher volumes, stirring during the pre-incubation and reaction steps may become important, requiring additional optimization of reaction time and extraction procedures. Another reason to perform volume scale-up is to potentially enable automation in commercially-available radiosynthesizers, which typically require at least several hundred microliters of solution in the reaction. Though there are advantages in performing reactions in extremely small volumes,[7,8] it will be some time before automated and commercialized versions of such technologies are widely available.

As an alternative way to increase the amount of radioactivity in the reaction without impacting reaction volume, solid phase extraction procedures using microscale QMA cartridges could be used to concentrate the [$^{18}$F]fluoride to obtain higher starting radioactivity in volumes of the [$^{18}$F] fluoride/TBAB solution described here (i.e. 10 µL water content). Several reports have shown that an entire cyclotron target volume can be trapped and efficiently eluted in only 5-45 µL of eluent solution.[61-63] This would likely be the preferred approach to scale-up the amount of radioactivity since no increase in reaction volume would be necessary.

Example 8.4 Substrate Scope

Figure 22:
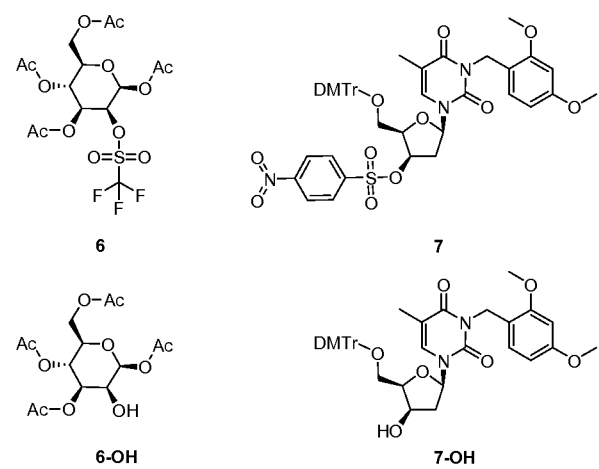
FIG. 22 is a picture showing additional substrates with sulfonyl-containing leaving groups and their corresponding hydrolysates.

In order to explore the utility of the $TiO_2$ catalytic approach for the synthesis of other PET tracers, we investigated the scope of applicable substrates. We first considered the use of other leaving groups with sulfonyl moieties (i.e., triflate and nosylate). Examples of additional leaving groups may be benzenesulfonyl, 4-methylbenzenesulfonyl (tosylate), 4-nitrobenzenesulfonyl (nosylate), methanesulfonyl (mesylate), ethanesulfonyl, trifluoromethylsulfonyl (triflate), or 1,1,2,2,2-pentafluoroethane-1-sulfonyl. Surprisingly, the radiofluorination of commercially available substrates 6 and 7 (precursors for 2'-deoxy-2'-[$^{18}$F]fluoro-D-glucose ([$^{18}$F]FDG), and 3'-deoxy-3'-[$^{18}$F]fluoro-L-thymidine ([$^{18}$F]FLT)) (FIG. 22) resulted in RCC=0%.

In a presence of the catalyst, triflate and nosylate groups seemed to become overreactive, and immediate explosive hydrolysis was observed upon aqueous [$^{18}$F]fluoride addition. When analyzed, only unreacted [$^{18}$F]fluoride and hydroxylated compounds 6-OH and 7-OH were detected. This phenomenon suggests that reactivity of oxygen-containing leaving groups are increased when incubated with TiO$_2$. Due to this additional activation, the ideal leaving group should initially possess lower reactivity (tosyloxy preferred before triflyloxy or nosyloxy), otherwise concurrent side-reaction of hydrolysis prevails over [$^{18}$F]fluorination.

We next investigated the generality of TiO$_2$-catalyzed radiofluorination of tosylated precursors. A library of aromatic, aliphatic and cycloaliphatic tosylates was tested, along with the commercially available tosylated PET probe precursors for [$^{18}$F]-4-fluoroproline ([$^{18}$F]-4-FP), [$^{18}$F]-fluoroazomycin-arabinoside ([$^{18}$F]FAZA) and [$^{18}$F]-fluoroerythronitroimidazole ([$^{18}$F]FETNIM) (Table 6). The methodology was highly efficient for low-molecular-weight precursors 1b-v (65-80% RCC) but resulted in low to moderate yields with bulky and sterically hindered substrates 1w-x (i.e., from the commercially available precursors for [$^{18}$F]FAZA and [$^{18}$F]FETNIM, respectively). These particular precursors also contain additional oxo-moieties, which potentially lower yields by coordinating the precursor at the catalyst surface instead of at the O=S=O moiety of the tosylate leaving group. Such coordination could significantly reduce the [$^{18}$F]fluoride interaction with the tosylate reactive center by placing the reaction center further from the catalyst surface where fluoride desolvation occurs. We are currently looking into methods to further understand the reaction mechanism to predict the effectiveness of different substrates and perhaps enable improved substrate design.

TABLE 16

Substrate scope for the TiO$_2$ catalyzed radiofluorination of tosylated substrates[a].

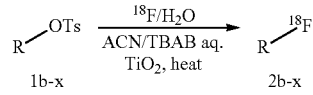

| | |
|---|---|
| 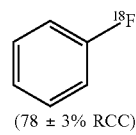 (78 ± 3% RCC) | 2b |
| 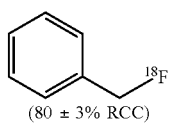 (80 ± 3% RCC) | 2c |

TABLE 16-continued

Substrate scope for the TiO$_2$ catalyzed radiofluorination of tosylated substrates[a].

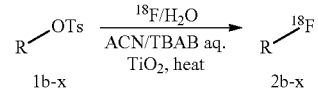

| | |
|---|---|
| 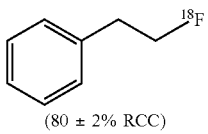 (80 ± 2% RCC) | 2d |
| 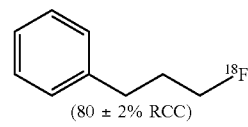 (80 ± 2% RCC) | 2e |
| 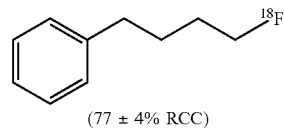 (77 ± 4% RCC) | 2f |
| 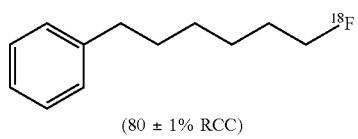 (80 ± 1% RCC) | 2g |
| 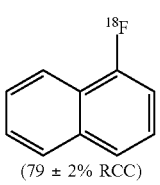 (79 ± 2% RCC) | 2h |
| 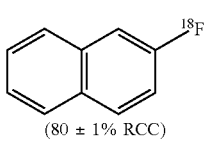 (80 ± 1% RCC) | 2i |
| 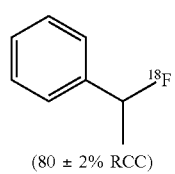 (80 ± 2% RCC) | 2j |
| 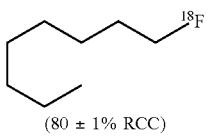 (80 ± 1% RCC) | 2k |
| 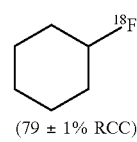 (79 ± 1% RCC) | 2l |
| 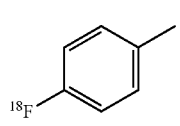 (74 ± 2% RCC) | 2m |

TABLE 16-continued

Substrate scope for the TiO₂ catalyzed radiofluorination of tosylated substrates[a].

$$R\text{-OTs} \xrightarrow[\text{TiO}_2,\ \text{heat}]{^{18}\text{F/H}_2\text{O},\ \text{ACN/TBAB aq.}} R\text{-}^{18}\text{F}$$
1b-x → 2b-x

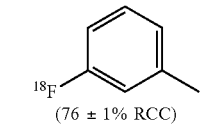
(76 ± 1% RCC) 2n

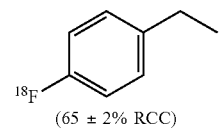
(65 ± 2% RCC) 2o

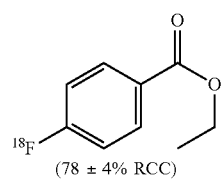
(78 ± 4% RCC) 2p

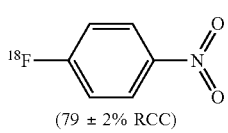
(79 ± 2% RCC) 2q

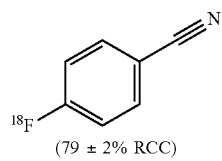
(79 ± 2% RCC) 2r

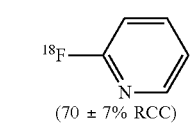
(70 ± 7% RCC) 2s

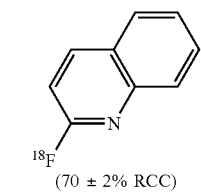
(70 ± 2% RCC) 2t

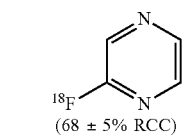
(68 ± 5% RCC) 2u

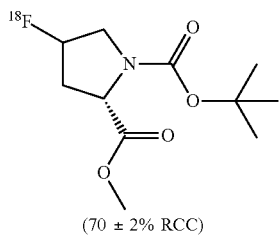
(70 ± 2% RCC) 2v

TABLE 16-continued

Substrate scope for the TiO₂ catalyzed radiofluorination of tosylated substrates[a].

$$R\text{-OTs} \xrightarrow[\text{TiO}_2,\ \text{heat}]{^{18}\text{F/H}_2\text{O},\ \text{ACN/TBAB aq.}} R\text{-}^{18}\text{F}$$
1b-x → 2b-x (50 ± 4% RCC) 2w (26 ± 4% RCC) 2x

[a]Optimized reaction conditions:
1 h pre-incubation time;
2.3 μmol of precursor;
140 μmol of TiO₂;
130° C., 5 min;
40 μl total reaction volume;
no magnetic stirring;
radioactivity introduced as 10 μl solution of aqueous [$^{18}$F]fluoride (1.5-4 mCi) containing 0.36 μmol TBAB.
For all entries, REE was observed to be ~80%.

In conclusion, we have developed a novel method of TiO₂-catalyzed radiofluorination of tosylated presursors and demonstrated its use for the preparation of $^{18}$F-labeled PET probes. The method avoids the need for drying of the [$^{18}$F]fluoride/[$^{18}$O]H₂O from the cyclotron before fluorination. The wet [$^{18}$F]fluoride is mixed with a phase transfer agent and added to a solution of precursor solution pre-incubated with TiO2 nanoparticles and reacted for a short time. In this fashion, nucleophilic $^{18}$F-fluorination is shown to proceed rapidly and efficiently in aqueous medium with up to 25 vol % water content, which to the best of our knowledge is the highest reported other than enzymatic methods. We have also demostrated the production of clinically-relevant amounts of [$^{18}$F]Fallypride with this approach as well as shown compliance of the final formulated PET tracer with QC requirements for clinical use. The product was found to have high specific activity even with low amounts of starting radioactivity. The applicability of the reported protocol to a range of tosylated substrates was also demonstrated for organic molecules containing aromatic, aliphatic and cycloaliphatic moieties. Although extensive additional investigations are required to explore the substrate scope and further understand the mechanism, we anticipate that the facile procedure and high radiofluorination efficiency of this new method may provide a versatile tool for practitioners in the field of PET radiochemistry. Based on our hypothesized mechanism of reaction, further studies regarding the importance of the structure of the precursor and other effective catalysts are currently in progress in our group.

Example 9

A panel of 25 TMOs in powder form (<200 nm particle size), were screened in the radiofluorination of tosyl-fallypride in a mixed aqueous-organic medium. Equal parts of [$^{18}$O]H$_2$O/[$^{18}$F]fluoride and aqueous 75 mM tetrabutylammonium hydrocarbonate (TBAB) were mixed, added to a one-hour pre-incubated solution of TMO and tosyl-fallypride in acetonitrile and 2,3-dimethyl-2-butanol (1:1 v/v), and then reacted at 130° C. for 5 min in a closed container. The final reaction mixture contained 20% water. Catalyst and substrate scope are further explored in the radiolabeling of an array of tosylated PET-precursors.

No fluoride conversion of tosyl-fallypride took place using oxides of Mo, Pt, Re, Ru, Ta, Sn, V and Y, nor for the absence of catalyst altogether. Low fluoride conversion (2-14%) was observed for Zr, Bi, Mn, Mo, Cr and W oxides. Moderate fluorine conversion (45-49%) was observed for Pd, Fe and Zn oxides. The best decay-corrected [$^{18}$F]fallypride radiochemical yields, comparable to those previously found for TiO$_2$ (78%), were obtained for In$_2$O$_3$ (65%), CuO (80%), NbO$_2$ (76%) and Nb$_2$O$_5$ (85%). These latter catalysts were applied to fluorination of other substrates: FAZA-precursor (5-50%), cis-FPro-precursor (4-70%), FETNIM-precursor (8-42%) and FET-precursor (70-73%).

Catalytic activity of TMOs towards radiofluorination in highly aqueous media was demonstrated. The radiolabeling was directly performed with aqueous [$^{18}$F]fluoride without the drying/azeotroping step with 20% water content in the reaction mixture. Thus, radiosynthesis time was significantly reduced while still maintaining high fluoride conversion. The general applicability of the synthetic strategy to an array of PET probes from tosylated precursors was demonstrated.

REFERENCES

M. R. Javed et al., Chem. Comm. 2014, 50, 1192-1194; M. Sergeev et al., "Titania-catalyzed [$^{18}$F]-radiofluorination of tosylated precursors in highly aqueous media", Manuscript in preparation.

TABLE 17

| | | |
|---|---|---|
| FAZA-precursor | TiO$_2$, 50 ± 3% (n = 3) | Nb$_2$O$_5$, 16 ± 1% (n = 3) |
| cis-FPro-precursor | TiO$_2$, 70 ± 4% (n = 3) | Nb$_2$O$_5$, 28 ± 1% (n = 3) |
| FETNIM-precursor | TiO$_2$, 26 ± 1% (n = 3) | Nb$_2$O$_5$, 42 ± 2% (n = 3) |
| FET-precursor | N/A | Nb$_2$O$_5$, 73 ± 4% (n = 3) |

List of screened substrates and decay-corrected yields comparing the use or TiO$_2$ and Nb$_2$O$_5$ catalysts

TABLE 18

Transition metal oxides screening in radiofluorination of tosylfallypride.

| # | Catalyst | Product Radio-Purity in Extract (%) | Extraction Efficiency | RCC, % |
|---|---|---|---|---|
| 1 | chromium(VI) oxide | 0 | | |
| 2 | molybdenum(VI) oxide | 0 | | |

TABLE 18-continued

Transition metal oxides screening in radiofluorination of tosylfallypride.

| # | Catalyst | Product Radio-Purity in Extract (%) | Extraction Efficiency | RCC, % |
|---|---|---|---|---|
| 3 | platinum(IV) oxide | 0 | | |
| 4 | rhenium(VI) oxide | 0 | | |
| 5 | rhenium(VII) oxide | 0 | | |
| 6 | ruthenium(IV) oxide | 0 | | |
| 7 | tantalum(V) oxide | 0 | | |
| 8 | tin(IV) oxide | 0 | | |
| 9 | vanadium(IV) oxide | 0 | | |
| 10 | vanadium(V) oxide | 0 | | |
| 11 | yttrium(III) oxide | 0 | | |
| 12 | zirconium(IV) oxide | 56.12 | 2.7 | 1.52 |
| 13 | chromium(III) oxide | 34.19 | 5.4 | 1.85 |
| 14 | bismuth(III) oxide | 9.38 | 22.8 | 2.14 |
| 15 | manganese(IV) oxide | 7.26 | 31.7 | 2.30 |
| 16 | tungsten(IV) oxide | 9.13 | 35.5 | 3.24 |
| 17 | molybdenum(IV) oxide | 24.93 | 23.9 | 5.96 |
| 18 | tungsten(VI) oxide | 43.39 | 32.1 | 13.92 |
| 19 | palladium(II) oxide | 55.49 | 80.7 | 44.78 |
| 20 | iron(II) oxide | 73.22 | 64.4 | 47.15 |
| 21 | zinc(II) oxide | 71.9 | 67.6 | 48.59 |
| 22 | indium(III) oxide | 90.96 | 71.4 | 64.97 |
| 23 | copper(II) oxide | 93.37 | 80.3 | 74.99 |
| 24 | niobium(IV) oxide | 89.92 | 84.7 | 76.20 |
| 25 | niobium(V) oxide | 95.33 | 85.3 | 81.31 |
| Ref | titanium(IV) oxide | | 80 | 78 |

TABLE 19

Transition metal oxide-catalyzed radiofluorination of tosylated PET-precursors. Values are decay-corrected radiochemical yields (%) and represented as an average of 3 experiments.

| Catalyst | Precursor | | | | |
|---|---|---|---|---|---|
| | 1 | 2 | 3 | 4 | 5 |
| TiO2 | 78 ± 4 | 50 ± 3 | 70 ± 4 | 26 ± 1 | — |
| NbO2 | 76 ± 4 | 7 ± 1 | 9 ± 1 | 8 ± 1 | 70 ± 4 |
| Nb2O5 | 81 ± 4 | 16 ± 1 | 28 ± 1 | 42 ± 2 | 73 ± 4 |
| In2O3 | 65 ± 3 | 5 ± 1 | 4 ± 1 | 9 ± 1 | — |
| CuO | 75 ± 4 | 12 ± 1 | 11 ± 1 | 34 ± 2 | — |

Precursors:

1. 2,3-dimethoxy-5-[3-[[(4-methylphenyl)sulfonyl]oxy]propyl]-N-[[1-(2-propenyl-2-pyrrolidinyl)methyl]] (tosylfallypride), fallypride precursor 2. 1-(2,3-diacetyl-5-tosyl-(a-D-arabinofuranosyl)-2-nitroimidazole, FAZA precursor 3. N-Boc-trans-4-tosyloxy-L-proline methyl ester (trans-BTPME), cis-4-fluoroproline precursor 4. (4R-trans)-2,2-dimethyl-5-[(2-nitro-1H-imidazol-1-yl)methyl]-1,3-dioxolane-4-methanol 4-methylbenzenesulfonate, FETNIM precursor 5. (2S)—O-(2'-tosyloxyethyl)-N-trityl-tyrosine-tert-butyl ester, FET precursor Example 9.1

Based on titania catalyzed reaction results, a new set of transition metal oxides was tested in reaction of radiofluorination. The model reaction used is the conversion of tosyl-fallypride to $^{18}$F-fallypride. Results of oxide-catalyst screening are compared to those previously found for TiO$_2$ catalysis.

TABLE 19.1

| # | Name | Purity in Extract (%) | Extracted Activity | Trapped Activity | Extr. Eff | RCC, % |
|---|---|---|---|---|---|---|
| 1 | chromium(VI) oxide | 0 | n/a | n/a | 0.0 | 0 |
| 2* | molybdenum(VI) oxide | 0 | n/a | n/a | 0.0 | 0 |
| 3 | platinum(IV) oxide | 0 | n/a | n/a | 0.0 | 0 |
| 4* | rhenium(VI) oxide | 0 | n/a | n/a | 0.0 | 0 |
| 5* | rhenium(VII) oxide | 0 | n/a | n/a | 0.0 | 0 |
| 6 | ruthenium(IV) oxide | 0 | n/a | n/a | 0.0 | 0 |
| 7 | tantalum(V) oxide | 0 | n/a | n/a | 0.0 | 0 |
| 8 | tin(IV) oxide | 0 | n/a | n/a | 0.0 | 0 |
| 9* | vanadium(IV) oxide | 0 | n/a | n/a | 0.0 | 0 |
| 10* | vanadium(V) oxide | 0 | n/a | n/a | 0.0 | 0 |
| 11 | yttrium(III) oxide | 0 | n/a | n/a | 0.0 | 0 |

With these catalysts, low yields of Fallypride were obtained using conditions established for Titania catalysis. Radioactivity extraction efficiency suffers with these catalysts, which inherently leads to low RCC. More thorough investigation of reaction conditions is planned to investigate whether these oxides could be applicable for radiofluorination reactions.

TABLE 19.2

| # | Name | Purity in Extract (%) | Extracted Activity | Trapped Activity | Extr. Eff | RCC, % |
|---|---|---|---|---|---|---|
| 1 | zirconium(IV) oxide | 56.12 | 5 | 180 | 2.7 | 1.52 |
| 2 | chromium(III) oxide | 34.19 | 11 | 192 | 5.4 | 1.85 |
| 3 | bismuth(III) oxide | 9.38 | 31 | 105 | 22.8 | 2.14 |
| 4 | manganese(IV) oxide | 7.26 | 51 | 110 | 31.7 | 2.30 |
| 5 | tungsten(IV) oxide | 9.13 | 44 | 80 | 35.5 | 3.24 |
| 6 | molybdenum(IV) oxide | 24.93 | 43 | 137 | 23.9 | 5.96 |
| 7 | tungsten(VI) oxide | 43.39 | 43 | 91 | 32.1 | 13.92 |

With these catalysts, moderate yields of Fallypride were obtained using conditions established for Titania catalysis. Extraction efficiency is comparable to titania-catalyzed reaction when Pd oxide was used, but moderate for Fe and Zn catalysts. More thorough investigation of reaction conditions is planned to investigate whether these oxides can be applicable for radiofluorination reactions.

TABLE 19.3

| # | Name | Purity in Extract (%) | Extracted Activity | Trapped Activity | Extr. Eff | RCC, % |
|---|---|---|---|---|---|---|
| 1 | palladium(II) oxide | 55.49 | 138 | 33 | 80.7 | 44.78 |
| 2 | iron(II) oxide | 73.22 | 123 | 68 | 64.4 | 47.15 |
| 3 | zinc(II) oxide | 71.9 | 196 | 94 | 67.6 | 48.59 |

For these catalysts, high yields of Fallypride were obtained using conditions established for Titania catalysis. Good extraction efficiency was also observed in all cases. These four catalysts have been further investigated for radiolabeling reaction efficiency at different conditions.

TABLE 19.4

| # | Name | Purity in Extract (%) | Extracted Activity | Trapped Activity | Extr. Eff | RCC, % |
|---|---|---|---|---|---|---|
| 1 | indium(III) oxide | 90.96 | 140 | 56 | 71.4 | 64.97 |
| 2 | copper(II) oxide | 93.37 | 155 | 38 | 80.3 | 74.99 |
| 3 | niobium(IV) oxide | 89.92 | 150 | 27 | 84.7 | 76.20 |
| 4 | niobium(V) oxide | 95.33 | 145 | 25 | 85.3 | 81.31 |

A summary chart is shown below:

TABLE 19.5

| # | Name | MW | mg (0.075 mmol) | Purity in Extract (%) | Extracted Activity | Trapped Activity | Extr. Eff | RCC, % |
|---|---|---|---|---|---|---|---|---|
| 1 | bismuth(III) oxide | 465.96 | 34.9 | 9.38 | 31 | 105 | 22.8 | 2.14 |
| 2 | chromium(III) oxide | 151.99 | 11.4 | 34.19 | 11 | 192 | 5.4 | 1.85 |
| 3 | chromium(VI) oxide | 99.99 | 7.5 | 0 | n/a | n/a | | |
| 4 | copper(II) oxide | 79.545 | 6.0 | 93.37 | 155 | 38 | 80.3 | 74.99 |
| 5 | indium(III) oxide | 277.64 | 20.8 | 90.96 | 140 | 56 | 71.4 | 64.97 |
| 6 | iron(II) oxide | 71.844 | 5.4 | 73.22 | 123 | 68 | 64.4 | 47.15 |
| 7 | manganese(IV) oxide | 86.9368 | 6.5 | 7.26 | 51 | 110 | 31.7 | 2.30 |
| 8 | molybdenum(IV) oxide | 127.94 | 9.6 | 24.93 | 43 | 137 | 23.9 | 5.96 |
| 9 | molybdenum(VI) oxide | 143.94 | 10.8 | 0 | n/a | n/a | | |
| 10 | niobium(IV) oxide | 124.91 | 9.4 | 89.92 | 150 | 27 | 84.7 | 76.20 |
| 11 | niobium(V) oxide | 265.81 | 19.9 | 95.33 | 145 | 25 | 85.3 | 81.31 |
| 12 | palladium(II) oxide | 122.42 | 9.2 | 55.49 | 138 | 33 | 80.7 | 44.78 |
| 13 | platinum(IV) oxide | 227.08 | 17.0 | 0 | n/a | n/a | | |
| 14 | rhenium(VI) oxide | 234.205 | 17.6 | n/a | 90 | 73 | | |
| 15 | rhenium(VII) oxide | 484.41 | 36.3 | 0 | n/a | n/a | | |
| 16 | ruthenium(IV) oxide | 133.07 | 10.0 | 0 | n/a | n/a | | |
| 17 | tantalum(V) oxide | 441.893 | 33.1 | 0 | n/a | n/a | | |
| 18 | tin(IV) oxide | 150.71 | 11.3 | 0 | n/a | n/a | | |
| 19 | tungsten(IV) oxide | 215.84 | 16.2 | 9.13 | 44 | 80 | 35.5 | 3.24 |
| 20 | tungsten(VI) oxide | 231.84 | 17.4 | 43.39 | 43 | 91 | 32.1 | 13.92 |
| 21 | vanadium(IV) oxide | 82.94 | 6.2 | 0 | n/a | n/a | | |
| 22 | vanadium(V) oxide | 181.88 | 13.6 | 0 | n/a | n/a | | |
| 23 | yttrium(III) oxide | 225.81 | 16.9 | n/a | n/a | n/a | | |
| 24 | zinc(II) oxide | 81.408 | 6.1 | 71.9 | 196 | 94 | 67.6 | 48.59 |
| 25 | zirconium(IV) oxide | 123.218 | 9.2 | 56.12 | 5 | 180 | 2.7 | 1.52 |

Preliminary results indicated promising results for these catalysts so experiments were repeated. Statistical data set for In(III), Nb(IV), Nb(V) and Cu(II) catalyzed fallypride formation is shown and compared to titania. Results are repeatable as evidenced by a narrow standard deviation.

TABLE 19.6

| Oxide | Extraction | RCC, % |
|---|---|---|
| TiO2 | 80 ± 2 | 78 ± 2 |
| In2O3 | 72 ± 4 | 65 ± 5 |
| NbO2 | 80 ± 5 | 80 ± 5 |
| Nb2O5 | 85 ± 3 | 85 ± 5 |
| CuO | 80 ± 4 | 75 ± 5 |

Transition metal oxides screening: 130 C, 5 min.

Example 9.2

Investigation on temperature profile was performed. It was found that T-optimum for four oxides of interest is the same as for Titania. Plateau was achieved at 130° C.; no obvious RCC increase is found beyond this point. This temperature is used for further reactions.

Time profiles were also collected. It was revealed that the optimal time for all these reactions is 5 min, after which point no substantial change in RCC was found. It was noted that in case of Cu, Nb(IV) and Nb(V) oxides that the reaction can be terminated after 3 minutes without significant loss in RCC, while In-catalyzed reaction shows substantial increase in RCC between 3 and 5 minutes.

Figure 23:
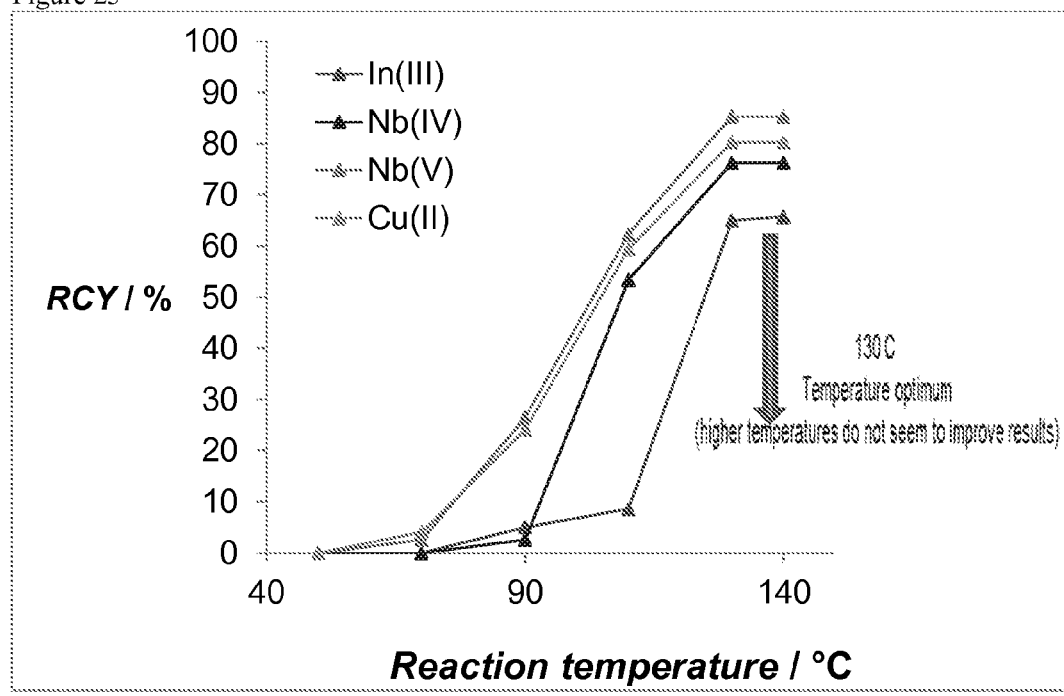
FIG. 23 is a graph showing Transition metal oxides screening of the Temperature profile.
Figure 24:
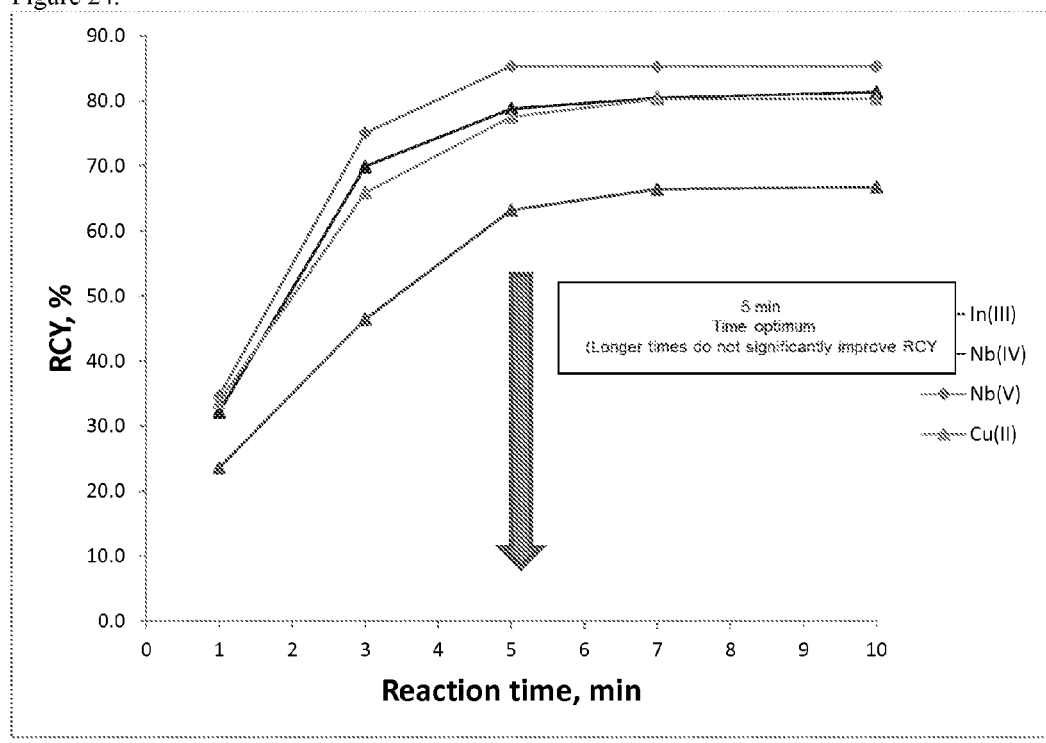
FIG. 24 is a graph showing Transition metal oxides screening of the Time profile.

With these conditions, new set of reactions was performed in order to determine the specific activity of radiolabeled fallypride. Reference reaction (not using catalytic method) was performed with a standard procedure using dried/ azeotroped fluoride in microchip synthesis (FIGS. 23 and 24).

TABLE 19.7

| Run | Specific Activity (Ci/μmol) |
|---|---|
| Non-catalytic method performed on microchip | 4.5 |
| TiO$_2$ | 4.6 |
| In$_2$O$_3$ | 4 |
| NbO$_2$ | 5.7 |
| Nb$_2$O$_5$ | 5.9 |
| CuO | 5.9 |

Specific activity in newly-developed synthesis was found to be comparable with standard (non-catalytic) preparation method. No significant difference was observed when 5 oxides under investigation were used. This adds one more advantage to our invention as we can synthesize PET tracers with high specific activity, even starting with low radioactivity.

A set of ABX substrates for commercial PET tracer synthesis was tested for applicability in oxide-catalyzed synthesis. It was shown that fallypride is synthesized with high efficiency in all cases, while it was impossible to detect FHBG or FETA formation in any reaction. FAZA and BTPME precursors were found to be less preferable substrates for In, Nb and Cu oxides compared to TiO$_2$, while FETNIM precursor was more effectively fluorinated with Nb(V) oxide than with Titania. No FET formation was found in case of Ti, Cu and In oxides, but surprisingly high RCC was observed when niobium oxides are used.

Currently we assume that transition metal in oxide catalyst and the precursor undergo the intermediate complex formation which is further fluorinated. Deeper investigation of precursor architecture and transition metal is planned for further steps of our research.

TABLE 19.8

RCC using the indicated PET tracer precursor (%). "—" indicates no product.

| Catalyst | Fallypride | FAZA | BTPME | FETNIM | TETA | TET | FHBG |
|---|---|---|---|---|---|---|---|
| TiO2 | 78 | 50 | 70 | 26 | — | — | — |
| NbO2 | 76 | 7.2 | 8.5 | 7.9 | 2.1 | 69.5 | — |
| Nb2O5 | 81 | 15.5 | 28 | 42 | 3 | 73 | — |
| In2O3 | 65 | 5 | 3.5 | 8.5 | — | — | — |
| CuO | 75 | 12 | 11 | 34 | — | — | — |

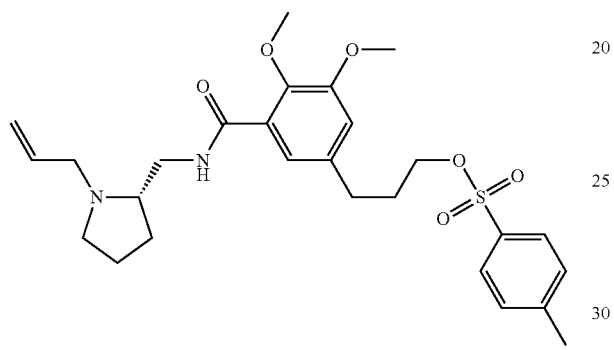

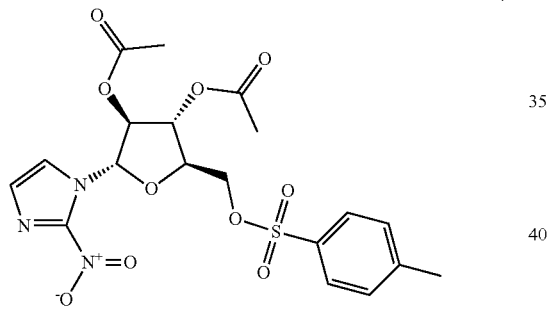

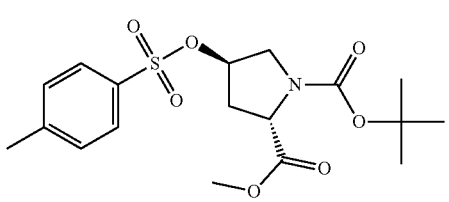

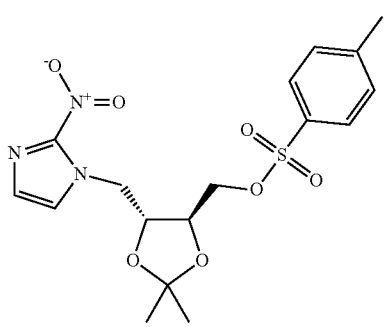

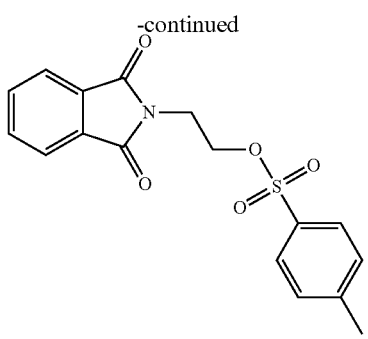

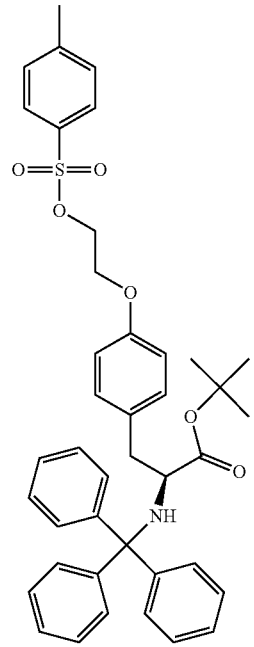

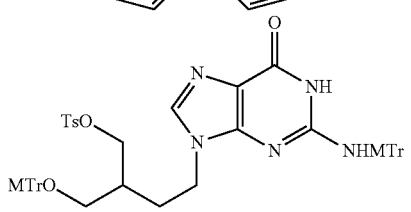

Example 10

We performed a series of experiments (Table 1) to confirm the importance of each species in the reaction. Entries 1 and 2 show the conventional synthesis conditions where [$^{18}$F]fluoride is pre-dried and reaction takes place in anhydrous organic media. The improvement in RCC due to addition of thexyl alcohol is apparent. Entry 5 shows 68% RCC resulting from catalytic synthesis conditions with all species included as described above. Comparative runs without the phase transfer catalyst resulted in only 18% RCC. Thus, the phase transfer agent appears to be important as well, possibly due to better solubilization of in situ generated tetra-n-butylammonium fluoride ([$^{18}$F]TBAF), compared to [$^{18}$F]fluoride, in organic-aqueous media. As expected, experiments in the absence of catalyst did not lead to formation of desired product 2a in organic-aqueous media (Entry 3), indicating that TiO$_2$ is essential when there is water in the reaction mixture. If the [$^{18}$F]fluoride is dried (as in conventional synthesis) prior to catalytic reaction, no conversion was observed (Entry 6). In fact, the filtrate contained neither fluorinated product nor parent [$^{18}$F]fluoride; all the radioactivity was found bound to the catalyst. This means that in non-aqueous media, TiO$_2$ addition results in total [$^{18}$F]fluoride trapping (REE ~0%). On the other hand, REE was found to be remarkably constant (~80%) for all of the TiO$_2$ catalyzed conditions containing water. Even if the reaction was performed without the precursor, the REE was unchanged (80±2%).

The influence of the type of phase-transfer agent was evaluated by carrying out the reaction with K$_2$CO$_3$/K$_{222}$ mixture (Entry 7). This resulted in a substantial decrease in RCC suggesting that TBAB is a superior phase transfer agent for these reactions.

Finally, to assess whether the role of TiO$_2$ was simply to sequester water to facilitate fluorination in mixed aqueous-organic media, comparative runs with particles of other common non-oxide drying agents, MgSO$_4$ and CaCl$_2$ (140 µmol each), were also performed (Entries 9-10). These showed zero RCC, suggesting an effect of TiO$_2$ beyond simple water adsorption, but most probably its ability of water splitting.

TABLE 20

Influence of reaction components on formation of 2a.[a]

| # | Catalyst | Phase transfer agent[b] | MeCN, µl | Thexyl alcohol, µl | Water, µl[c] | REE, % | RCC, % |
|---|----------|-------------------------|----------|--------------------|--------------|--------|--------|
| 1 | none | TBAB | 40 | 0 | 0 | 100[d] | 31 ± 2 |
| 2 | none | TBAB | 20 | 20 | 0 | 100[d] | 64 ± 4 |
| 3 | none | None | 15 | 15 | 10 | 100[d] | 0 |
| 4 | TiO$_2$ | None | 15 | 15 | 10 | 79 ± 4 | 18 ± 3 |
| 5 | TiO$_2$ | TBAB | 15 | 15 | 10 | 80 ± 3 | 68 ± 2 |
| 6 | TiO$_2$ | TBAB | 20 | 20 | 0 | 0 | 0 |
| 7 | TiO$_2$ | K$_2$CO$_3$/K$_{222}$ | 15 | 15 | 10 | 78 ± 3 | 39 ± 6 |
| 8 | none | K$_2$CO$_3$/K$_{222}$ | 20 | 20 | 0 | 100[d] | 31 ± 4 |
| 9 | MgSO$_4$ | TBAB | 15 | 15 | 10 | 99 ± 1 | 0 |
| 10 | CaCl$_2$ | TBAB | 15 | 15 | 10 | 99 ± 1 | 0 |

[a]Reactions were performed with 2.3 µmol 1a, 140 µmol TiO$_2$ in 40 µL reaction volume at 110° C. for 7 min without magnetic stirring.
[b]Amounts of phase transfer agent used, when applicable: 0.36 µmol TBAB; 0.36 µmol K$_2$CO$_3$ and 0.36 µmol K$_{222}$.
[c]For cases where water is 0 µL, [$^{18}$F]fluoride added as dry complex with phase-transfer agent (1.5-4 mCi) reconstituted in 10 µl of MeCN-thexyl alcohol (1:1 v/v); for other cases, radioactivity introduced as solution of aqueous [$^{18}$F]fluoride (1.5-4 mCi) containing phase-transfer agent;
[d]In case of catalyst absence no extraction performed.

Example 11

Hypothesized mechanism of TiO$_2$-catalyzed radiofluorination: Previous reports show that oxo- and oxy-containing species readily coordinate on a TiO$_2$ surface through hydrogen bonding.[32-35] Thus, we hypothesize that in addition to an interaction with water, the TiO$_2$ catalyst could also serve to coordinate tosyl-Fallypride 1a via oxygen atoms of the sulfonyl group, facilitating reaction with desolvated [$^{18}$F]fluoride in close proximity. Based on these ideas, the following mechanism of catalyzed fluorination is suggested (FIG. 19).

Hydrogen bonding occurs between oxygen atoms of the sulfonyl moiety and TiO$_2$, which coordinates tosylated precursor to the surface of the catalyst; when aqueous [$^{18}$F]fluoride/TBAB solution is added, solvated [$^{18}$F]fluoride is adsorbed at active sites of TiO$_2$ where the aqueous shell is split resulting in [$^{18}$F]fluoride release (i.e., activation); TBAB phase transfer catalyst then serves as a [$^{18}$F]fluoride-trapping agent and intercepts activated [$^{18}$F]fluoride, subsequently conducting the phase-transfer of [$^{18}$F]fluoride to the surface-coordinated precursor to facilitate the SN$_2$-type reaction. Because the coordination with the precursor is at the leaving group, the resulting radiofluorinated product is released upon formation from the TiO$_2$.

Evidence for coordination: To explore the role of coordination in the reaction mechanism, we performed radiolabeling after first incubating the tosylated substrate with catalyst. If coordination indeed occurs, prolonged exposure of the precursor to the catalyst should increase the amount of precursor bound to the surface of the catalyst and thus promote increased SN$_2$-reactions (i.e., radiolabeling efficiency). Thus, a solution of tosyl-Fallypride 1a in 1:1 (v/v) MeCN-thexyl alcohol was added to the catalyst and incubated at room temperature for various durations. After incubation, aqueous [$^{18}$F]fluoride/TBAB mixture was added, and radiolabeling was performed by heating at 110° C. for 12 min using an oil bath. The reaction mixture was mixed by refluxing solvent; no magnetic stirring was used. We observed a modest enhancement in RCC starting after 20-30 min of incubation and reaching a maximum improvement after ~1 hr.

Analytical samples of organic solution after incubation with catalyst contained significant amount of precursor 1a; thus, it is likely that the observed saturation is due to occupation of all accessible active sites of TiO$_2$ capable of binding the oxygen-atoms of the leaving group. Attempts to perform pre-incubation at elevated temperatures (30, 45 and 60° C.) showed similar results, i.e., the timescale was not shortened. It should be noted that the pre-incubation step was performed before the introduction of [$^{18}$F]fluoride; therefore, incorporation of pre-incubation into the synthesis protocol does not introduce any delays that would affect the yield due to decay.

Studies were performed by running the radiofluorination reaction in the presence of various amounts of a non-reactive SO-containing compound (dimethylsulfoxide, DMSO) to assess whether the presence of another co-coordinating species could block the binding of the precursor and lower the RCC.

It was revealed that even slight addition of DMSO dramatically affected the RCC; 2-fold decrease in RCC was registered at 5 vol % DMSO with nearly complete inhibition at 37.5 vol % DMSO, suggesting that DMSO molecules may indeed bind to active sites of TiO$_2$, thus reducing sites available for precursor coordination. Surprisingly, the REE was also significantly affected, and the amount of [$^{18}$F]fluoride trapped onto the catalyst increased with increasing DMSO content. Almost total [$^{18}$F]fluoride trapping (90%) was registered at 75 vol % DMSO. This suggests that instead of merely affecting precursor coordination, DMSO may interact with the catalyst in additional ways leading to trapping of fluoride, such as DMSO-water cluster formation,[36-39] intercalation of DMSO-water clathrate inside the oxide structure,[40] or DMSO-induced creation of positively-charged sites.[41]

To investigate further the need for leaving group coordination at the TiO$_2$ surface, experiments were performed comparing tosylated compounds 1b, 1c and 1s with their brominated versions 3-5 (not suspected to coordinate with surface) in TiO$_2$-catalyzed [$^{18}$F]fluorination (Table 21). No product was observed in case of bromo-derivatives, while high RCCs of ~80% were determined for tosylated precursors, which agrees with the necessity for the proposed oxygen-coordinating mechanism at the leaving group. The REE in case of bromo-substituted substrates remained close to 80%, i.e., similar to that for tosylated reactants.

TABLE 21

TiO$_2$ catalyzed radiofluorination of tosylated vs. brominated substrates[a].

| Entry | Structure | |
|---|---|---|
| 1 | 1b (78 ± 3% RCC) | 3 (0% RCC) |
| 2 | 1c (80 ± 3% RCC) | 4 (0% RCC) |
| 3 | 1s (70 ± 7% RCC) | 5 (0% RCC) |

[a]1 h pre-incubation time;
2.3 µmol of precursor;
140 µmol of TiO$_2$;
130° C., 5 min;
40 µl total reaction volume;
no magnetic stirring; radioactivity introduced as 10 µl solution of aqueous [$^{18}$F]fluoride (1.5-4 mCi) containing 0.36 µmol TBAB.
~80% of radioactivity extraction efficiency (REE) observed for every entry.

REFERENCES (1) Hanahan, D.; Weinberg, R. A. *Cell* 2000, 100, 57.
(2) S☐hirrma☐her, R.; Wangler, C.; S☐hirrma☐her, E. *Mini-Rev. Org. Chem.* 2007, 4, 317.
(3) Cai, L.; Lu, S.; Pike, V. W. *Eur. J. Org. Chem.* 2008, 2008, 2853.
(4) Brooks, A. F.; Top☐zewski, J. J.; I☐hiishi, N.; Sanford, M. S.; S☐ott, P. J. H. *Chem. Sci.* 2014, 5, 4545.
(5) Wu, J. *Tetrahedron Lett.* 2014, 55, 4289.
(6) Seo, J. W.; Lee, B. S.; Lee, S. J.; Oh, S. J.; Chi, D. Y. *Bull. Korean Chem. Soc.* 2011, 32, 71.
(7) Javed, M. R.; Chen, S.; Lei, J.; Collins, J.; Sergeev, M.; Kim, H.-K.; Kim, C.-J.; Dam, R. M. van; Keng, P. Y. *Chem. Commun.* 2014, 50, 1192.
(8) Sergeev, M.; Lazari, M.; Collins, J.; Morgia, F.; Javed, M. R.; Keng, P. Y.; van Dam, R. M. Proceedings of the 6$^{th}$ International Symposium on Microchemistry and Microsystems (ISMM-2014), Singapore, Jul. 30-Aug. 1, 2014; pp 77-78.
(9) Onega, M.; Domarkas, J.; Deng, H.; S☐hweiger, L. F.; Smith, T. A. D.; Wel☐h, A. E.; Plisson, C.; Gee, A. D.; O'Hagan, D. *Chem. Commun.* 2010, 46, 139.
(10) Eustaquio, A. S.; O'Hagan, D.; Moore, B. S. *J. Nat. Prod.* 2010, 73, 378.
(11) Sergeev, M. E.; Morgia, F.; Javed, M. R.; Doi, M.; Keng, P. Y. *J. Mol. Catal. B Enzym.* 2013, 92, 51.
(12) Sergeev, M. E.; Morgia, F.; Javed, M. R.; Doi, M.; Keng, P. Y. *J. Mol. Catal. B: Enzym.* 2013, 97, 74.
(13) Kamlet, A. S.; Neumann, C. N.; Lee, E.; Carlin, S. M.; Moseley, C. K.; Stephenson, N.; Hooker, J. M.; Ritter, T. *PLoS ONE* 2013, 8, e59187.
(14) Furuya, T.; Ritter, T. *Org. Lett.* 2009, 11, 2860.
(15) Lee, E.; Kamlet, A. S.; Powers, D. C.; Neumann, C. N.; Boursalian, G. B.; Furuya, T.; Choi, D. C.; Hooker, J. M.; Ritter, T. *Science* 2011, 334, 639.
(16) Huang, X.; Liu, W.; Ren, H.; Neelamegam, R.; Hooker, J. M.; Groves, J. T. *J. Am. Chem. Soc.* 2014, 136, 6842.
(17) Tredwell, M.; Preshlo☐k, S. M.; Taylor, N. J.; Gruber, S.; Huiban, M.; Pass☐hier, J.; Mer☐ier, J.; Géni☐ot, C.; Gouverneur, V. *Angew. Chem.* 2014, 126, 1.
(18) I☐hiishi, N.; Brooks, A. F.; Top☐zewski, J. J.; Rodni☐k, M. E.; Sanford, M. S.; S☐ott, P. J. H. *Org. Lett.* 2014, 16, 3224.
(19) Chun, J.-H.; Telu, S.; Lu, S.; Pike, V. W. *Org. Biomol. Chem.* 2013, 11, 5094.
(20) M☐Bride, W. J.; Sharkey, R. M.; Goldenberg, D. M. *EJNMMI Res.* 2013, 3, 36.
(21) Kumar, S. G.; Devi, L. G. *J. Phys. Chem. A* 2011, 115, 13211.
(22) Frös hl, T.; Hörmann, U.; Kubiak, P.; Kučerová, G.; Pfanzelt, M.; Weiss, C. K.; Behm, R. J.; Hüsing, N.; Kaiser, U.; Landfester, K.; Wohlfahrt-Mehrens, M. *Chem. Soc. Rev.* 2012, 41, 5313.
(23) Zhang, C.; Lindan, P. J. D. *J. Chem. Phys.* 2003, 118, 4620.
(24) Diebold, U. *Surf. Sci. Rep.* 2003, 48, 53.
(25) Di Valentin, C.; Tilo☐a, A.; Selloni, A.; Be☐k, T. J.; Klust, A.; Batzill, M.; Losovyj, Y.; Diebold, U. *J. Am. Chem. Soc.* 2005, 127, 9895.
(26) Hammer, B.; Wendt, S.; Besenba☐her, F. *Top. Catal.* 2010, 53, 423.
(27) Onal, I.; Soyer, S.; Senkan, S. *Surf. Sci.* 2006, 600, 2457.
(28) Constantines☐u, C. C.; Coleman, R. A.; Pan, M.-L.; Mukherjee, J. *Synapse* 2011, 65, 778.
(29) Bu☐hsbaum, M. S.; Christian, B. T.; Lehrer, D. S.; Narayanan, T. K.; Shi, B.; Mantil, J.; Kemether, E.; Oakes, T. R.; Mukherjee, *J. Schizophr. Res.* 2006, 85, 232.
(30) Oh, Y.-H.; Ahn, D.-S.; Chung, S.-Y.; Jeon, J.-H.; Park, S.-W.; Oh, S. J.; Kim, D. W.; Kil, H. S.; Chi, D. Y.; Lee, S. *J. Phys. Chem. A* 2007, 111, 10152.
(31) Javed, M. R.; Chen, S.; Kim, H.-K.; Wei, L.; Czernin, J.; Kim, C.-J.; Dam, R. M. van; Keng, P. Y. *J. Nucl. Med.* 2014, 55, 321.
(32) Weisz, A. D.; Regazzoni, A. E.; Blesa, M. A. *Croat. Chem. Acta* 2007, 80, 325.
(33) Bahruji, H.; Bowker, M.; Brookes, C.; Davies, P. R.; Wawata, I. *Appl. Catal. Gen.* 2013, 454, 66.
(34) Paz, Y. *Beilstein J. Nanotechnol.* 2011, 2, 845.
(35) Johansson, E. M. J.; Plogmaker, S.; Walle, L. E.; S☐hölin, R.; Borg, A.; Sandell, A.; Rensmo, H. *J. Phys. Chem. C* 2010, 114, 15015.
(36) Huang, A.; Liu, C.; Ma, L.; Tong, Z.; Lin, R. *J. Chem. Thermodyn.* 2012, 49, 95.
(37) Kir☐hner, B.; Hutter, *J. Chem. Phys. Lett.* 2002, 364, 497.
(38) Kir☐hner, B.; Reiher, M. *J. Am. Chem. Soc.* 2002, 124, 6206.
(39) Jerie, K.; Baranowski, A.; Rozenfeld, B.; Jeżowska-Trzebiatowska, B.; Gliński, *J. Acta Phys. Pol. A* 1991, 79, 507.
(40) Zhang, S.; Liu, Q.; Cheng, H.; Zeng, F. *Appl. Surf. Sci.* 2015, 331, 234.

(41) Letaief, S.; Leŏlerŏq, J.; Liu, Y.; Detellier, C. *Langmuir* 2011, 27, 15248.
(42) Minella, M.; Faga, M. G.; Maurino, V.; Minero, C.; Pelizzetti, E.; Coluŏia, S.; Martra, G. *Langmuir* 2010, 26, 2521.
(43) Minero, C.; Mariella, G.; Maurino, V.; Pelizzetti, E. *Langmuir* 2000, 16, 2632.
(44) Minero, C.; Mariella, G.; Maurino, V.; Vione, D.; Pelizzetti, E. *Langmuir* 2000, 16, 8964.
(45) Habuda-Stanić, M.; Ravančić, M.; Flanagan, A. *Materials* 2014, 7, 6317.
(46) Lu, S.; Giamis, A. M.; Pike, V. W. *Curr. Radiopharm.* 2009, 2, 1.
(47) Keng, P. Y.; Chen, S.; Ding, H.; Sadeghi, S.; Shah, G. J.; Dooraghi, A.; Phelps, M. E.; Satyamurthy, N.; Chatziioannou, A. F.; Kim, C.-J.; van Dam, R. M. *Proc. Natl. Acad. Sci.* 2012, 109, 690.
(48) Seok Moon, B.; Hyung Park, J.; Jin Lee, H.; Sun Kim, J.; Sup Kil, H.; Se Lee, B.; Yoon Chi, D.; Chul Lee, B.; Kyeong Kim, Y.; Eun Kim, S. *Appl. Radiat. Isot.* 2010, 68, 2279.
(49) Lazari, M.; Collins, J.; Shen, B.; Farhoud, M.; Yeh, D.; Maraglia, B.; Chin, F. T.; Nathanson, D. A.; Moore, M.; Dam, R. M. van. *J. Nucl. Med. Technol.* 2014, 42, 203.
(50) Ipaŏh; Sŏhäfer, R.; Mittag, F.; Leiŏhtle, C.; Wolf, P.; Kluba, T. *BMC Musculoskelet. Disord.* 2012, 13, 159.
(51) Patton, M. S.; Lyon, T. D. B.; Ashŏroft, G. P. *Acta Orthop.* 2008, 79, 820.
(52) Rodushkin, I.; Ödman, F.; Branth, S. *Fresenius J. Anal. Chem.* 1999, 364, 338.
(53) Shao, X.; Sŏhnau, P. L.; Fawaz, M. V.; Sŏott, P. J. H. *Nucl. Med. Biol.* 2013, 40, 109.
(54) Radiopharmaceuticals for Position Emission Tomography—Compounding. U.S. Pharmacopeial Convention, Chapter 823, USP 35-NF 50. 2012; pp 398-406.
(55) Liu, Z.; Li, Y.; Lozada, J.; Wong, M. Q.; Greene, J.; Lin, K.-S.; Yapp, D.; Perrin, D. M. *Nucl. Med. Biol.* 2013, 40, 841.
(56) Millet, P.; Moulin-Sallanon, M.; Tournier, B. B.; Dumas, N.; Charnay, Y.; Ibáñez, V.; Ginovart, N. *NeuroImage* 2012, 62, 1455.
(57) Vandehey, N. T.; Moirano, J. M.; Converse, A. K.; Holden, J. E.; Mukherjee, J.; Murali, D.; Niŏkles, R. J.; Davidson, R. J.; Sŏhneider, M. L.; Christian, B. T. *J. Cereb. Blood Flow Metab. Off. J. Int. Soc. Cereb. Blood Flow Metab.* 2010, 30, 994.
(58) Honer, M.; Brühlmeier, M.; Missimer, J.; Sŏhubiger, A. P.; Ametamey, S. M. *J. Nucl. Med.* 2004, 45, 464.
(59) Rominger, A.; Mille, E.; Zhang, S.; Boning, G.; Förster, S.; Nowak, S.; Gildehaus, F. J.; Wängler, B.; Bartenstein, P.; Cumming, P. *J. Nucl. Med.* 2010, 51, 1576.
(60) Mukherjee, J.; Yang, Z.-Y.; Das, M. K.; Brown, T. *Nucl. Med. Biol.* 1995, 22, 283.
(61) Elizarov, A. M.; van Dam, R. M.; Shin, Y. S.; Kolb, H. C.; Padgett, H. C.; Stout, D.; Shu, J.; Huang, J.; Daridon, A.; Heath, J. R. *J. Nucl. Med.* 2010, 51, 282.
(62) Lebedev, A.; Miraghaie, R.; Kotta, K.; Ball, C. E.; Zhang, J.; Buŏhsbaum, M. S.; Kolb, H. C.; Elizarov, A. *Lab. Chip* 2012, 13, 136.
(63) Lazari, M.; Narayanam, M. K.; Murphy, J. M.; Van Dam, R. M. "Automated concentration of $^{18}$F-fluoride in microliter volumes". Proceedings of 21$^{st}$ International Symposium on Radiopharmaceutical Sciences (ISRS-2015), Columbia, Mo., USA, May 26-31, 2015. Oral presentation assigned.
(64) D. Hanahan, R. A. Weinberg, *Cell.* 2000, 100, 57-70.
(65) L. Cai, S. Lu, V. W. Pike, *Eur. J. Org. Chem.* 2008, 2853-2873.
(66) R. Schirrmacher, C. Wangler, E. Schirrmacher, *Mini-Rev. Org. Chem.* 2007, 4, 317-329.
(67) J. W. Seo, B. S. Lee, S. J. Lee, S. J. Oh, D. Y. Chi, *Bull. Korean Chem. Soc.* 2011, 32, 71-76.
(68) M. R. Javed, S. Chen, J. Lei, J. Collins, M. Sergeev, H.-K. Kim, C.-J. Kim, R. M. van Dam, P. Y. Keng, *Chem. Comm.* 2014, 50, 1192-1194.
(69) a) M. Onega, M. Winkler, D. O'Hagan, *Future Med. Chem.* 2009, 1(5), 865-873; b) A. S. Eustaquio, D. O'Hagan, B. S. Moore, *J. Nat. Prod.* 2010, 73, 378-382.
(70) a) M. E. Sergeev, F. Morgia, M. R. Javed, M. Doi, P. Y. Keng, *J. Mol. Cat.: B.* 2013, 92, 51-56; b) M. E. Sergeev, F. Morgia, M. R. Javed, M. Doi, P. Y. Keng, *J. Mol. Cat.: B.* 2013, 97, 74-79.
(71) a) E. Lee, J. M. Hooker, T. Ritter, *J. Am. Chem. Soc.* 2012, 134, 17456-17458; b) E. Lee, A. S. Kamlet, D. C. Powers, C. N. Neumann, G. B. Boursalian, T. Furuya, D. C. Choi, J. M. Hooker, T. Ritter, *Science.* 2011, 334, 639-642.
(72) J.-H. Chun, S. Telu, S. Lu, Victor W. Pike, *Org. Biomol. Chem.* 2013, 11, 5094-5099.
(73) W. J. McBride, R. M. Sharkey, D. M. Goldenberg, *Eur. J. Nucl. Med. Mol. Imaging Research.* 2013, 3, 36.
(74) S. G. Kumar, L. G. Devi. *J. Phys. Chem. A.* 2011, 115, 13211-13241.
(75) T. Froschl, U. Hormann, P. Kubiak, G. Kucerova, M. Pfanzelt, C. K. Weiss, R. J. Behm, N. Husing, U. Kaiser, K. Landfester, M. Wohlfahrt-Mehrens, *Chem. Soc. Rev.* 2012, 41, 5313-5360.
(76) C. Zhang, P. J. D. Lindan, *J. Chem. Phys.* 2003, 118(10), 4620-4630.
(77) U. Diebold, *Surf. Sci. Rep.* 2003, 48, 53-229.
(78) B. Hammer, S. Wendt, F. Besenbacher, *Top. Catal.* 2010, 53, 423-430.
(79) I. Onal, S. Soyer, S. Senkan, *Surf. Sci.* 2006, 600, 2457-2469.
(80) M. R. Javed, S. Chen, H.-K. Kim, L. Wei, J. Czernin, C.-J. Kim, R. M. van Dam, P. Y. Keng, *J. Nuc. Med.* 2013, 55, 1-8.
(81) S. S. Tripathy, J.-L. Bersillon, K. Gopal, *Sep. Purif. Technol.* 2006, 50, 310-317.
(82) A. D. Weisz, A. E. Regazzoni, M. A. Blesa. *Croat. Chem. Acta.* 2007, 80, 325-332.
(83) H. Bahruji, M. Bowker, C. Brookes, P. R. Davies, I. Wawata. *Appl. Cat. A: General.* 2013, 454, 66-73.

EMBODIMENTS

Embodiment 1

A method of forming an [$^{18}$F]-labeled organic compound in an aqueous medium, the method comprising:
combining within an aqueous medium an aqueous [$^{18}$F] fluoride, a transition metal oxide and an organic compound precursor comprising a reactive carbon; and
allowing said aqueous [$^{18}$F] fluoride source to react with said reactive carbon thereby forming said [$^{18}$F]-labeled organic compound.

Embodiment 2

The method of claim 1, wherein said organic compound precursor is an aryl organic compound precursor and said [$^{18}$F]-labeled organic compound is an [$^{18}$F]-labeled aryl organic compound.

Embodiment 3

The method of one of claim 1 or 2, wherein said aqueous medium is less than about 5%, 10%, 15%, 20% or 25% water.

Embodiment 4

The method of one of claims 1 to 3, wherein said [$^{18}$F]-labeled organic compound is a positron emission tomography probe.

Embodiment 5

The method of one of claims 1 to 4, wherein said reacting is SN2 nucleophilic substitution reaction.

Embodiment 6

The method of one of claims 1 to 5, wherein the reactive carbon forms part of a substituted or unsubstituted aryl, substituted or unsubstituted heteroaryl, substituted or unsubstituted alkyl, substituted or unsubstituted heteroalkyl, substituted or unsubstituted cycloalkyl or substituted or unsubstituted heterocycloalkyl.

Embodiment 7

The method of one of claims 1 to 5, wherein the reactive carbon forms part of a substituted or unsubstituted alkyl, substituted or unsubstituted heteroalkyl, substituted or unsubstituted cycloalkyl or substituted or unsubstituted heterocycloalkyl.

Embodiment 8

The method of one of claims 1 to 7, wherein said transition metal oxide is chromium(VI) oxide, molybdenum(VI) oxide, platinum(IV) oxide, rhenium(VI) oxide, rhenium(VII) oxide, ruthenium(IV) oxide, tantalum(V) oxide, tin(IV) oxide, vanadium(IV) oxide, vanadium(V) oxide, yttrium(III) oxide, zirconium(IV) oxide, chromium(III) oxide, bismuth(III) oxide, manganese(IV) oxide, tungsten(IV) oxide, molybdenum(IV) oxide, tungsten(VI) oxide, palladium(II) oxide, iron(II) oxide, zinc(II) oxide, indium(III) oxide, copper(II) oxide, niobium(IV) oxide, niobium(V) oxide, or titanium(IV) oxide.

Embodiment 9

The method of one of claims 1 to 7, wherein said transition metal oxide is palladium(II) oxide, iron(II) oxide, zinc(II) oxide, indium(III) oxide, copper(II) oxide, niobium(IV) oxide, niobium(V) oxide, or titanium(IV) oxide.

Embodiment 10

The method of one of claims 1 to 7, wherein said transition metal oxide is $TiO_2$, $NbO_2$, $Nb_2O_5$, $In_2O_3$, or CuO.

Embodiment 11

The method of one of claims 1 to 10, wherein said aqueous medium further comprises a base.

Embodiment 12

The method of one of claims 1 to 10, wherein said aqueous medium further comprises an ammonium base.

Embodiment 13

The method of one of claims 1 to 10, wherein said aqueous medium further comprises an ammonium bicarbonate base.

Embodiment 14

The method of one of claims 1 to 13, wherein said aqueous medium further comprises an alcohol co-solvent, optionally MeOH, EtOH, n-PrOH, i-PrOH, t-BuOH, tHexOH, n-octanol or cyclohexanol.

Embodiment 15

The method of one of claims 1 to 13, wherein said aqueous medium further comprises an alcohol co-solvent, optionally t-BuOH, tHexOH, n-octanol or cyclohexanol.

Embodiment 16

The method of one of claims 1 to 15, wherein said reactive compound or said organic compound precursor is attached to a tosylate moiety.

Embodiment 17

The method of one of claims 1 to 16, wherein said aqueous [$^{18}$F] fluoride is generated from a cyclotron and is not dried or azeotroped after generation from said cyclotron.

What is claimed is:

1. A method of forming an [$^{18}$F]-labeled organic compound in an aqueous medium, the method comprising:
combining within an aqueous medium an aqueous [$^{18}$F] fluoride, a transition metal oxide and an organic compound precursor comprising a reactive carbon; and
allowing said aqueous [$^{18}$F] fluoride source to react with said reactive carbon thereby forming said [$^{18}$F]-labeled organic compound,
wherein said transition metal oxide is chromium(VI) oxide, molybdenum(VI) oxide, platinum(IV) oxide, rhenium(VI) oxide, rhenium(VII) oxide, ruthenium(IV) oxide, tantalum(V) oxide, tin(IV) oxide, vanadium(IV) oxide, vanadium(V) oxide, yttrium(III) oxide, zirconium(IV) oxide, chromium(III) oxide, bismuth(III) oxide, manganese(IV) oxide, tungsten(IV) oxide, molybdenum(IV) oxide, tungsten(VI) oxide, palladium(II) oxide, iron(II) oxide, zinc(II) oxide, indium(III) oxide, copper(II) oxide, niobium(IV) oxide, niobium(V) oxide, or titanium(IV) oxide.

2. The method of claim 1, wherein said organic compound precursor is an aryl organic compound precursor and said [$^{18}$F]-labeled organic compound is an [$^{18}$F]-labeled aryl organic compound.

3. The method of claim 1, wherein said aqueous medium is less than about 5%, 10%, 15%, 20% or 25% water.

4. The method of claim 1, wherein said [$^{18}$F]-labeled organic compound is a positron emission tomography probe.

5. The method of claim 1, wherein said reacting is SN2 nucleophilic substitution reacting.

6. The method of claim 1, wherein the reactive carbon forms part of a substituted or unsubstituted aryl, substituted or unsubstituted heteroaryl, substituted or unsubstituted alkyl, substituted or unsubstituted heteroalkyl, substituted or unsubstituted cycloalkyl or substituted or unsubstituted heterocycloalkyl.

7. The method of claim 1, wherein the reactive carbon forms part of a substituted or unsubstituted alkyl, substituted or unsubstituted heteroalkyl, substituted or unsubstituted cycloalkyl or substituted or unsubstituted heterocycloalkyl.

8. The method of claim 1, wherein said transition metal oxide is palladium(II) oxide, iron(II) oxide, zinc(II) oxide, indium(III) oxide, copper(II) oxide, niobium(IV) oxide, niobium(V) oxide, or titanium(IV) oxide.

9. The method of claim 1, wherein said transition metal oxide is $TiO_2$, $NbO_2$, $Nb_2O_5$, $In_2O_3$, or CuO.

10. The method of claim 1, wherein said aqueous medium further comprises a base.

11. The method of claim 1, wherein said aqueous medium further comprises an ammonium base.

12. The method of claim 1, wherein said aqueous medium further comprises an ammonium bicarbonate base.

13. The method of claim 1, wherein said aqueous medium further comprises an alcohol co-solvent, optionally MeOH, EtOH, n-PrOH, i-PrOH, t-BuOH, tHexOH, n-octanol or cyclohexanol.

14. The method of claim 1, wherein said aqueous medium further comprises an alcohol co-solvent, optionally t-BuOH, tHexOH, n-octanol or cyclohexanol.

15. The method of claim 1, wherein said organic compound precursor is attached to a tosylate, benzenesulfonyl, 4-nitrobenzenesulfonyl, methanesulfonyl, ethanesulfonyl, trifluoromethylsulfonyl, or 1,1,2,2-pentafluoroethane-1-sulfonyl moiety.

16. The method of claim 1, wherein said aqueous [$^{18}$F] fluoride is generated from a cyclotron and is not dried or azeotroped after generation from said cyclotron.

* * * * *